United States Patent [19]

Kyotani et al.

[11] Patent Number: 5,510,366

[45] Date of Patent: Apr. 23, 1996

[54] INDOLE DERIVATIVES, SALTS THEREOF, AND CONGESTIVE HEART FAILURE THERAPEUTIC AGENTS COMPRISING THE SAME

[75] Inventors: Yoshinori Kyotani; Katsumi Kawamine; Tsutomu Toma; Tadaaki Ohgiya, all of Higashimurayama; Takashi Yamaguchi, Urawa; Kazuhiro Onogi, Iruma; Seiichi Sato, Tokyo; Noboru Shimizu, Higashimurayama; Hiromichi Shigyo, Fuchu; Tomio Ohta, Sayama; Toshiaki Oda, Higashimurayama; Yukihiro Okuno, Higashimurayama; Kimiyuki Shibuya, Higashimurayama; Yoshio Takahashi; Mikio Fujii, both of Iruma; Yasumi Uchida, Ichikawa, all of Japan

[73] Assignee: Kowa Co., Ltd., Nagoya, Japan

[21] Appl. No.: 330,670

[22] Filed: Oct. 28, 1994

[30] Foreign Application Priority Data

Oct. 29, 1993 [JP] Japan .................. 5-271770

[51] Int. Cl.⁶ .................. A61K 31/40; C07D 491/056
[52] U.S. Cl. .................. 514/411; 548/430; 548/431
[58] Field of Search .................. 514/411; 548/431, 548/430

[56] References Cited

FOREIGN PATENT DOCUMENTS

| 0055043 | 6/1982 | European Pat. Off. . |
| WO87/00522 | 1/1987 | WIPO . |
| WO91/13872 | 9/1991 | WIPO . |

OTHER PUBLICATIONS

Bauta, W. E., "Cyclohexadienone Annulations of Aryl Carbene Complexes of Chromium: New Strategies for the Synthesis of Indole Alkaloids," J. Org. Chem, 1989, 54, 3249–3252.

Masaguer, C. F. "Alkylation of 3-Ethyl-2-Methyl-4-Oxo-4,5,6,7-Tetrahydroindole with Bromoesters: Benzenesulfonyl as Convenient Nitrogen Protecting Group," Heterocycles, vol. 34, No. 7, 1992, 1303–09.

Primary Examiner—Jacqueline Haley
Attorney, Agent, or Firm—Oblon, Spivak, McClelland, Maier & Neustadt

[57] ABSTRACT

An indole derivative represented by formula (1),

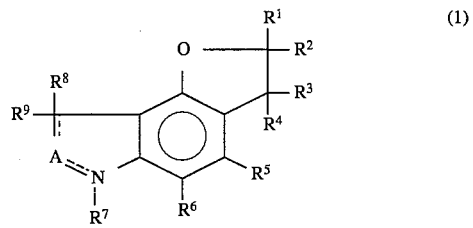

wherein A is a group

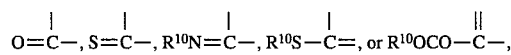

wherein $R^{10}$ is hydrogen or lower alkyl, dotted lines may optionally be resent, and $R^1$–$R^9$ represents various substitutional groups. The compound (1) exhibits a positive inotropic action on cardiac muscle, an anti-arrhythmic action, and a vasodilation action without increasing the heart rate. A heart affection therapeutic agent comprising this compound as an effective component is extremely effective for treating heart failures and arrhythmia.

9 Claims, No Drawings

INDOLE DERIVATIVES, SALTS THEREOF, AND CONGESTIVE HEART FAILURE THERAPEUTIC AGENTS COMPRISING THE SAME

BACKGROUND OF THE INVENTION

1. Field of the Invention

The present invention relates to a novel indole derivative exhibiting pharmaceutical actions such as a positive inotropic action, an anti-arrhythmic action, and a vasodilation action, pharmaceutically acceptable salts thereof, and a heart affection therapeutic agent comprising as an active ingredient the indole derivative or the salt thereof.

2. Description of the Background Art

Congestive heart failure is a state of disease involving a reduction in the cardiac output due to functional abnormalities of heart, accompanied by incapability of ejecting a sufficient quantity of blood required for tissues to metabolize. Heart failures were recently described by J. N. Cohn as a syndrome caused by a cardiac function insufficiency which involves (i) an decrease in a kinetic tolerance capacity, (ii) frequent occurrence of ventricular arrhythmia, and (iii) disorders occurring during the aftercare (J. N. Cohn, Circulation, 78, 1099 (1988)).

Diuretics, vasodilators and cardiac stimulants such as digitalis are used for the improvement of these syndromes.

Digitalis compounds are currently used widely as a cardiac stimulant. Digoxin, one of digitalis compounds, has been confirmed to promote cardiac ejection fractions and to suppress acceleration of heart failures. Digoxin further exhibits an action of decreasing the heart rate. It exhibits a long sustained action, does not produce drug resistance, and can be orally administered. In spite of these significant advantages, the effective concentration in blood and the toxic dose of digoxin are very close each other. In addition, digoxin sometimes induces arrhythmia. Because of these drawbacks of digoxin, research and development of non-glycoside cardiac stimulants which can be administered orally is being strongly promoted more recently.

An object of the present invention is therefore to provide a compound exhibiting a positive inotropic action, an anti-arrhythmic action, and a vasodilation action, and useful as a heart affection therapeutic agent.

In view of this situation the present inventors have synthesized a number of compounds and have undertaken screening of these compounds using the positive inotropic action, the anti-arrhythmic action, and the vasodilation action as indicators. As a result, the present inventors have found that novel indole derivatives represented by formula (1) described below and pharmaceutically acceptable salts thereof can satisfy the above object and useful as a drug for treating heart affections. These findings have led to the completion of the present invention.

SUMMARY OF THE INVENTION

Accordingly, an object of the present invention is to provide an indole derivative represented by the following formula (1),

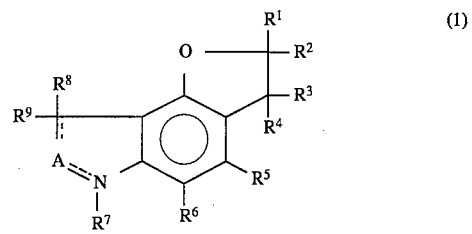

wherein at least one of $R^1$, $R^2$, $R^3$, $R^4$ is a lower alkyl or alkenyl group which may have substituents, and others represent a hydrogen atom or a lower alkyl group; $R^5$ and $R^6$ individually represent a hydrogen atom, a halogen atom, or a lower alkyl or acyl group which may have substituents; $R^7$ may either represent a hydrogen atom or a benzyl group, or form a double bond with A; and $R^8$ and $R^9$ individually represent a hydrogen atom, a halogen atom, a hydroxy group, or a lower alkyl group which may have substituents, or $R^8$ and $R^9$ may together represent an oxygen atom, an alkenyl group which may have substituents, or either one of $R^8$ and $R^9$ may form a double bond with A; and A represents a group

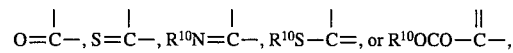

wherein $R^{10}$ is a hydrogen atom or a lower alkyl group; and the dotted line indicates that the bond may be a double bond; or a pharmaceutically acceptable salt thereof.

Another object of the present invention is to provide a heart affection therapeutic agent comprising an indole derivative represented by the above formula (1) or a pharmaceutically acceptable salt thereof as an effective component.

Still another object of the present invention is to provide said drug composition comprising an indole derivative represented by formula (1) or a pharmaceutically acceptable salt thereof and a pharmaceutically acceptable carrier.

A further object of the present invention is to provide a method of treating a patient suffering from heart affection, which comprises administering an effective amount of said indole derivative represented by formula (1) or a pharmaceutically acceptable salt thereof to said patient.

A still further object of the present invention is to provide use of said indole derivative represented by formula (1) or a pharmaceutically acceptable salt thereof as a drug.

These and other objects, features, and advantages of the present invention will become more apparent from the following description of the preferred embodiments taken in conjunction with the accompanying drawings.

DETAILED DESCRIPTION OF THE INVENTION AND PREFERRED EMBODIMENTS

The indole derivatives represented by formula (1) of the present invention fall into any of the following five types depending on the kind of group A,

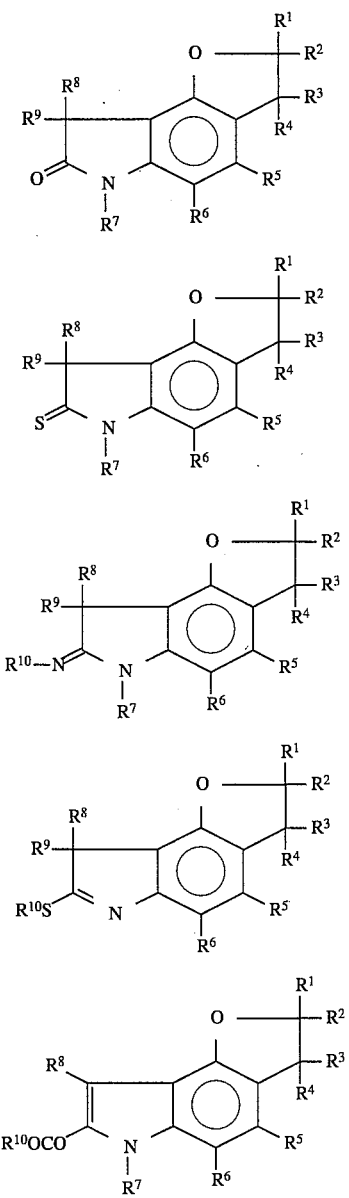

wherein $R^1, R^2, R^3, R^4, R^5, R^6, R^7, R^8, R^9$, and $R^{10}$ have the same meanings as defined above.

Among these, compounds represented by formula (1a), (1b), or (1c), wherein A in formula (1) is

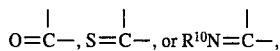

respectively, are preferred. Compounds having

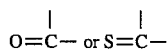

for A are particularly preferred.

In formula (1), given as examples of lower alkyl groups are linear, branched, or cyclic alkyl groups having 1–8, preferably 1–5, carbon atoms; and as examples of lower alkenyl groups are linear or branched alkenyl groups having 2–8, preferably 2–5, carbon atoms. Fluorine, chlorine, bromine, and iodine are given as halogen atoms. As examples of acyl groups, alkanoyl groups having 1–6 carbon atoms and aroyl groups, such as benzoyl group, are given.

As examples of substituents for the "lower alkyl or alkenyl group which may have substituents" for $R^1, R^2, R^3$, or $R^4$, halogen atoms hydroxy group, alkylsulfonyloxy groups, alkylsilyloxy groups, azido groups, cyano groups, amino groups which may have substituents, and cyclic amino groups which may have substituents, are given.

Here, examples of alkylsilyloxy groups include alkylsilyloxy groups having 1–8, preferably 1–5, carbon atoms. Examples of alkylsulfonyloxy groups include alkylsulfonyloxy groups having 1–8, preferably 1–5, carbon atoms. Included in examples of amino groups which may have substituents are amino groups containing one or two substituents selected from the groups consisting of alkyl groups which may further contain substituents, aralkyl groups which may further contain substituents, acyl groups which may further contain substituents, alkoxycarbonyl groups, aryl groups which may further contain substituents, and heterocyclic groups which may further contain substituents. Among these, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, and alkoxycarbonylamino groups having 2–10 carbon atoms are preferred groups. Further, included in preferred cyclic amino groups which may have substituents are pyrrole, pyrrolidine, imidazole, imidazoline, oxazole, oxazoline, thiazole, thiazoline, piperidine, piperazine, morpholine, and the like, all of which may have substituents such as alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups.

More preferred examples of lower alkyl groups which may have substituents represented by $R^1, R^2, R^3$, or $R^4$ are alkenyl groups having 2–5 carbon atoms, alkyl groups having 1–5 carbon atoms, halogenoalkyl groups having 1–5 carbon atoms, hydroxyalkyl groups having 1–5 carbon atoms, aminoalkyl groups having 1–5 carbon atoms, mono- or dialkyl aminoalkyl groups having 1–10 carbon atoms, alkylsilyloxyalkyl groups having 2–10 carbon atoms, alkylsulfonyloxyalkyl groups having 2–10 carbon atoms, azidoalkyl groups having 1–5 carbon atoms, cyanoalkyl groups having 1–5 carbon atoms; aralkylaminoalkyl groups, acylaminoalkyl groups, alkoxycarbonylaminoalkyl groups, arylaminoalkyl groups, heteroarylaminoalkyl groups, substituted pyrrolylalkyl groups, substituted pyrrolidinylalkyl groups, substituted imidazolylalkyl groups, substituted imidazolinylalkyl groups, substituted oxazolylalkyl groups, substituted oxazolinylalkyl groups, substituted thiazolylalkyl groups, substituted thiazolinylalkyl groups, substituted piperidinylalkyl groups, substituted piperazinylalkyl groups, and substituted morpholinoalkyl groups, all having 9–30 carbon atoms; and the like.

Especially preferred examples of lower alkyl groups which may have substituents represented by $R^1, R^2, R^3$, or $R^4$ are alkyl groups having 1–8 carbon atoms and containing substituents selected from amino group, mono- or dialkylamino groups having 1–16 carbon atoms, phenyl alkylamino groups having 7–15 carbon atoms, pyrrole, pyrrolidine, imidazole, imidazoline, oxazole, oxazoline, thiazole, thiazoline, piperidine, piperazine, and morpholine, all of which may have further substituted by alkyl groups having 1–8 carbon atoms, phenyl alkyl groups having 7–15 carbon atoms, benzoyl group, alkoxybenzoyl groups having 1–8 carbon atoms, or di($C_{1-8}$)alkoxybenzoyl groups.

Included in examples of lower alkyl groups which may have substituents represented by $R^5, R^6, R^8$, or $R^9$ are hydroxyalkyl groups, halogenoalkyl groups, cyanoalkyl groups, alkoxycarbonylalkyl groups, and carboxyalkyl groups, having 1–8 carbon atoms.

Of the groups. represented by $R^5$ or $R^6$, preferred groups are hydrogen, halogens, alkyl groups having 1–8 carbon atoms, and alkanoyl groups having 1–6 carbon atoms, with especially preferred being hydrogen, halogens, alkyl groups having 1–5 carbon atoms, and alkanoyl groups having 2–4 carbon atoms.

Of the groups represented by $R^8$ or $R^9$, preferred groups are hydrogen, hydroxy group, and alkyl groups having 1–8 carbon atoms. Hydrogen and alkyl groups having 1–5 carbon atoms are particularly preferred.

Specific examples of preferred lower alkyl groups are methyl, ethyl, n-propyl, iso-propyl, n-butyl, iso-butyl, tert-butyl, n-pentyl, and the like. Specific examples of preferred lower alkenyl groups are vinyl, propenyl, butenyl, and the like.

Pharmaceutically acceptable salts of compound (1) of the present invention include acid addition salts of inorganic acids, such as hydrochloric acid, sulfuric acid, or nitric acid, organic acids, such as fumaric acid, tartaric acid, maleic acid, or succinic acid; carboxylic acid alkali metal salts, such as sodium salt or potassium salt, and alkaline earth metal salts, such as calcium salt or magnesium salt of carboxylic acid group.

Because of the presence of an asymmetric carbon atom, there are optical isomers for compound (1) of the present invention. Both the optical isomers and racemate are included in the present invention. Stereo isomers are also included in the present invention. Further, compound (1) of the present invention may be isolated as a hydrate or a solvate. These are also included in the present invention.

Compound (1) of the present invention can be prepared, for example, according the following processes.

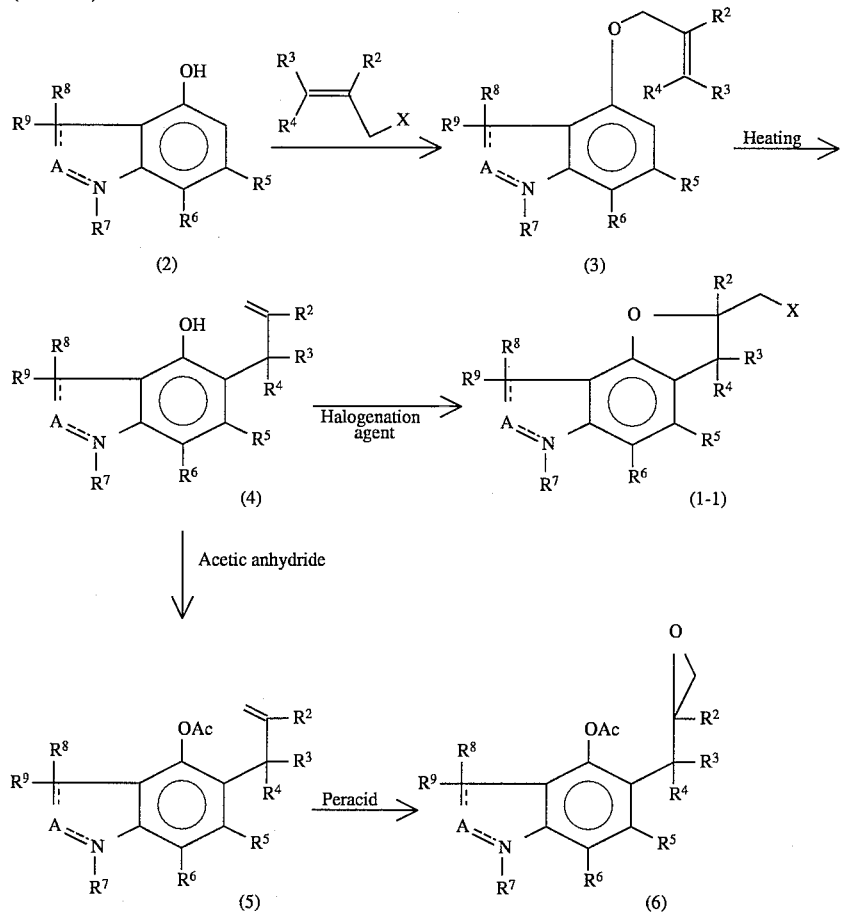

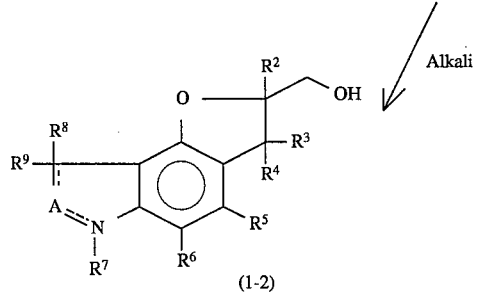

In the above formulas, X is a halogen atom, Ac is an acetyl group, and $R^1$, $R^2$, $R^3$, $R^4$, $R^5$, $R^6$, $R^7$, $R^8$, $R^8$, A, and dotted lines are the same as defined above.

According to the above reaction scheme, an indole compound (2) is reacted with an allylhalide to produce compound (3), which is heated to effect the Claisen rearrangement and then reacted with acetic anhydride to obtain compound (5). This compound (5) is reacted with a peracid to obtain an epoxy compound (6), which is treated with an alkali to obtain compound (1-2) of the present invention. It is possible to directly produce compound (1-2) of the present invention by oxidizing compound (4) with peracid. Further, it is possible to obtain compound (1-1) of the present invention by reacting compound (4) with a halogenation agent such as N-bromosuccimide.

Furthermore, compound (1-2) and its o-trialkylsilyl compound can be obtained by treating compound (6) with an alkali and reacting it with a trialkylsilyl halide. This o-trialkylsilyl compound is converted to compound (1-2) by treating it with an acid.

(Process 2)

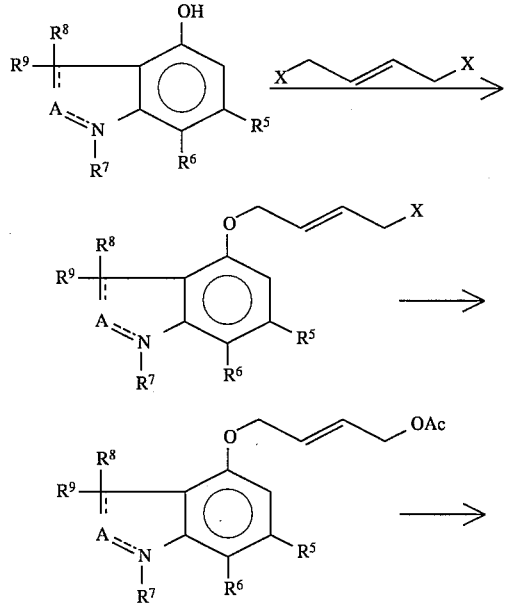

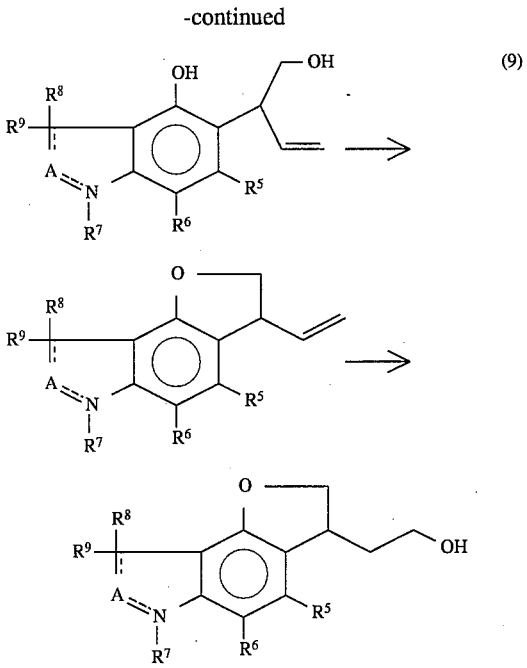

In the above formulas, X, $R^5$, $R^6$, $R^7$, $R^8$, $R^9$, A, and dotted lines are the same as defined above.

According to the above reaction scheme, an indole compound (2) is reached with a dihalogenobutene to produce compound (7), which is acetyloxylated and heated to effect the Claisen rearrangement to obtain compound (9). This compound (9) is dehydrocyclized into compound (1-3) of the present invention. This compound (1-3) can be converted to compound (1-4) by reacting it with a borohydride agent such as 9-borabicyclo[3.3.1]nonane, followed by hydrolysis.

(Process 3)

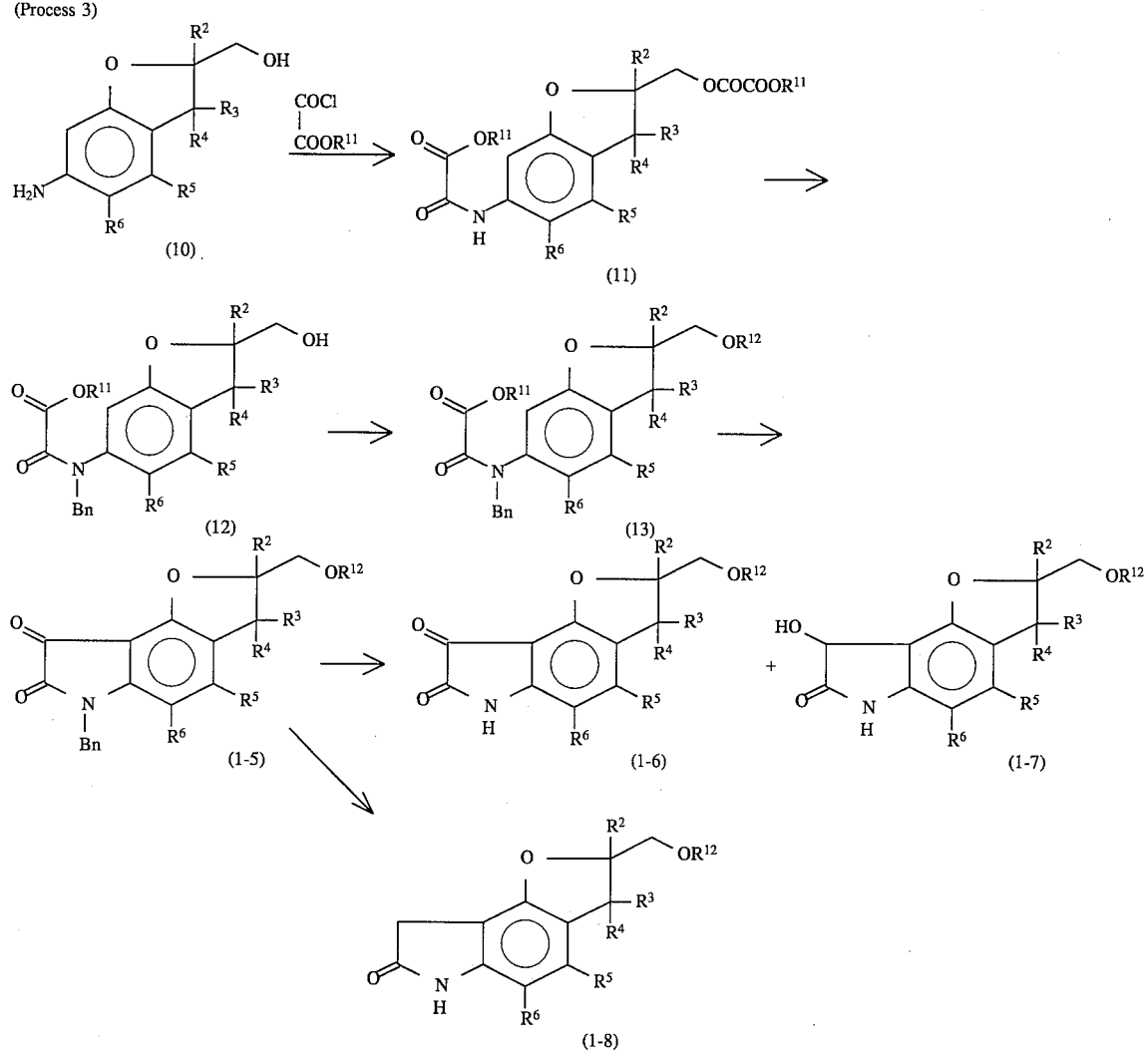

In the above formulas, $R^{11}$ is an alkyl group, $R^{12}$ is a protective group for hydroxy group, Bn is a benzyl group, and $R^2$, $R^3$, $R^4$, $R^5$, and $R^6$ are the same as defined above.

According to the above reaction scheme, compound (10) is reacted with an alkyloxalyl chloride to produce compound (11). This compound (11) is N-benzylated and hydrolyzed to obtain compound (12), which is reacted with a hydroxy group protective group such as mesyl chloride to obtain compound (13). This compound (13) is cyclized by the Friedel-Crafts reaction to obtain compound (1-5) of the present invention.

The compound (1-5) can be reduced into compound (1-6), compound (1-7), or compound (1-8).

(Process 4) Conversion of group A

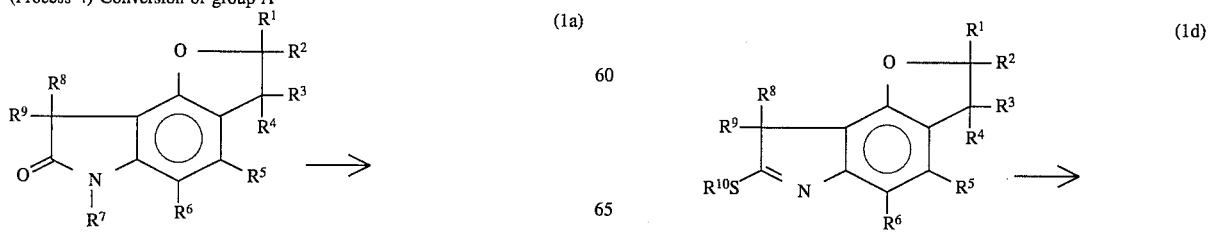

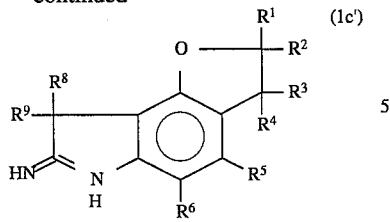

(1c')

In the above formulas, $R^1, R^2, R^3, R^4, R^5, R^6, R^7, R^8, R^9$, and $R^{10}$ are the same as defined above.

According to the above reaction scheme, compound (1a) is reacted with a sulfurization agent such as Lawesson's reagent or the like to produce compound (1b), which is reacted with an alkylation agent such as an alkyl iodide to obtain compound (1d). Further, the compound (1d) is reacted with ammonia to afford (1c'). In these reactions, an amino group or the like which may be present in groups $R^1$ to $R^9$, is desirably protected by a protective group, such as benzyloxycarbonyl group, t-butoxycarbonyl or the like, in advance. The protective group is release after the reaction.

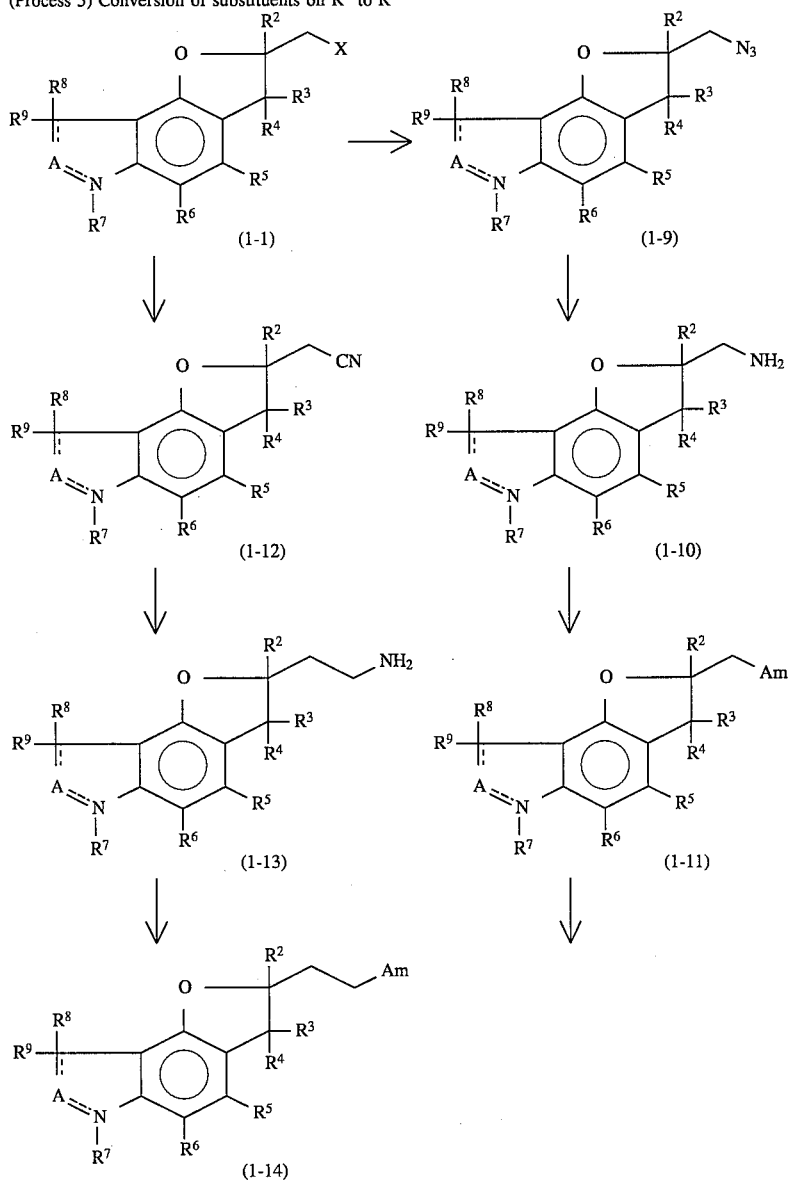

(Process 5) Conversion of substituents on $R^1$ to $R^4$

In the above formulas, Am is an amino group having a substituent, and X, $R^2$ to $R^9$, A and dotted lines are the same as defined above.

According to the above reaction scheme, compound (1-1) is reacted with an azidation agent such as sodium azido to produce compound (1-9), which is converted to compound (1-10) by reduction. Compound (1-11) is then obtained by introducing various substitution groups to the amino group of this compound. On the other hand, compound (1-12) can be obtained by reacting compound (1-1) with a cyanation agent such as potassium cyanide. This compound (1-12) can be converted by reduction into compound (1-13) with a longer alkylene chain length than compound (1-10). Compound (1-14) is then obtained by introducing various substitution groups to the amino group of compound (1-13).

(Process 6) Conversion of substituents on $R^1$ to $R^4$

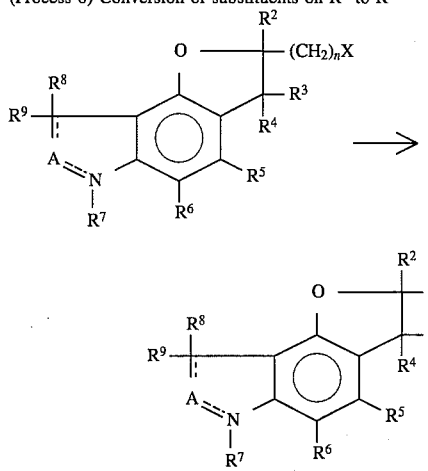

In the above formulas, n is a number 1–8, and X, $R^2$ to $R^9$, A, dotted lines, and Am are the same as defined above.

According to the above reaction scheme, Compound (1-16) is obtained by reacting various amine compounds (e.g., alkyl amine, aralkyl amine, cyclic amine, etc.) with compound (1-15).

Further, substitution groups $R^2$ to $R^9$ can be introduced to specified position on the structure of compound (1a), (1b), (1c), or (1d) by various known methods, after such a structure has been obtained. If desired, the introduced substitution groups can be converted by various processes comprising halogenation, cyanation, hydrolysis, oxidation, reduction, and the like. Processes 7 and 8 described below are specific examples of such conversion processes.

Process 7

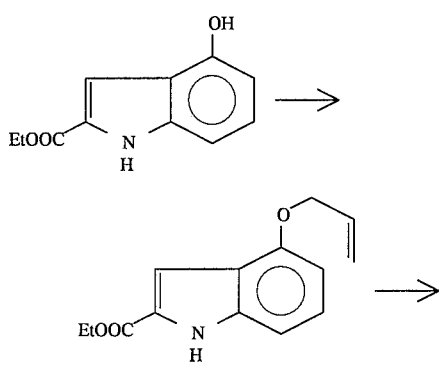

-continued
Process 7

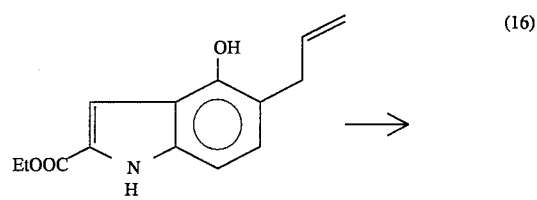

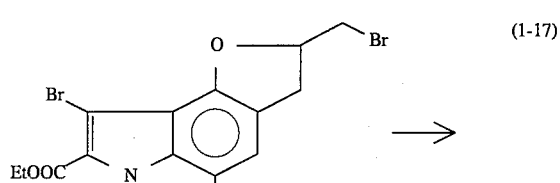

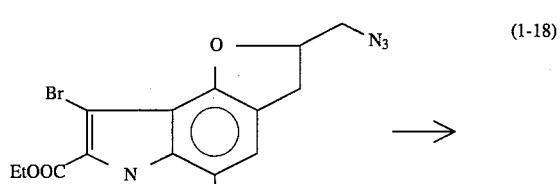

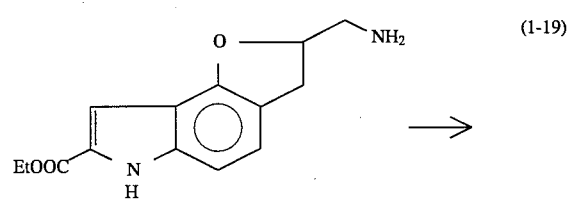

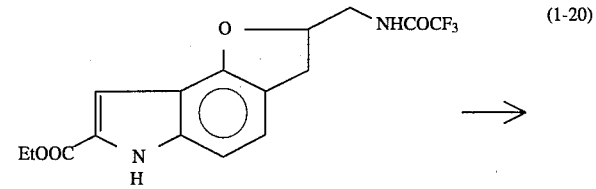

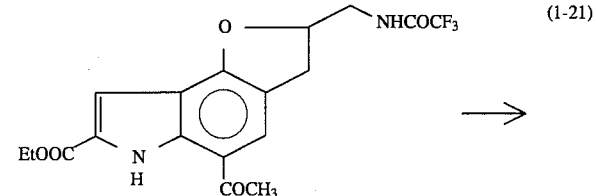

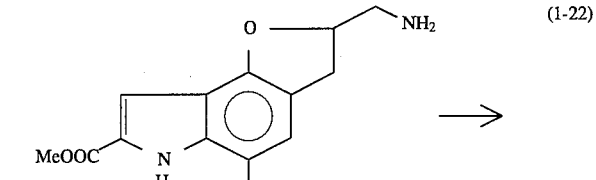

According to the above reaction scheme, compound (1-14) is reacted with an allylhalide to obtain compound (15). After the Claisen rearrangement, the compound (15) is reacted with a halogenation agent such as N-bromosuccinimide to obtain tribromo compound (1-17). The tribromo compound (1-17) is azidated and then reduced to afford an amino compound (1-19). After protecting the amino group, this compound (1-19) is acetylated to obtain compound (1-21) with an acetylated benzene ring. A de-protection reaction of this compound (1-21) in methanol releases the protective group for the amino group and, at the same time, effects the ester exchange reaction replacing ethoxycarbonyl group with methoxycarbonyl group, thus affording compound (1-22). Compound (1-23) can be obtained by a reducing reaction of the above compound, by which acetyl group is converted to ethyl group.

(Process 8)

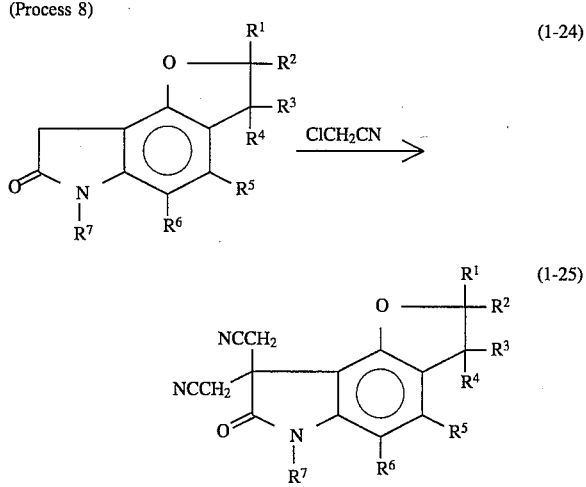

In the above formulas, $R^1$ to $R^7$ are the same as defined above.

According to the above reaction, biscyanomethyl compound (1-25) can be obtained by reacting compound (1-24) and halogenated cyanomethane in the presence of a base.

In the above processes, indole compound (2) can be prepared, for example, from an m-alkoxyaniline compound by protecting the amino group with benzyl group or the like, reacting it with an α-halogenoacetyl halide, and cyclizing the product by the Friedel-Crafts reaction.

Separation of optical isomers of compound (1) of the present invention can be carried out by a resolution method comprising reacting the racemate with a resolution agent and separating the isomers by utilizing the differences in the solubility among the isomers, a method of using optical isomer separation columns, or the like.

The compound (1) of the present invention and its pharmaceutically acceptable salts thus obtained exhibit excellent antiarrhythmic action, vasodilation action, and cardiac action, and the like, as shown in Test Examples hereinafter. Further, the results of acute toxicity tests, in which compound (1) or a pharmaceutically acceptable salt thereof is orally administered to mice demonstrated extremely high $LD_{50}$ values (at a dose of p.o. 400–800 mg/kg), confirming that the compounds are highly safe.

The compounds (1) of the present invention and their pharmaceutically acceptable salts are useful as a drug for treating various heart affections typified by arrhythmia and cardiac failure.

The drug composition of the present invention comprises compound (1) of the present invention or a pharmaceutically acceptable salt thereof as an effective component and, optionally, carriers for pharmaceutical use. It is formed into preparations such as, for example, tablets, powders, capsules, and injections by conventional methods, and usually orally administered or injected by means of subcutaneous, intramuscular, or intravenous injection.

A dose of the drug composition of the present invention is normally in the range of 1 mg to 1 g per day per adult, as the effective component, which is compound (1) of the present invention or a pharmaceutically acceptable salt thereof.

Japanese Patent Application No. 271770/1993, filed on Oct. 29, 1993 is hereby incorporated by reference.

Other features of the invention will become apparent in the course of the following description of the exemplary embodiments which are given for illustration of the invention and are not intended to be limiting thereof.

EXAMPLES

Example 1

(1) 2-Benzylamino-4-ethoxytoluene 100 ml of benzene was added to 20.8 g (138 mmol) of 2-amino-4-ethoxytoluene and 17.8 g (168 mmol) of benzaldehyde, and the mixture was heated with refluxing for 5 hours in a reaction vessel equipped with a water separator. After cooling, the reaction solution was concentrated under reduced pressure. 640 ml of methanol was added to the residue, followed by the addition of acetic acid to adjust pH to 5. To this was added 13.1 g (208 mmol) of sodium cyanoborohydride while stirring under cooling with ice, and the mixture was stirred overnight at room temperature. The reaction mixture was concentrated, purified by column chromatography (silica gel, chloroform), and recrystallized (chloroform-n-hexane) to obtain 19.7 g (yield, 59.2%) of colorless prisms of the title compound.

mp: 69°–71° C.

IR(KBr): 3422, 2850, 1605, 1581, 1506, 1446, 1245, 1165, 825 cm$^{-1}$.

$^1$H-NMR(CDCl$_3$) δ: 1.36(3H, t, J=7.3 Hz), 2.09(3H, s), 3.84(1H, br. s), 3.96(2H, q, J=7.3 Hz), 4.34(2H, s), 6.17–6.26(2H, m), 6.94(1H, d, J=8.8 Hz), 7.27–7.42(5H, m).

MS(m/z): 241(M$^+$), 226

(2) N-Benzyl-2-bromo-5'-ethoxy-2'-methylisobutyranilide 19.53 g (81.0 mmol) of 2-benzylamino-4-ethoxytoluene and 17.8 g (225 mmol) of pyridine was dissolved in 300 ml of methylene chloride. After the addition of 23.8 g (103.6 mmol) of 2-bromo-iso-butylyl bromide while stirring under cooling with ice, the mixture was stirred for 10 hours at room temperature. After the addition of methanol to the reaction mixture to decompose the excess amount of acid bromide, the mixture was washed with water, 2N hydrochloric acid, saturated aqueous solution of sodium hydrogen carbonate, and saturated brine, dried over anhydrous sodium sulfate, and concentrated under reduced pressure. An oily product obtained was purified by column chromatography (silica gel, chloroform) and crystallized from n-hexane to obtain 27.67 g (yield, 87.6%) of colorless crystals of the title compound.

mp: 87°–88° C.

IR(KBr): 2965, 2921, 1629, 1606, 1495, 1465, 1388, 1289, 1173, 1137, 1107, 1036 cm$^{-1}$.

$^1$H-NMR(CDCl$_3$) δ: 1.28(3H, t, J=6.8 Hz), 1.48(3H, br. s), 1.96(3H, s), 2.15(3H, s), 3.65–3.96(3H, m), 5.63(1H, d, J=13.7 Hz), 6.56(1H, d, J=2.0 Hz), 6.79(1H, dd, J=2.0, 8.8 Hz), 7.11(1H, d, J=8.8 Hz), 7.16–7.34(5H, m).

(3) 1-Benzyl-2,3-dihydro-4-hydroxy-3,3,7-trimethyl-1H-indol-2-one 31.2 g (80.0 mmol) of N-benzyl-2-bromo-5'-ethoxy-2'-methylisobutyranilide was dissolved in 258 ml of chlorobenzene. After the addition of 53.2 g (399 mmol) of aluminum chloride powder, the mixture was heated while stirring for 28 minutes at 125° C. The resulting mixture was cooled, washed with water and saturated brine, dried over anhydrous sodium sulfate, and concentrated under reduced pressure. The residue obtained was purified by column chromatography (silica gel, 3:1 mixture of n-hexane and ethyl acetate) and recrystallized (ether-n-hexane) to obtain 9.06 g (yield, 40.3%) of colorless prisms of the title compound.

mp: 128°–129° C.

IR(CHCl$_3$): 3266, 2960, 1683, 1604, 1466, 1442, 1381, 1355, 1269, 950 cm$^{-1}$.

$^1$H-NMR(CDCl$_3$) δ: 1.56(6H, s), 2.19(3H, s), 5.18(2H, s), 5.49(1H, br.), 6.37(1H, d, J=8.3 Hz), 6.73(1H, d, J=8.3 Hz), 7.11(2H, d, J=6.8 Hz), 7.17–7.35(3H, m).

(4) 2,3-Dihydro-4-hydroxy-3,3,7-trimethyl-1H-indol-2-one 41.0 g (146 mmol) of 1-benzyl-2,3-dihydro-4-hydroxy-3,3,7-trimethyl-1H-indol-2-one was dissolved in 1 l of acetic acid. After the addition of 82 g of a 10% palladium-carbon catalyst, the reaction atmosphere was replaced with hydrogen and 40 ml (160 mmol) of 4N hydrogen chloride solution in ethyl acetate was added, following which the mixture was stirred for 2.5 hours over a water bath at 80° C. The catalyst was removed by filtration and the filtrate was concentrated under reduced pressure. The residue obtained was purified by column chromatography (silica gel, 4:1 mixture of chloroform and methanol) and recrystallized (ether) to obtain 27.58 g (yield, 98.9%) of colorless prisms of the title compound.

mp: 190°–192° C.

IR(CHCl$_3$): 3200, 1701, 1626, 1457, 1380, 1311, 1273, 1045 cm$^{-1}$.

$^1$H-NMR(CDCl$_3$) δ: 1.51(6H, s), 2.19(3H, s), 5.50(1H, br), 6.38(1H, d, J=8.3 Hz), 6.84(1H, d, J=8.3 Hz), 8.33(1H, br. s).

(5) 4-Allyloxy-2,3-dihydro-3,3,7-trimethyl-1H-indol-2-one 8.21 g (42.99 mmol) of 2,3-dihydro-4-hydroxy-3,3,7-trimethyl-1H-indol-2-one and 7.95 g (47.3 mmol) of allyl iodide were dissolved in 65 ml of N,N-dimethylformamide. After the addition of 12.0 g (87 mmol) of potassium carbonate, the mixture was stirred for 2 hours over a water bath at 70° C. After the reaction, the solvent was removed by evaporation under reduced pressure. Chloroform was added to the residue, and the mixture was washed with water, 2N sodium hydroxide aqueous solution, and saturated brine, dried over anhydrous sodium sulfate, and concentrated under reduced pressure. The residue obtained was purified by column chromatography (silica gel, 10:1 mixture of chloroform and ethyl acetate) and crystallized from n-hexane to obtain 5.67 g (yield, 57.1%) of colorless crystals of the title compound.

mp: 153°–155° C.

$^1$H-NMR(CDCl$_3$) δ: 1.49(6H, s), 2.19(3H, s), 4.55(2H, m), 5.27(1H, dd, J=2.0, 10.8 Hz), 5.42(1H, dd, J=2.0, 17.6 Hz), 6.04(1H, m), 6.48(1H, d, J=8.3 Hz), 6.93(1H, d, J=8.3 Hz), 7.73(1H, br. s).

(6) 5-Allyl-2,3-dihydro-4-hydroxy-3,3,7-trimethyl-1H-indol-2-one 5.67 g (24.5 mmol) of 4-allyloxy-2,3-dihydro-3,3,7-trimethyl-1H-indol-2-one was added to 13 ml of N,N-dimethylaniline and the mixture was heated with stirring for 17 hours at 205° C. under a nitrogen atmosphere. After the reaction, N,N-dimethylaniline was removed by evaporation under reduced pressure. The residue was dissolved in chloroform and washed with water, 2N hydrochloric acid, and saturated brine, dried over anhydrous sodium sulfate, and concentrated under reduced pressure. The residue obtained was purified by column chromatography (silica gel, 10:1 mixture of chloroform and ethyl acetate) and precipitated in n-hexane. Filtration of the precipitate afforded 4.77 g (yield, 84.1%) of light yellow crystals of the title compound.

mp: 141°–143° C.

IR(KBr): 3493, 3153, 1691, 1629, 1484, 1449, 1257, 1229, 1203, 1111, 925, 764 cm$^{-1}$.

$^1$H-NMR(CDCl$_3$) δ: 1.45(6H, s), 2.17(3H, S), 3.32(2H, d, J=6.4 Hz), 5.12–5.23(3H, m), 5.97(1H, m), 6.70(1H, s), 9.18(1H, br. s).

(7) 2-Bromomethyl-2,3,7,8-tetrahydro-5,8,8-trimethyl-6H-furo[2,3-e]indol-7-one 3.5 g (15.2 mmol) of 5-allyl-2,3-dihydro-4-hydroxy-3,3,7-trimethyl-1H-indol-2-one and 2.72 g (15.3 mmol) of N-bromosuccinimide were dissolved in 120 ml of chloroform, and the mixture was heated with stirring for 40 minutes over a water bath at 75° C. After cooling, the reaction mixture was washed with water and saturated brine, dried over anhydrous sodium sulfate, and concentrated under reduced pressure. The residue obtained was washed with ether and filtered to obtain 4.59 g (yield, 97.4%) of colorless crystals of the title compound.

mp: 195°–196° C.

IR(KBr): 3181, 1702, 1640, 1477, 1458, 1432, 1311, 1255, 1243, 1089 cm$^{-1}$.

$^1$H-NMR(CDCl$_3$) δ: 1.44(3H, s), 1.57(3H, s), 2.17(3H, s), 3.03(1H, dd, J=5.9, 15.6 Hz), 3.32(1H, dd, J=9.3, 15.6 Hz), 3.50(1H, dd, J=6.8, 10.3 Hz), 3.59(1H, dd, J=4.9, 10.3 Hz), 5.02(1H, m), 6.81(1H, s), 7.64(1H, br. s.).

(8) 2-Azidomethyl-2,3,7,8-tetrahydro-5,8,8-trimethyl-6H-furo[2,3-e]indol-7-one 100 ml of N,N-dimethylformamide was added to a mixture of 4.59 g (14.8 mmol) of 2-bromomethyl-2,3,7,8-tetrahydro-5,8,8-trimethyl-6H-furo[2,3-e]indol-7-one and 7.0 g (108 mmol) of sodium azido, and the mixture was heated with stirring for 45 minutes over a water bath at 100° C. After cooling, the solvent was evaporated under reduced pressure. Chloroform was added to the residue, and the mixture was washed with water and saturated brine, dried over anhydrous sodium sulfate, and concentrated under reduced pressure. The residue obtained was washed with ether and filtered to obtain 3.95 g (yield, 98.0%) of colorless crystals of the title compound.

mp: 199°–200° C.

IR(KBr): 3184, 2088, 1683, 1638, 1480, 1454, 1427, 1312, 1277, 1243, 1089, 898, 753 cm$^{-1}$.

$^1$H-NMR(CDCl$_3$) δ: 1.45(6H, s), 2.21(3H, s), 2.94(1H, dd, J=6.8, 15.6 Hz), 3.25(1H, dd, J=9.3, 15.6 Hz), 3.45(2H, d, J=5.4 Hz), 5.01(1H, m), 6.82(1H, s), 8.77(1H, br. s).

(9) 2-Aminomethyl-2,3,7,8-tetrahydro-5,8,8-trimethyl-6H-furo[2,3-e]indol-7-one hydrochloride 4.1 g (15.1 mmol) of 2-azidomethyl-2,3,7,8-tetrahydro-5,8,8-trimethyl-6H-furo[2,3-e]indol-7-one was dissolved in 400 ml tetrahydrofuran. After the addition of 4 g of 10% palladium-carbon catalyst, the solution was stirred for 1 hour at room temperature under a hydrogen atmosphere. The catalyst was removed by filtration, and the filtrate was concentrated and made into hydrochloride. The hydrochloride was recrystallized (methanol-ether) to obtain 3.1 g (yield, 72.7%) of colorless crystals of the title compound.

mp: >250° C.

IR(KBr): 3408, 3178, 2949, 2850, 1690, 1622, 1509, 1479, 1447, 1297, 1242, 1083, 968 cm$^{-1}$.

$^1$H-NMR(CD$_3$OD) δ: 1.38(3H, s), 1.42(3H, s), 2.17(3H, s), 2.90(1H, dd, J=7.3, 15.6 Hz), 3.19(1H, dd, J=8.8, 13.2 Hz), 3.27–3.39(2H, m), 5.01(1H, m), 6.87(1H, s).

(10) 2-(N-Benzyloxycarbonyl)glycylaminomethyl-2,3,7,8-tetrahydro-5,8,8-trimethyl-6 H-furo[2,3-e]indol-7-one 1.0 g (3.54 mmol) of 2-aminomethyl-2,3,7,8-tetrahydro-5,8,8-trimethyl-6H-furo[2,3-e] indol-7-one was dissolved in a mixture of 740 ml of N,N-dimethylformamide and 14 ml of pyridine. To the solution were added 359 mg (3.55 mmol) of N-methylmorpholine, 40 mg (3.54 mmol) of benzyloxycarbonyl glycine, and 1.35 g (7.04 mmol) of 1-ethyl-3-(3-dimethylaminopropyl)carbodimide hydrochloride, and the mixture was stirred for 2 hours at room temperature. After the reaction, the solvent was evaporated under reduced pressure. The residue was washed with water with the addition of chloroform, dried over anhydrous sodium sulfate, and concentrated under reduced pressure. The residue obtained was purified by column chromatography (silica gel, 20:1 mixture of chloroform and methanol) to obtain 1.55 g (yield, quantitative) of a light yellow powder of the title compound.

IR(KBr): 3261, 1700, 1526, 1478, 1454, 1241, 1087, 750 cm$^{-1}$.

$^1$H-NMR(CDCl$_3$) δ: 1.43(3H, s), 1.67(3H, s), 2.16(3H, s), 2.81(1H, m), 3.21(1H, m), 3.44(1H, m), 3.69(1H, m), 3.88(2H, d, J=5.9 Hz), 4.90(1H, m), 5.08(2H, s), 5.36(1H, br.), 6.36(1H, br.), 6.79(1H, s), 7.26(2H, s), 7.34(3H, s).

(11) 2-(N-Glycyl)aminomethyl-2,3,7,8-tetrahydro-5,8,8-trimethyl-6H-furo[2,3-e]indol-7-one·hydrochloride 1.55 g (3.54 mmol) of 2-(N-benzyloxycarbonyl)glycylaminomethyl-2,3,7,8-tetrahydro-5,8,8-trimethyl-6H-furo[2,3e]indol-7-one was dissolved in 20 ml of N,N-dimethylformamide and 1.6 g of 10% palladium-carbon catalyst was added to the solution. The mixture was stirred for 2 hours at room temperature under a hydrogen atmosphere. The catalyst was removed by filtration and the filtrate was concentrated under reduced pressure. The residue was made into hydrochloride and recrystallized (methanol-ether) to obtain 973 g (yield, 80.9%) of a light yellow powder of the title compound.

mp: >250° C.

IR(KBr): 3080, 1701, 1670, 1640, 1557, 1475, 1454, 1253, 1089, 1056, 834 cm$^{-1}$.

$^1$H-NMR(CD$_3$OD) δ: 1.36(3H, s), 1.38(3H, s), 2.16(3H, s), 2.84(1H, m), 3.20(1H, m), 3.51(2H, m), 3.70(2H, s), 5.00(1H, m), 6.82(1H, s).

Example 2

(1) 2-Benzylamino-4-methoxy-1-methylbenzene 20.3 g (0.520 mol) of sodium amide was added to 140 g (1.31 mol) of benzylamine under an argon atmosphere. After stirring under cooling with ice for 20 minutes, a solution of 34.84 g (0.129 mol) of 3-bromo-4-methoxytoluene dissolved in 220 ml of tetrahydrofuran was added dropwise over 90 minutes. The reaction mixture was heated to 60° C. and stirred for 60 minutes. Methanol was added under cooling with ice, followed by further addition of ice water. The reaction mixture was extracted with ethyl acetate. The organic layer was washed with saturated brine, dried over anhydrous sodium sulfate, and concentrated under reduced pressure. The residue was recrystallized (chloroform-n-hexane) to obtain 26.96 g (yield, 68.4%) of colorless needles of the title compound.

mp: 81°–82° C.

IR(KBr): 3422, 2917, 1614, 1580, 1517, 1490, 1449, 1440, 1327, 1277, 1251, 1207, 1163, 1134, 1096, 1063, 989, 826, 774, 729, 694 cm$^{-1}$.

$^1$H-NMR(CDCl$_3$) δ: 2.10(3H, s), 3.73(3H, s), 4.35(2H, s), 6.21–6.23(2H, m), 6.96(1H, d, J=8.9 Hz), 7.25–7.37(5H, m).

The following compounds were prepared in the same manner as in Example 1.

(2) N-Benzyl-2-bromo-5'-methoxy-2'-methylisobutyranilide mp: 81°–82° C.

IR(KBr): 3397, 2930, 2822, 1626, 1610, 1571, 1498, 1454, 1422, 1389, 1366, 1295, 1279, 1240, 1197, 1186, 1176, 1161, 1135, 1113, 1037, 813, 735, 725, 695 cm$^{-1}$.

$^1$H-NMR(CDCl$_3$) δ: 1.48(3H, s), 1.97(3H, s), 2.15(3H, s), 3.58(3H, s), 3.92(1H, d, J=14.1 Hz), 5.64(1H, d, J=14.1 Hz), 6.56(1H, d, J=2.4 Hz), 6.79(1H, dd, J=2.4, 8.3 Hz), 7.12(1H, d, J=8.3 Hz), 7.20–7.29(5H, m).

(3) 1-Benzyl-2,3-dihydro-4-hydroxy-3,3,7-trimethyl-1H-indol-2-one mp: 127°128° C.

IR(KBr): 3271, 3024, 1670, 1627, 1502, 1468, 1381, 1271, 1224, 1094, 951, 802, 725, 693 cm$^{-1}$.

$^1$H-NMR(CDCl$_3$) δ: 1.56(6H, s), 2.19(3H, s), 4.91(1H, br. s), 5.17(2H, s), 6.34(1H, d, J=8.3 Hz), 6.74(1H, d, J=8.3 Hz), 7.11(1H, d, J=6.8 Hz), 7.22–7.35(3H, m).

(4) 2,3-Dihydro-4-(2-methyl-2-propenyl)oxy-3,3,7-trimethyl-1H-indol-2-one mp: 141°–144° C.

IR(KBr): 3148, 3026, 2917, 1715, 1690, 1626, 1602, 1500, 1448, 1375, 1258, 1190, 1076, 984 cm$^1$.

$^1$H-NMR(CDCl$_3$) δ: 1.49(6H, s), 1.84(3H, s), 2.20(3H, s), 4.44(2H, s), 4.99(1H, s), 5.10(1H, s), 6.42(1H, d, J=7.8 Hz), 6.92(1H, d, J=7.8 Hz).

(5) 2,3-Dihydro-4-hydroxy-5-(2-methyl-2-propenyl)-3,3,7-trimethyl-1H-indol-2-one mp: 141°–142° C.

$^1$H-NMR(CDCl$_3$) δ: 1.47(6H, s), 1.74(3H, s), 2.16(3H, s), 3.32(2H, s), 4.93(1H, s), 4.96(1H, s), 5.25(1H, s), 6.72(1H, s).

(6) 2-Bromomethyl-2,3,7,8-tetrahydro-2,5,8,8-tetramethyl-6H-furo[2,3-e]indol-7-one mp: 185°–187° C.

IR(KBr): 3161, 3021, 2928, 1693, 1642, 1478, 1454, 1427, 1377, 1277, 1231, 1091, 1054, 967 cm$^{-1}$.

$^1$H-NMR(CDCl$_3$) δ: 1.43(6H, s), 1.61(3H, s), 2.19(3H, s), 2.95(1H, d, J=15.6 Hz), 3.25(1H, d, J=15.6 Hz), 3.51(2H, s), 6.78(1H, s).

(7) 2-Azidomethyl-2,3,7,8-tetrahydro-2,5,8,8-tetramethyl-6H-furo[2,3-e]indol-7-one Yield: quantitative mp: 176°–178° C.

IR(KBr): 3136, 2957, 2853, 2083, 1693, 1634, 1443, 1376, 1298, 1096, 968, 885 cm$^{-1}$.

$^1$H-NMR(CDCl$_3$) δ: 1.43(3H, s), 1.44(3H, s), 1.48(3H, s), 2.17(3H, s), 2.86(1H, d, J=15.1 Hz), 3.14(1H, d, J=13.1 Hz), 3.41(1H, d, J=13.1 Hz), 6.79(1H, s).

(8) 2-Aminomethyl-2,3,7,8-tetrahydro-2,5,8,8-tetramethyl-6H-furo[2,3-e]indol-7-one·hydrochloride Yield (free base): 82% mp: >300° C.

IR(KBr): 3382, 3133, 2899, 1677, 1644, 1508, 1477, 1381, 1315, 1268, 1162, 1085, 1044, 964 cm$^{-1}$.

$^1$H-NMR(CD$_3$OD) δ: 1.37(3H, s), 1.41(3H, s), 1.51(3H, s), 2.17(3H, s), 2.99(1H, d, J=15.6 Hz), 3.13(1H, d, J=15.6 Hz), 3.24–3.34(2H, m), 6.86(1H, s).

Example 3

The following compounds were prepared in the same manner as in Examples 1 (5)–(8).

(1) 4-(2-Butenyl)oxy-2,3-dihydro-3,3,7-trimethyl-1H-indol-2-one

Yield: 40% mp: 178°–180° C.

IR(KBr): 3130, 3019, 2899, 1683, 1599, 1496, 1447, 1423, 1372, 1313, 1243, 1190, 1161, 1063, 961 cm$^{-1}$.

$^1$H-NMR(CDCl$_3$) δ: 1.47(6H, s), 1.74–1.77(3H, m), 2.18(3H, s), 4.46–4.59(2H, m), 5.63–5.87(2H, m), 6.47(1H, d, J=8.3 Hz), 6.92(1H, d, J=8.3 Hz).

(2) 2,3-Dihydro-4-hydroxy-5-(1-methyl-2-propenyl)-3,3,7-trimethyl-1H-indol-2-one Yield: 92%

IR(KBr): 3440, 3203, 2958, 1682, 1627, 1482, 1453, 1378, 1272, 1228, 1184, 1105, 881 cm$^{-1}$.

$^1$H-NMR(CDCl$_3$) δ: 1.40–1.42(3H, m), 1.48(6H, s), 2.18(3H, s), 3.48(1H, m), 5.24–5.31(2H, m), 6.11(1H, m), 6.77(1H, s).

(3) 2-Bromomethyl-2,3,7,8-tetrahydro-3,5,8,8-tetramethyl-6H-furo[2,3-e]indol-7-one Yield: 80% mp: 183°–184° C.

IR(KBr): 3170, 2957, 1640, 1476, 1454, 1378, 1310, 1249, 1216, 1160, 1097, 1037, 968 cm$^{-1}$.

$^1$H-NMR(CDCl$_3$) δ: 1.24–1.26, 1.35–1.38(m, 3H, altogether), 1.43(3H, s), 1.44(3H, s), 2.17(3H, s), 3.27–3.61(3H, m), 4.73(1H, m), 6.76(1H, s).

(4) 2-Azidomethyl-2,3,7,8-tetrahydro-3,5,8,8-tetramethyl-6H-furo[2,3-e]indol-7-one Yield: quantitative mp: 200°–202° C.

IR(KBr): 3131, 2919, 1684, 1620, 1473, 1448, 1427, 1308, 1250, 1210, 1105, 1043, 924 cm$^{-1}$.

$^1$H-NMR(CDCl$_3$) δ: 1.22–1.24, 1.31–1.34(m, 3H, altogether), 1.45(6H, s), 2.18(3H, s), 3.21–3.62(3H, m), 4.71(1H, m), 6.76(1H, s).

(5) (2R*,3R*)-2-aminomethyl-2,3,7,8-tetrahydro-3,5,8,8-tetramethyl-6H-furo[2,3-e]indol-7-one•hydrochloride (a) and (2R*,3S*)-2-aminomethyl-2,3,7,8-tetrahydro-3,5,8,8-tetramethyl-6H-furo[2,3-e]indol-7-one•hydrochloride (b)

3.4 g (11.3 mmol) of 2-azidomethyl-2,3,7,8-tetrahydro-3,5,8,8-tetramethyl-6H-furo[2,3-e]indol-7-one was dissolved in 50 ml of tetrahydrofuran, and 1.7 g of 10% palladium-carbon catalyst was added to the solution. The mixture was stirred for 6 hours at room temperature under a hydrogen atmosphere. The catalyst was removed by filtration and the filtrate was concentrated. The residue obtained was purified by column chromatography (silica gel, 300:10:1 mixture of chloroform, methanol, and water) and recrystallized (chloroform-n-hexane) to obtain 900 mg of a free base of compound (a) as a former component and 410 mg of a free base of compound (b) as a latter component. These free bases were made into hydrochlorides and recrystallized (methanol-ether) to obtain the title stereo isomers (a) and (b), both as colorless crystals.

Compound (a)

mp: 292°–294° C.

IR(KBr): 3411, 3176, 2955, 1692, 1641, 1506, 1480, 1451, 1304, 1247, 1089, 977, 751 cm$^{-1}$.

$^1$H-NMR(CD$_3$OD) δ: 1.34–1.37(3H, m), 1.38(3H, s), 1.41(3H, s), 2.18(3H, s), 3.16–3.67(3H, m), 4.47(1H, m), 6.84(1H, s).

Compound (b)

mp: >250° C.

IR(KBr): 3408, 3175, 2951, 1698, 1644, 1616, 1505, 1479, 1453, 1423, 1300, 1263, 1211, 1156, 1100, 1064, 967 cm$^{-1}$.

$^1$H-NMR(CD$_3$OD) δ: 1.18–1.21(3H, m), 1.39(3H, s), 1.42(3H, s), 3.21–3.65(3H, m), 4.89(1H, m), 6.86(1H, s).

Example 4

The following compounds were prepared in the same manner as in Examples 1 (7)–(8).

(1) 2-Bromomethyl-2,3,5,8,8-pentamethyl-2,3,7,8-tetrahydro-6H-furo[2,3-e]indol-7-one Yield: 99.7%, Diastereomer ratio, 1:1 mp: 190°–192° C.

IR(KBr): 3396, 3161, 2930, 2920, 1704, 1641, 1475, 1452, 1378, 1311, 1272, 1163, 1089, 1058, 883, 839, 762, 745, 634 cm$^{-1}$.

$^1$H-NMR(CDCl$_3$) δ: 1.27(d, J=7.3 Hz) 1.32(d, J=7.3 Hz) (3H, altogether), 1.46(s) 1.47(s) (3H, altogether), 1.48(s) 1.49(s) (3H, altogether), 1.50(s) 1.51(s) (3H, altogether), 2.23(s) 2.24(s) (3H, altogether), 3.09(q, J=7.3 Hz), 3.60–3.32(m) (3H, altogether), 6.73(s) 6.78(s) (1H, altogether), 8.69(1H, br).

(2) 2-Azidomethyl-2,3,5,8,8-pentamethyl-2,3,7,8-tetrahydro-6H-furo[2,3-e]indol-7-one Yield: 64.7%, Diastereomer ratio, 1:1 mp: 188°–191° C.

IR(KBr): 3381, 3161, 3061, 2970, 2922, 2093, 1702, 1640, 1475, 1431, 1378, 1310, 1270, 1092, 1061, 763, 750 cm$^{-1}$.

$^1$H-NMR(CDCl$_3$) δ: 1.26(d, J=6.8 Hz) 1.29(d, J=6.8 Hz) (3H, altogether), 1.43(s) 1.44(s) (3H, altogether), 1.46(s) 1.47(s) (3H, altogether), 1.48(s) 1.51(s) (3H, altogether), 3.06(q, J=6.8 Hz) 3.22(q, J=6.8 Hz) (1H, altogether), 3.21(d, J=12.7 Hz) 3.32(d, J=12.7 Hz) (1H, altogether), 3.41(d, J=12.7 Hz) 3.51(d, J=12.7 Hz) (1H, altogether), 6.72(s) 6.74(s) (1H, altogether), 8.22(br.) 8.36(br.) (1H, altogether).

(3) (2R*,3R*)-2-aminomethyl-2,3,5,8,8-pentamethyl-2,3,7,8-tetrahydro-6H-furo[2,3-e]indol-7-one•hydrochloride 3.10 g (10.8 mmol) of 2-azidomethyl-2,3,5,8,8-pentamethyl-2,3,7,8-tetrahydro-6H-furo[2,3-e]indol-7-one was dissolved in 100 ml of N,N-dimethylformamide, and 3.10 g of 10% palladium-carbon catalyst was added to the solution. The mixture was stirred for 8 hours at room temperature under a hydrogen atmosphere. The catalyst was removed from the reaction mixture by filtration and the filtrate was concentrated under reduced pressure. The residue obtained was separated and purified by column chromatography (silica gel, benzene:methanol=30:1→benzene:methanol=20:1→benzene:methanol=10:1) to obtain crude crystals of (2R*,3R*)-2-aminomethyl-2,3,5,8,8-pentamethyl-2,3,7,8-tetrahydro-6H-furo[2,3-e]indol-7-one. The crystals were made into hydrochloride and recrystallized from methanolether to obtain 364.5 mg (yield: 10.8%) of colorless crystals of the title compound.

mp: >300° C.

IR(KBr): 3409, 3128, 2989, 1698, 1680, 1642, 1609, 1479, 1452, 1378, 1315, 1267, 1171, 1101, 1080, 1055, 1023, 993, 845, 753, 634 cm$^{-1}$.

$^1$H-NMR(CD$_3$OD) δ: 1.26(3H, d, J=7.8 Hz), 1.34(3H, s), 1.37(3H, s), 1.40(3H, s), 2.18(3H, s), 3.23(2H, s), 3.26(1H, q, J=7.8 Hz), 6.83(1H, s).

Example 5

2,3-Dihydro-5-(1,2-dimethyl-2-propenyl)-4-hydroxy-3,3,7-trimethyl-1H-indol-2-one (1) and 2,2,3,5,8,8-hexamethyl-2,3,7,8-tetrahydro-6H-furo[2,3-e]indol-7-one (2)

N,N-dimethylaniline (22 ml) was added to 21.76 g of 2,3-dihydro-4-(3-methyl-2-butenyloxy)-3,3,7-trimethyl-1H-indol-2-one, and the mixture was stirred for 5 hours at 210° C. After cooling, the reaction mixture was dissolved in ethyl acetate, washed with 2N hydrochloric acid and saturated brine, and dried over anhydrous sodium sulfate. The solvent was removed by evaporation to obtain 23.68 g of a brown oily product. This product was purified by column chromatography (silica gel, 2:1 mixture of chloroform and n-hexane) and recrystallized from n-hexane to obtain 14.4 g (yield, 70.5%) the title compound (1). The mother liquor obtained from the recrystallization was again purified by column chromatography (silica gel, 2:1 mixture of chloroform and n-hexane) to obtain 1.98 g (yield, 9.0%) the title compound (2).

Title compound (2)

mp: >213°–216° C.

IR(KBr): 3196, 1698, 1646, 1276, 1087, 850 cm$^{-1}$.

$^1$H-NMR(CDCl$_3$) δ: 1.19(3H, d, J=7.1 Hz), 1.24(3H, s), 1.43(3H, s), 1.43(3H, s), 1.46(3H, s), 2.18(3H, s), 3.51(1H, m), 6.71(1H, s), 7.91(1H, br. s).

Example 6

(1) 2,3-Dihydro-4-prenyloxy-3,3,7-trimethyl-1H-indol-2-one 4.0 g (22.1 mmol) of 2,3-dihydro-4-hydroxy-3,3,7-trimethyl-1H-indol-2-one was dissolved in 44 ml of N,N-dimethylformamide. After the addition of 3.42 g (22.9 mmol), of prenyl bromide and 6.1 g (44.2 mmol) of potassium carbonate, the mixture was heated with stirring over a water bath at 70° C. The addition of prenyl bromide and potassium carbonate was repeated, in amounts of 2.3 g (15.3 mmol) and 0.6 g (4.35 mmol), after one hour, and 1.65 g (11.1 mmol) and 0.6 g (4.35 mmol), after two hours, respectively. Then, the mixture was stirred for a further 2.5 hours. After the addition of 1 of chloroform, the resulting reaction mixture was washed with water, three times, dried over anhydrous sodium sulfate, and concentrated under reduced pressure. The residue obtained was recrystallized (ether-n-hexane) to obtain 4.12 g (yield, 72.0%) of colorless needles of the title compound. mp: 169°–171° C.

IR(KBr): 1708, 1609, 1505, 1273, 1254, 1095, 1075, 789 cm$^{-1}$.

$^1$H-NMR(CDCl$_3$) δ: 1.46(6H, s), 1.73(3H, s), 1.79(3H, s), 2.21 (3H, s), 4.52(2H, d, J=6.4 Hz), 5.46(1H, t, J=6.4 Hz), 6.49(1H, d, J=8.8 Hz), 6.93(1H, d, J=8.8 Hz), 8.18(1H, br.).

(2) 2,3-Dihydro-5-(1,2-dimethyl-2-propenyl)-4-hydroxy-3,3,7-trimethyl-1H-indol-2-one 4.08 g (15.8 mmol) of 2,3-dihydro-4-prenyloxy-3,3,7-trimethyl-1H-indol-2-one was added to 12.3 ml of N,N-dimethylaniline, and the mixture was heated with stirring at 205° C. for 14 hours under an argon atmosphere. After the reaction, N,N-dimethylaniline was evaporated under reduced pressure. The residue was dissolved in chloroform, washed with water, 2N hydrochloric acid, and saturated brine, dried over anhydrous sodium sulfate, and concentrated under reduced pressure. The residue obtained was purified by column chromatography (silica gel, 10:1 mixture of chloroform and ethyl acetate) to obtain 4.08 g (yield, quantitative) of a light brown powder of the title compound.

IR(KBr): 3441, 3168, 2960, 1696, 1628, 1479, 1452, 1374, 1272, 1235, 754 cm$^{-1}$.

$^1$H-NMR(CDCl$_3$) δ: 1.43(3H, d, J=6.8 Hz), 1.46(3H, s), 1.47(3H, s), 1.67(3H, s), 2.20(3H, 3.43(1H, q, J=6.8 Hz ), 5.07(1H, s), 5.15(1H, s), 5.61(1H, s), 6.76(1H, s), 8.19(1H, br. s).

(2R* ,3S*)-2-iodomethyl-2,3,5,8,8-pentamethyl-2,3,7,8-tetrahydro-6H-furo[2,3 -e]indol-7-one 4.08 g (15.8 mmol) of 2,3-dihydro-5-(1,2-dimethyl-2propenyl)-4-hydroxy-3,3,7-trimethyl- 1H-indol-2-one was dissolved in 60 ml of a 4:1 mixed solvent of chloroform and methanol. To the solution was added 3.23 g (23.4 mmol) of potassium carbonate, while stirring at −20° C., a solution of 4.40 g (17.3 mmol) of iodide and 2.90 g (17.5 mmol) of potassium iodide dissolved in 300 ml of a 4:1 mixture of chloroform and methanol, which was cooled to −20° C.

After further stirring at −22° C. for 12 hours, an aqueous solution of sodium hydrogen sulfite was added and the mixture was stirred at room temperature to reduce excessive iodine. The reaction mixture was extracted with chloroform, and the extract was dried over anhydrous sodium sulfate and concentrated under reduced pressure. The residue was recrystallized from ethyl acetate to obtain 5.02 g (yield, 82.5%) of colorless prisms of the title compound.

mp: 212°–214° C.

IR(KBr): 3175, 2957, 1695, 1642, 1474, 1450, 1430, 1378, 1267, 1158, 1096, 1055 cm$^{-1}$.

$^1$H-NMR(CDCl$_3$) δ: 1.29(3H, d, J=7.3 Hz), 1.45(3H, s), 1.51(3H, s), 1.63(3H, s), 2.19(3H, s), 3.25(1H, d, J=10.3 Hz), 3.35(1H, q, J=7.3 Hz), 3.44(1H, d, J=10.3 Hz), 6.70(1H, s), 7.93(1H, br. s).

(4) (2R*,3S* )-2-azidomethyl-2,3,5,8,8-pentamethyl-2,3,7, 8-tetrahydro-6 H-furo[2,3-e]indol-7-one 70 ml of N,N-dimethylformamide was added to a mixture of 5.02 g (13.0 mmol) of (2R*,3S*)-2-iodomethyl-2,3,5,8, 8-pentamethyl-2,3,7,8-tetrahydro-6 H-furo[2,3-e]indol-7-one and 10.0 (154 mmol) of sodium azide. The mixture was heated with stirring for 2 hours at 150° C. After cooling, the solvent was evaporated under reduced pressure. Chloroform was added to the residue, and the mixture was washed with water and saturated brine, dried over anhydrous sodium sulfate, and concentrated under reduced pressure. The residue obtained was purified by column chromatography (silica gel, 10:1 mixture of chloroform and ethyl acetate) to obtain 2.67 g (yield, 68.7%) of colorless crystals of the title compound.

mp: 206°–208° C.

IR(KBr): 3162, 2980, 2091, 1696, 1637, 1479, 1454, 1431, 1300, 1259, 1095 cm$^{-1}$.

$^1$H-NMR(CDCl$_3$) δ: 1.26(3H, d, J=6.8 Hz), 1.44(3H, s), 1.47(3H, s), 1.51(3H, s), 2.19(3H, s), 3.21(1H, d, J=12.7 Hz), 3.22(1H, q, J=6.8 Hz), 3.51(1H, d, J=12.7 Hz), 6.72(1H, s), 7.87(1H, br. s).

(5) (2R*,3S*)-2-aminomethyl-2,3,5,8,8-pentamethyl-2,3,7, 8-tetrahydro-6H-furo[2,3 -e]indol-7-one•hydrochloride 2.67 g (8.93 mmol) of (2R*,3S*) 2-aminomethyl-2,3,5, 8,8-pentamethyl-2,3,7,8 -tetrahydro-6H-furo[2,3-e]-indol-7-one was dissolved in 230 ml tetrahydrofuran. After the addition of 2.7 g of 10% palladium-carbon catalyst, the solution was stirred for 1 hour at room temperature under a hydrogen atmosphere. The catalyst was removed by filtration, and the residue was concentrated and made into hydrochloride. The hydrochloride was dissolved in water, washed with chloroform, weakly alkalinized with 2N aqueous solution of hydroxide, extracted with chloroform, dried over anhydrous sodium sulfate, and concentrated under reduced pressure to obtain colorless crystals. The crystals were converted into hydrochloride and recrystallized from methanol-ether to obtain 2.11 g (yield, 76.1%) of colorless prisms of the title compound.

mp: >200° C.

IR(KBr): 3393, 3146, 2957, 2860, 1689, 1642, 1506, 1479, 1453, 1264, 1098, 1057 cm$^{-1}$.

$^1$H-NMR(CD$_3$OD) δ: 1.26(3H, d, J=6.8 Hz ), 1.39(3H, s), 1.42(3H, s), 1.56(3H, s), 2.19(3H, s), 3.13(2H, s), 3.32(1H, q, J=6.8 Hz), 6.83(1H, s).

Example 7

(1) 4-(1-cis-2-pentenyloxy)-2,3-dihydro-3,3,7-trimethyl-1H-indol-2-one 2 g (10.4 mol) of 2,3-dihydro-4-hydroxy-3,3,7-trimethyl-1H-indol-2-one was dissolved in 20 ml of N,N-dimethylformamide. To the solution were added 1.89 g (20.9 mmol) of 1-bromo-2-pentene and 2.89 g (12.0 mmol) of potassium carbonate, and the mixture was stirred for 3 hours at 70° C. After cooling, chloroform and water was added to the reaction mixture for phase separation. The organic layer was washed with water and saturated brine, dried over anhydrous sodium sulfate, and concentrated under reduced pressure. The residue was recrystallized from ethyl acetate-n-hexane to obtain 1.41 g (yield, 52%) of colorless needles of the title compound.

mp: 135°–139° C.

$^1$H-NMR(CDCl$_3$) δ: 1.02(3H, t, J=7.3 Hz), 1.46(6H, s), 2.12–2.20 (2H, m), 2.19(3H, s), 4.57–4.65(2H, m), 5.62–5.66 (2H, m), 6.49(1H, d, J=8.3 Hz), 6.93(1H, d, J=8.3 Hz), 7.92(1H, br. s).

(2) 2-(t-butyldimethylsilyloxymethyl)-3-ethyl-2,3,7,8-tetrahydro-5,8,8-trimethyl- 6H-furo[2,3-e]indol-7-one (1) and 2-(1-hydroxyethyl)-2,3,7,8-tetrahydro-3,5,8,8-tetramethyl-6H-furo[2,3-e] indol-7-one (2)

5 ml of N,N-dimethylaniline was added to 2 g (7.71 mmol) of 4-(1-cis-2-pentenyloxy)-2,3-dihydro-3,3,7-trimethyl-1H-indol-2-one, and the mixture was stirred for 5 hours at 203° C. under an argon atmosphere. After cooling, chloroform was added to the reaction mixture, followed by extraction with the addition of 3N sodium hydroxide aqueous solution. The water layer was adjusted to pH 2 with 6N hydrochloric acid, followed by extraction with chloroform. The organic layer was washed with saturated brine, dried over anhydrous sodium sulfate, and concentrated under reduced pressure to obtain 1.35 g of a rearranged compound, which was used as is for the next reaction.

The 1.35 g of the rearranged compound was dissolved in 5 ml of pyridine and 865 mg (8.48 mmol) of acetic anhydride was added under cooling with ice, followed by stirring for 1.5 hours at room temperature. The reaction mixture was concentrated under reduced pressure, ethyl acetate was added to the residue. The mixture was washed with saturated aqueous solution of potassium hydrogen sulfate, saturated aqueous solution of sodium hydrogen carbonate, and saturated brine, dried over anhydrous sodium sulfate, and concentrated under reduced pressure, thus obtaining 1.57 g of an acetyl compound, which was used as is for the next reaction.

The 1.57 g of the acetyl compound was dissolved in 25 ml of chloroform, 4 g (15.53 mmol) of m-chlorobenzoate was added to the solution, and the mixture was stirred for 3.5 hours at room temperature. The reaction mixture was filtered and the filtrate was washed with saturated aqueous solution of sodium sulfite, saturated aqueous solution of sodium hydrogen carbonate, and saturated brine, dried over anhydrous sodium sulfate, and concentrated under reduced pressure. The residue was dissolved in 10 ml of methanol, 7 ml of 1N aqueous solution of sodium hydroxide was added to the solution, and the mixture was stirred for 1.5 hours at 50° C. After cooling, ethyl acetate and water was added to the reaction mixture, followed by extraction with ethyl acetate. The organic layer was washed with water and saturated brine, dried over anhydrous sodium sulfate, and concentrated under reduced pressure to obtain 780 mg of a cyclized compound.

350 mg of the cyclized compound was dissolved in 4 ml of N,N-dimethylformamide, and 130 mg (1.89 mmol) of imidazole and 145 mg (0.96 mmol) of t-butyldimethylsilyl chloride were added to the solution under cooling with ice. The mixture was stirred for 1.5 hours under cooling with ice. Ethyl acetate-water was added to the reaction mixture, followed by extraction with ethyl acetate. The organic layer was washed with saturated aqueous solution of potassium hydrogen sulfate and saturated brine, dried over anhydrous sodium sulfate, and concentrated under reduced pressure. The residue was submitted to column chromatography (silica gel, 1:1 mixture of ethyl acetate and n-hexane) to obtain 244 mg (yield: 18%) of silyl compound (1) and 213 mg (yield: 22%) of hydroxy compound (2), each as and oil.

Title compound (1)

IR(CHCl$_3$): 2922, 1704, 1640, 1456 cm$^{-1}$.

$^1$H-NMR(CDCl$_3$) δ: 0.04(s) 0.08(s) 0.10(s) 0.11(s) (6H, altogether), 0.87(s) 0.89(s) (9H, altogether), 0.99(t, J=7.3 Hz), 1.00(t, J=7.3 Hz) (3H, altogether), 1.43(s) 1.44(s) (6H, altogether), 1.48–1.78(2H, m), 2.19(3H, s), 3.10(1H, m), 3.71(dq, J=5.3, 10.7 Hz) 3.94(m) (2H, altogether), 4.48(q, J=5.3 Hz) 4.72(m) (1H, altogether), 6.78(s) 6.80(s) (1H, altogether), 8.09(1H, br. s).

MS(m/z): 389(M$^+$).

Title compound (2)

$^1$H-NMR(CDCl$_3$) δ: 1.26(3H, t, J=6.8Hz), 1.35(d, J=6.8 Hz) 1.36 altogether), 1.44(s) 1.45(s) (d, J=5.8 Hz) (3H, altogether), 1.44(s) 1.45(s) (3H, altogether), 2.17(3H, s), 3.39(quintet, J=6.8 Hz) 3.49(quintet, J=7.8 Hz) (1H, altogether), 4.09(1H, m), 4.25(dd, J=3.9, 6.8 Hz) 4.43(t, J=7.8 Hz) (1H, altogether), 6.76(s) 6.77(s) (1H, altogether), 7.77(1H, br. s).

(3) 3-Ethyl-2-hydroxymethyl-2,3,7,8-tetrahydro-5,8,8-trimethyl-6H-furo[2,3 -e]indol-7-one 228 mg (0.585 mmol) of 2-(t-butyldimethylsilyloxymethyl)-3-ethyl-2,3,7,8-tetrahydro-5,8,8 -trimethyl-6H-furo[2,3-e]indol-7-one was dissolved in 6 ml of methanol, 0.6 ml of 1N hydrochloric acid was added to the solution, and the mixture was stirred for 2 hours at room temperature. Ethyl acetate-water was added to the reaction mixture, followed by extraction with ethyl acetate. The organic layer was washed with water and saturated brine, dried over anhydrous sodium sulfate, and concentrated under reduced pressure, to obtain 161 mg (yield: quantitative) of the title compound as an oil.

IR(CHCl$_3$): 2922, 1703, 1640, 1456 cm$^{-1}$.

$^1$H-NMR(CDCl$_3$) δ: 1.00(t, J=7.3 Hz) 1.06(t, J=7.3 Hz) (3H, altogether), 1.44(s) 1.45(s) (6H, altogether), 1.58–1.78(2H, m), 2.19(3H, s), 3.02(m) 3.28(m) (1H, altogether), 3.65–3.88(2H, m), 4.56(dt, J=3.9, 5.8 Hz) 4.85(m) (1H, altogether), 6.79(s) 6.81 (s) (1H, altogether), 7.99(1H, br. s).

MS(m/z): 275(M$^+$).

(4) 3-Ethyl-2-methanesulfonyloxymethyl-2,3,7,8-tetrahydro-5,8,8-trimethyl-6H-furo[2,3 -e]indol-7-one 160 mg (0.585 mmol) of 3-ethyl-2-hydroxymethyl-2,3,7, 8-tetrahydro-5,8,8-trimethyl-6 H-furo[2,3-e]indol-7-one was dissolved in 3 ml of methylene chloride, 97 mg (1.24 mmol) of pyridine and 105 mg of methanesulfonyl chloride were added to the solution under cooling with ice, and the mixture was stirred for 14 hours at room temperature. Ethyl acetate-water was added to the reaction mixture, followed by extraction with ethyl acetate. The organic layer was washed with saturated aqueous solution of potassium hydrogen sulfate, saturated aqueous solution of sodium hydrogen carbonate, and saturated brine, dried over anhydrous sodium sulfate, and concentrated under reduced pressure, to obtain 206 mg (yield: quantitative) of a solid of the title compound.

mp: 190°–194° C. (ethyl acetate-n-hexane).

IR(CHCl$_3$): 1705, 1454, 1358 cm$^{-1}$.

$^1$H-NMR(CDCl$_3$) δ: 1.00(t, J=7.3 Hz) 1.06(t, J=7.3 Hz) (3H, altogether), 1.43(s) 1.44(s) (6H, altogether), 1.62–1.82(2H, m), 2.19(3H, s) 3.05(s) 3.10(s) (3H, altogether), 3.08(m) 3.31(q, J=7.8 Hz) (1H, altogether), 4.32–4.54(2H, m), 4.68(q, J=5.3 Hz) 4.96(dt, J=3.9, 7.8 Hz) (1H, altogether), 6.80(s) 6.82(s) (1H, altogether), 7.91(1H, br. s).

MS(m/z): 353(M⁺).

(5) 2-Azidomethyl-3-ethyl-2,3,7,8-tetrahydro-5,8,8-trimethyl-6H-furo[2,3-e]indol-7-one 186 mg (0.526 mmol) of 3-ethyl-2-methanesulfonyloxymethyl- 2,3,7,8-tetrahydro-5,8,8-trimethyl-6H-furo[2,3-e] indol-7-one was dissolved in 3 ml of N,N-dimethylformamide, 115 mg (1.59 mmol) of sodium azide was added to the solution, and the mixture was stirred for 2 hours at 150° C. After cooling, ethyl acetate-water was added to the reaction mixture, followed by extraction with ethyl acetate. The organic layer was washed with water and saturated brine, dried over anhydrous sodium sulfate, and concentrated under reduced pressure, to obtain 140 mg (yield: 88%) of a solid of the title compound.

mp: 181°–184° C. (ether).

IR(CHCl₃): 2090, 1705, 1640, 1456 cm⁻¹.

¹H-NMR(CDCl₃) δ: 0.98(t, J=7.3 Hz) 1.05(t, J=7.3 Hz) (3H, altogether), 1.45(6H, s), 1.59–1.81(2H, m), 2.20(3H, s), 3.04(m) 3.26(q, J=7.8 Hz) (1H, altogether), 3.36–3.68(2H, m), 4.62(q, J=5.3 Hz) 4.90(dt, J=3.4, 8.3 Hz) (1H, altogether), 6.80(s) 6.82(s) (1H, altogether), 8.11(1H, br. s).

MS(m/z): 300(M⁺).

(6) (2R*,3R*)-2-aminomethyl-3-ethyl-2,3,7,8-tetrahydro-5,8,8- trimethyl-6H-furo[2,3-e]indol-7-one•hydrochloride (a) and (2R*,3S*)-2-aminomethyl-3-ethyl-2,3,7,8-tetrahydro-5,8,8-trimethyl-6H-furo[ 2,3-e]indol-7-one•hydrochloride (b)

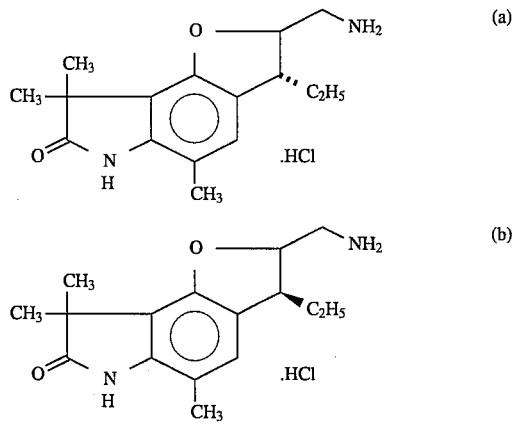

367 mg (1.22 mmol) of 2-azidomethyl-3-ethyl-2,3,7,8-tetrahydro-5,8,8-trimethyl-6 H-furo[2,3-e]indol-7-one was dissolved in 8 ml of tetrahydrofuran and 2 ml of methanol, 20 mg of 10% palladium-carbon catalyst was added to the solution, and the mixture was stirred for 14 hours at room temperature under a hydrogen atmosphere. Catalyst was removed by filtration and the filtrate was concentrated under reduced pressure. The residue was submitted to column chromatography (silica gel, 20:1 mixture of chloroform and methanol) to obtain 252 mg of free bases of title compounds (a) and (b), each as an oil.

The free bases of title compounds (a) and (b) were submitted to column chromatography (silica gel, 6:1 mixture of benzene and methanol) to obtain 136 mg of free base of compound (a) as a former component and 86 mg of free base of compound (b) as a latter component, each as an oil.

135 mg of the former component was dissolved in 4 ml of methanol, 0.7 ml of 1.37N methanol solution of hydrochloric acid was added dropwise to the solution under cooling with ice, and the mixture was stirred for 20 minutes under cooling with ice. The resulting mixture was concentrated under reduced pressure and the residue was recrystallized from methanol-ether to obtain 110 mg (yield: 29%) of the title compound (a) as colorless crystals.

The latter component was treated in the same manner and recrystallized from methanol-ether to obtain 68 mg (yield: 17%) of the title compound (b) as colorless needles.

Compound (a)

mp: above 250° C.

IR(KBr): 2917, 1705, 1645, 1466 cm⁻¹.

¹H-NMR[free base] (CDCl₃) δ: 0.99(3H, t, J=7.3 Hz), 1.44(3H, s), 1.45(3H, s), 1.40–1.82(2H, m), 2.17(3H, s), 2.83–2.96(3H, m), 4.45(1H, m), 6.78(1H, s), 7.76(1H, br. s).

Compound (b)

mp: above 250° C.

IR(KBr): 2898, 1704, 1641, 1452 cm⁻¹.

¹H-NMR[free base] (CDCl₃) δ: 1.47–1.68(2H, m), 2.18(3H, s), 2.92(1H, dd, J=3.4, 13.1 Hz), 3.02(1H, dd, J=7.9, 13.1 Hz), 3.22(1H, q, J=7.3 Hz), 4.70(1H, dt, J=3.9, 8.7 Hz), 6.80(1H, s), 7.65(1H, br. s).

Example 8

(1) 5-(1-Ethyl-2-propenyl)-4-hydroxy-3,3,7-trimethyl-2,3-dihydro-1H-indol-2-one (a) and 4-hydroxy-5-(1-methyl-2-butenyl)-3,3,7-trimethyl-2,3-dihydro-1H-indol-2-one (b)

9.689 g (37.4 mmol) of 4-(2-pentenyloxy-3,3,7-trimethyl-2,3-dihydro-1H-indol-2-one was stirred for 30 minutes at 240° C. under an argon atmosphere. After cooling, this compound was dissolved in 4N aqueous solution of sodium hydroxide, washed with n-hexane, acidified with concentrated hydrochloric acid, and extracted with chloroform. The extract was washed with water and dried over anhydrous magnesium sulfate, and the solvent was evaporated, to obtain 6.794 g (26.2 mmol) of a mixture of the title compounds at a 2:1 ratio (yield: 70.1%), as an oil.

Title compound (a)

¹H-NMR(CDCl₃) δ: 0.93(3H, t, J=7.3 Hz), 1.48(6H, s), 1.70–1.88 (2H, m), 2.20(3H, s), 3.11–3.24(1H, m), 5.10–5.30 (2H, m), 5.85–6.07(1H, m), 6.74(1H, s), 8.34(1H, br. s).

Colorless prisms of title compound (b), mp 160.5°–162° C. was obtained by repeated recrystallization of a portion of the mixture from a dichloromethane-n-hexane.

IR(KBr): 3453, 1701, 1632 cm⁻¹.

¹H-NMR(CDCl₃) δ: 1.38(3H, d, J=6.6 Hz), 1.48(6H, s), 1.75(3H, d, J=3.4 Hz), 2.20(3H, s), 3.33–3.50(1H, m), 5.41(1H, s), 5.54–5.74(2H, m), 6.76(1H, s), 8.27 (1H, br. s).

MS(m/z):259[M⁺]

(2) 2-Bromomethyl-3-ethyl-5,8,8-trimethyl-2,3,7,8-tetrahydro-6H-furo[2,3-e] indol-2-one and 2-(1-bromoethyl)-3,5,8,8-tetramethyl-2,3,7,8-tetrahydro-6H-furo[2,3-e]-indol-2-one 8.315 g (32.1 mmol) of a 2:1 mixture of 5-(1-ethyl-2-propenyl)-4-hydroxy-3,3,7-trimethyl- 2,3-dihydro-1H-indol-2-one and 4-hydroxy-5-(1-methyl-2-butenyl)-3,3,7-trimethyl-2,3-dihydro-1H-indol-2-one was dissolved in 250 ml of chloroform, 6.00 g (33.7 mmol) of N-bromosuccinimide was added to the solution, and the mixture was heated with refluxing while stirring for one hour. The reaction mixture was washed twice with water, dried over anhydrous magnesium sulfate, and purified by column chromatography (silica gel, chloroform), to obtain 10.05 g (29.7 mmol) of a mixture of the title compounds at a 2:1 ratio (yield: 92.6%) as a light yellow oil.

(3) 2-(Benzylaminomethyl)-3-ethyl-5,8,8-trimethyl-2,3,7,8-tetrahydro-6H-furo[2,3-e]indol-7-one 31.83 g (0.297 mmol) of benzylamine was added to 10.052 g (29.7 mmol) of the 2:1 mixture of 2-bromomethyl-3-ethyl-5,8,8-trimethyl-2,3,7,8-tetrahydro-6 H-furo[2,3-e] indol-2-one and 2-(1-bromoethyl)-3,5,8,8-tetramethyl-2,3,7, 8-tetrahydro-6H-furo[2,3-e]indol-2-one. The mixture was stirred for 12 hours over a water bath at 70° C. under an argon atmosphere. water was added to the reaction mixture, followed by extraction with chloroform. The extract was washed twice with water, dried over anhydrousmagnesium sulfate, and submitted to column chromatography (silica gel, 1:1 mixture of n-hexane and ethyl acetate), to obtain 3.320 g (9.8 mmol) of a first fraction containing the raw material 2-(1-bromoethyl)-3,5,8,8-tetramethyl-2,3,7,8 -tetrahydro-6H-furo[2,3-e]indol-2-one, as a major component (recovery rate, 33%), and 2.184 g (5.99 mmol) of the title compound as a second fraction (yield, 20.1%). This compound was recrystallized from ethyl acetate as light yellow prisms.

mp 143°–145° C.

IR(KBr): 3176, 2969, 1702, 1644, 1454, 1257, 1079, 734, 698, 641 cm$^{-1}$.

$^1$H-NMR(CDCl$_3$) δ: 0.98(3H, t), 1.44(3H, s), 1.46(3H, s), 1.65(2H, quint, J=7.3 Hz), 2.21(3H, s), 2.74–2.89 (2H, m), 2.90–3.04(1H, m), 3.88(2H, dd, J=13.2, 16.1 Hz), 4.55–4.70(1H, m), 6.79(1H, s), 7.18–7.45 (5H, m), 8.34(1H, s).

MS(m/z): 364[M$^+$]

IR(KBr): 3170, 1701, 1643, 1453, 1266, 1102, 698 cm$^{-1}$.

$^1$H-NMR(CDCl$_3$) δ: 1.01(1H, t, J=7.3 Hz), 1.42(3H, s), 1.43(3H, s), 1.58(2H, q, J=7.3 Hz), 2.20(3H, s), 2.83(1H, dd, J=3.4, 12.5 Hz), 2.96(1H, dd, J=9.8, 12.5 Hz), 3.20 (1H, q, J=7.3 Hz), 3.88(2H, s), 4.90(1H, td, J=3.4, 8.8 Hz), 6.79(1H, s), 7.20–7.41(5H, m), 8.03(1H, br. s).

As a third fraction, 2.337 g (64.1 mmol) of the title compound (latter component) was obtained (yield, 21.6%). This compound was recrystallized from ethyl acetate as light yellow prisms.

mp 163°–164° C.

(4) 2-(Benzylaminomethyl)-3-ethyl-5,8,8-trimethyl-2,3,7,8-tetrahydro-6H-furo[2,3-e] indol-7-one•hydrochloride (former component)

3 ml (12.0 mmol as hydrochloric acid) of 4N hydrochloric acid solution in ethyl acetate was added to 40 ml of a methanol solution of 1.896 g (5.2 mmol) of 2-(benzylaminomethyl)-3-ethyl-5,8,8 -trimethyl-2,3,7,8-tetrahydro-6H-furo[2,3-e]indol-7-one (former component). The solvent was evaporated under reduced pressure and the residue was crystallized from ethanol to obtain 1.887 g (4.71 mmol) of colorless crystals of the title compound.

Yield: 90.5% mp: 275°–278° C. (Decomposed)

IR(KBr): 2963, 2820–2300, 1712, 1644, 1457, 1264, 1241, 1102, 1065, 929, 748, 696, 640 cm$^{-1}$.

$^1$H-NMR(CD$_3$OD) δ: 0.96(3H, t, J=7.6 Hz), 1.38(3H, s), 1.39(3H, s), 1.60–1.86(2H, m), 2.18(3H, s), 3.06(1H, q, J=7.1 Hz), 3.22–3.36(2H, m), 4.35(2H, s), 4.70–4.80 (1H, m), 6.87(1H, s), 7.44–7.56(5H, m).

(5) 2-(Aminomethyl)-3-ethyl-5,8,8-trimethyl-2,3,7,8-tetrahydro-6H-furo[2,3-e] indol-7-one•hydrochloride (former component)

1.852 g (4.62 mmol) of 2-(benzylaminomethyl)-3-ethyl5, 8,8-trimethyl-2,3,7,8-tetrahydro- 6H-furo[2,3-e]indol-7-one•hydrochloride (former component) was dissolved in a mixture of 100 ml of water and 40 ml of ethanol. After the addition of 0.380 g of 10% palladium-carbon catalyst, the mixture was vigorously stirred for one hour at 70° C. under a hydrogen stream. The catalyst was removed by filtration, the solvent was evaporated, and the residue was recrystallized from ethanol to obtain 1.097 g (3.53 mmol) of colorless prisms of the title compound (yield, 76.4%).

mp: 295°–298° C. (Decomposed). IR(KBr): 3300–2500, 1709, 1650, 1469, 1261, 1069, 996, 947, 646 cm$^{-1}$.

$^1$H-NMR(CD$_3$OD) δ: 0.99(3H, t, J=7.6 Hz), 1.39(3H, s), 1.43(3H, s), 1.58–1.89(2H, m), 2.19(3H, s), 3.08(1H, q, J=6.4 Hz), 3.14(1H, dd, J=9.5, 13.4 Hz), 3.24(1H, dd, J=3.2, 13.4 Hz), 4.63–4.70(1H, m), 6.88(1H, s).

(6) 2-(Benzylaminomethyl)-3-ethyl-5,8,8-trimethyl-2,3,7,8-tetrahydro-6H-furo[ 2,3-e]indol-7-one•hydrochloride (latter component)

3 ml (12.0 mmol as hydrochloric acid) of 4N hydrochloric acid solution in ethyl acetate was added to 40 ml of a methanol solution of 2.363 g (6.48 mmol) of 2-(benzylaminomethyl)-3-ethyl- 5,8,8-trimethyl-2,3,7,8-tetrahydro-6H-furo[2,3-e]indol-7-one (latter component). The solvent was evaporated under reduced pressure and the residue was recrystallized from ethanol to obtain 2.256 g (5.63 mmol) of colorless needles of the title compound (yield, 86.8% ).

mp: 270°–273° C. (Decomposed).

IR(KBr): 2840–2350, 1705, 1690, 1649, 1455, 1269, 1253, 1230, 1103, 1060, 1001, 825, 758, 699, 639 cm$^{-1}$.

$^1$H-NMR(CD$_3$OD) δ: 0.98(3H, t, J=7.3 Hz), 1.39(6H, s), 1.42–1.68 (2H, m), 2.19(3H, s), 3.24–3.33(1H, m), 3.43(1H, dd, J=10.5, 13.4 Hz), 3.52(1H, dd, J=2.5, 13.4 Hz), 4.38(2H, s), 4.93–5.02(1H, m), 6.90(1H, s), 7.43–7.59(5H, m).

(7) 2-(Aminomethyl)-3-ethyl-5,8,8-trimethyl-2,3,7,8-tetrahydro-6H-furo[2,3-e] indol-7-one•hydrochloride (latter component)

2.150 g (5.36 mmol) of 2-(benzylaminomethyl)-3-ethyl-5,8,8-trimethyl-2,3,7,8 -tetrahydro-6H-furo[2,3-e]indol-7-one•hydrochloride (latter component) was dissolved in a mixture of 250 ml of water and 25 ml of ethanol. After the addition of 0.400 g of 10% palladium-carbon catalyst, the mixture was vigorously stirred for one hour at 70° C. under a hydrogen stream. The catalyst was removed by filtration, the solvent was evaporated, and the residue was recrystallized from ethanol to obtain 1.223 g (3.93 mmol) of colorless prisms of the title compound (yield, 73.3%).

mp: 280°–283° C. (Decomposed).

IR(KBr): 3120–2500, 1697, 1651, 1620, 1519, 1477, 1456, 1308, 1267, 1252, 1105, 756, 635 cm$^{-1}$.

$^1$H-NMR(CD$_3$OD) δ: 1.02(3H, t, J=7.3 Hz), 1.39(3H, s), 1.42(3H, s), 1.46–1.68(2H, m), 2.20(3H, s), 3.24–3.36(1H, m), 3.41(1H, dd, J=2.7, 13.4 Hz), 4.80–4.94(1H, m), 6.91(1H, s).

Example 9

The following compounds were prepared in the same manner as in Example 7, (4)–(5).

(1) 2-(1-methanesulfonyloxyethyl)-2,3,7,8-tetrahydro-3,5,8, 8-tetramethyl-6H-furo[ 2,3-e]indol-7-one Yield: quantitative IR(CHCl$_3$): 1706, 1641, 1453, 1371 cm$^{-1}$.

$^1$H-NMR(CHCl$_3$) δ: 1.32(d, J=7.3 Hz), 1.38(d, J=6.8 Hz), 1.43(d, J=7.3 Hz), 1.50(d, J=6.8 Hz) (6H, altogether), 1.45(6H, s), 2.19(3H, s), 2.98(s) 3.08(s) (3H, altogether), 3.43 (quintet, J=6.8 Hz) 3.58(quintet, J=7.8 Hz) (1H, altogether), 4.37(dd, J=3.9, 6.8 Hz), 4.77(dd, J=5.4, 7.8 Hz) (1H, altogether), 8.04(1H, br. s).

(2) 2-(1-azidoethyl)-2,3,7,8,-tetrahydro-3,5,8,8-tetramethyl-6H-furo[2,3-e]indol-7-one Yield: 93%

$^1$H-NMR(CDCl$_3$) δ: 1.25(d, J=7.3 Hz), 1.33(d, J=6.8 Hz), 1.38(d, J=6.8 Hz) (6H, altogether), 1.46(s) 1.48(s) (6H, altogether), 2.19(3H, s), 3.29(quintet, J=6.8 Hz), 3.41(quintet, J=6.4 Hz), (1H, altogether), 3.56(m) 3.73(quintet, J=6.4 Hz) (1H, altogether), 4.26 (dd, J=5.4, 6.8 Hz) 4.56 (dd, J=6.4, 8.3 Hz ) (1H, altogether), 6.77(1H, s), 7.83(1H, br. s).

(3) 2-(1-aminoethyl)-2,3,7,8-tetrahydro-3,5,8,8-tetramethyl- 6H-furo[2,3-e]indol-7-one•hydrochloride 457 mg (1.52 mmol) of 2-(1-azidoethyl)-2,3,7,8-tetrahydro-3,5,8,8- tetramethyl- 6H-furo[2,3-e]indol-7-one was dissolved in 10 ml of tetrahydrofuran and 3 ml of methanol. After the addition of 270 mg of 10% palladium-carbon catalyst, the mixture was stirred for 5 hours at room temperature under a hydrogen stream. The catalyst was removed by filtration, the filtrate was concentrated under reduced pressure, and the residue was submitted to column chromatography (silica gel, 20:1 mixture of chloroform and methanol) to obtain 210 mg of a free base of the title compound as an oil.

210 mg of this free base was dissolved in 6 ml of methanol, 1.1 ml of 1.37N methanol solution of hydrochloric acid was added dropwise to the solution under cooling with ice, and the mixture was stirred for 20 minutes under cooling with ice. The resulting mixture was concentrated under reduced pressure and the residue was washed with ether to obtain 180 mg (yield: 38%) of a solid of the title compound (yield, 38%).

mp: above 300° C. (methanol-ether).

IR(KBr): 3386, 2968, 1675, 1643, 1613, 1589, 1511, 1477, 1432 cm$^{-1}$.

$^1$H-NMR(CDCl$_3$+CD$_3$OD) δ: 1.15(d, J=7.0 Hz), 1.18–1.48(12H, m), 2.21(3H, s), 3.22–3.73(2H, m), 4.27(dd, J=7.5, 8.3 Hz) 4.48(dd, J=7.0, 13.5 Hz) (1H, altogether), 6.81(s) 6.88(s) (1H, altogether).

Example 10

(1) 2-(1-Iodoethyl)-2,3,7,8-tetrahydro-3,5,8,8-tetramethyl-6H-furo[2,3-e] indol-7-one (a) and 2-(1-iodoethyl)-5-methoxymethyl-2,3,7,8-tetrahydro-3,8,8 -trimethyl-6H-furo[2,3-e]indol-7-one (b)

287 mg (1.13 mmol) of iodine was dissolved in a 4:1 chloroform-methanol solvent. To the solution were added 191 mg of potassium iodide and 4:1 chloroform-methanol solvent, followed by stirring to homogenize. This potassium iodide solution in 4:1 chloroform-methanol was added to a 4:1 chloroform-methanol solution of 259 mg (1 mmol) of 2,3-dihydro-4-hydroxy-5 -(1-methyl-2-butenyl)-3,3,7-trimethyl-1H-indol-2-one under an argon atmosphere, and the mixture was stirred for 15 hours at room temperature. After the addition of an aqueous solution of sodium hydrogen sulfite, the reaction mixture was extracted with chloroform. The extract was washed with 1N sodium hydroxide solution and water, dried over anhydrous magnesium sulfate, and the solvent was evaporated. The residue was purified by separation thin layer chromatography (silica gel, 2:1 mixture of n-hexane and ethyl acetate) to obtain, as a low polarity component, 122 mg (yield 31.7%) of light yellow crystals of the title compound (a).

mp: 174°–181° C.

IR(KBr): 3180, 2968, 2927, 1705, 1642, 1452, 1258, 1097 cm$^{-1}$.

$^1$H-NMR(CDCl$_3$) δ: 1.20(d, J=7.1 Hz) 1.39(d, J=6.8 Hz) (3H, altogether), 1.42(s) 1.43(s) 1.44(s) 1.45(s) (6H, altogether), 1.98(d, J=6.8 Hz) 2.10(d, J=6.6 Hz) (3H, altogether), 2.18(3H, s), 3.24–3.34(m) 3.37–3.49(m) (1H, altogether), 4.17 (dd, J=4.9, 7.3 Hz) 4.79(dd, J=7.1, 10.3 Hz) (1H, altogether), 4.20–4.33(1H, m), 6.76(s) 6.78(s) (1H, altogether), 7.88(1H, br. s). MS(m/z): 385(M$^+$), 258,243.

On the other hand, a high polarity component (109 mg) was again purified by separation thin layer chromatography (30:1 mixture of chloroform and methanol) to obtain 62 mg (yield 14.9%) of light yellow crystals of the title compound (b).

mp: 147°–149° C.

IR(KBr): 3176, 2965, 2926, 1700, 1646, 1451, 1266, 1099 cm$^{-1}$.

$^1$H-NMR(CDCl$_3$) δ: 1.20(d, J=7.1 Hz) 1.40(d, J=6.8 Hz) (3H, altogether), 1.42(s) 1.43(s) 1.44(s) 1.45(s) (6H, altogether), 1.98(d, J=6.8 Hz) 2.11(d, J=6.6 Hz) (3H, altogether), 3.25–3.50(1H, m), 3.39(3H, s), 4.20(dd, J=4.9, 7.2 Hz) 4.82(dd, J=6.8, 10.3 Hz) (1H, altogether) 4.21–4.32(1H, m), 4.46(2H, s), 6.77–6.79(1H, m), 7.95(1H, br. s).

MS(m/z): 414(M$^+$-1), 383, 288.

(2) 2-(1-Iodomethyl)-2,3,7,8-tetrahydro-3,5,8,8-tetramethyl-6H-furo[2,3-e]indol-7-one 95 mg (0.424 mmol) of N-iodosuccinimide was added to a solution of 100 mg (0.386 mmol) of 2,3-dihydro-4-hydroxy-5-(1-methyl-2-butenyl)- 3,3,7-trimethyl-1H-indol-2-one in 1 ml of chloroform, and the mixture was stirred for 85 minutes while refluxing under an argon atmosphere. After the addition of an aqueous solution of sodium hydrogen sulfite, the reaction mixture was extracted with chloroform. The extract was washed with 1N sodium hydroxide solution and water and dried over anhydrous magnesium sulfate. The solvent was evaporated and the residue was purified by separation thin layer chromatography (silica gel, 2:1 mixture of n-hexane and ethyl acetate) to obtain 123 mg (yield 82.8%) of light yellow crystals of the title compound.

(3) 2-(1-Bromomethyl)-2,3,7,8-tetrahydro-3,5,8,8-tetramethyl-6H-furo[ 2,3-e]indol-7-one 755 mg (4.25 mmol) of N-bromosuccinimide was added to a solution of 1.00 g (3.86 mmol) of 2,3-dihydro-4-hydroxy-5-(1-methyl-2-butenyl)-3,3,7 -trimethyl-1H-indol-2-one in 10 ml of chloroform, and the mixture was stirred for 2 hours while refluxing under an argon atmosphere. After diluting with the addition of chloroform, the reaction mixture was washed with 1N sodium hydroxide and water and dried over anhydrous magnesium sulfate. The solvent was evaporated and the residue was purified by column chromatography (silica gel, 2:1 mixture of n-hexane and ethyl acetate) to obtain 1.24 g (yield 95.1%) of colorless crystals of the title compound.

IR(KBr): 2969, 2929, 1707, 1643, 1481, 1452, 1257, 1099 cm$^{-1}$.

$^1$H-NMR(CDCl$_3$) δ: 1.23(d, J=7.1 Hz) 1.39(d, J=6.8 Hz) (3H, altogether), 1.42(s) 1.43(s) 1.44(s) 1.45(s) (6H, altogether), 1.79(d, J=6.8 Hz) 1.89(d, J=6.6 Hz) (6H, altogether), 2.19(3H, s), 3.35–3.50(1H, m), 4.09–4.30(1H, m), 4.33(dd, J=5.1, 7.5 Hz) 4.67(dd, J=7.3, 9.9 Hz) (1H, altogether), 6.77(s) 6.79 (s) (1H, altogether), 7.73(1H, br. s).

(4) 2-(1-Benzylaminomethyl)-2,3,7,8-tetrahydro-3,5,8,8-tetramethyl-6 H-furo[2,3-e]indole 792 mg (7.39 mmol) of benzylamine was added to 250 mg (0.739 mmol) of 2-(1-bromomethyl)-2,3,7,8-tetrahydro-3,5, 8,8-tetramethyl-6 H-furo[2,3-e]indol-7-one, and the mixture was heated at 177° C. for 2 hours while stirring. The reaction mixture was concentrated under reduced pressure, and water was added to the residue, followed by extraction with chloroform. The extract was washed with water and dried over anhydrous magnesium sulfate. The solvent was evaporated and the residue was purified by separation thin layer chromatography (silica gel, 1:1 mixture of n-hexane and ethyl acetate) to obtain, as a low polarity component, 26 mg (yield 9.7%) of light yellow crystals (diastereomer B).

mp: 153°–154° C.

IR(KBr): 3192, 2970, 1704, 1644, 1484, 1455, 1260, 1049 cm$^{-1}$.

$^1$H-NMR(CDCl$_3$) δ: 1.15(3H, d, J=6.4 Hz), 1.32(3H, d, J=6..8 Hz), 1.42(3H, s), 1.44(3H, s), 2.20(3H, s), 2.89(1H, q, J=6.6 Hz), 3.24(1H, q, J=6.8 Hz), 3.77 (1H, d, J=13.4 Hz), 3.97(1H, d, J=13.4 Hz), 4.22(1H, t, J=6.8 Hz), 6.74(1H, s), 7.20–7.32(5H, m), 8.46 (1H, br. s).

On the other hand, 42 mg (yield: 15.6%) of light yellow crystals (diastereomer A) was obtained as a high polarity component.

IR(KBr): 3190, 2970, 1703, 1645, 1455, 1261, 1099 cm$^{-1}$.

$^1$H-NMR(CDCl$_3$) δ: 1.10(3H, d, J=7.1 Hz) 1.22(3H, d, J=6.1 Hz), 1.43(3H, s), 1.44(3H, s), 2.18(3H, s), 3.11–3.31 (2H, m), 3.85(1H, d, J=13.2 Hz), 4.00(1H, d, J=13.2 Hz), 4.42(1H, dd, J=7.1, 9.3 Hz), 6.80(1H, s), 7.23–7.37(5H, m), 7.84(1H, br. s).

Example 11

(1) 4-Allyloxy-1-benzyl-2,3-dihydro-3,3,7-trimethyl-1H-indol-2-one

To a solution of 11.6 g (41.2 mmol) of 1-benzyl-2,3-dihydro-4-hydroxy-3,3,7-trimethyl-1H-indol-2-one and 8.6 g (62.2 mmol) of potassium carbonate in 120 ml of N,N-dimethylformamide was added 8.3 g (49.4 mmol) of allyl iodide, and the mixture was stirred overnight at 70° C. The reaction mixture was poured into ice water and extracted with ethyl acetate. The organic layer was washed with water and dried. The solvent was evaporated and the residue was purified by column chromatography (silica gel, 7:1 mixture of n-hexane and ethyl acetate) to obtain 8.9 g (yield 67.2%) of colorless needles of the title compound.

mp: 107°–108° C.

IR(KBr): 1709, 1667, 1597, 1506, 1443, 1262, 1239 cm$^{-1}$.

$^1$H-NMR(CDCl$_3$) δ: 1.45(6H, s), 2.20(3H, s), 4.56–4.59(2H, m), 5.17(2H, s), 5.29(1H, dd, J=1.5, 10.6 Hz), 5.44(1H, dd, J=1.5, 17.3 Hz), 6.06(1H, m), 6.49(1H, d, J=8.6 Hz), 6.84(1H, d, J=8.6 Hz), 7.10–7.13(2H, m), 7.21–7.33(3H, m).

MS(m/z): 321(M$^+$).

(2) 5-Allyl-1-benzyl-2,3-dihydro-4-hydroxy-3,3,7-trimethyl-1H-indol-2-one

A solution of 8.6 g (26.8 mmol) of 4-allyloxy-1-benzyl-2,3-dihydro-3,3,7-trimethyl-1H-indol-2-one in 23 ml of N,N-dimethylformamide was stirred for 12 hours at 210° C. while stirring under an argon stream. The reaction mixture was allowed to stand to cool, poured into water, washed with 10% hydrochloric acid, washed with water, and dried. The solvent was evaporated and the residue was purified by column chromatography (silica gel, 5:1 mixture of n-hexane and ethyl acetate) to obtain 8.3 g (yield, 98.7%) of colorless needles of the title compound.

mp: 161°–162° C.

IR(KBr): 3315, 1678, 1602, 1445, 1381, 1197, 1184 cm$^{-1}$.

$^1$H-NMR(CDCl$_3$) δ: 1.55(6H, s), 2.17(3H, s), 3.34(2H, d, J=6.3 Hz), 5.15(2H, s), 5.21–5.29(2H, m), 6.01(1H, m), 6.63(1H, s), 7.10–7.33(5H, m).

MS(m/z): 321(M$^+$).

(3) 4-Acetoxy-5-allyl-1-benzyl-2,3-dihydro-3,3,7-trimethyl-1H-indol-2-one 2.5 g (50.9 mmol) of acetic anhydride was added to a solution of 8.2 g (25.5 mmol) of 5-allyl-1-benzyl-2,3-dihydro-4-hydroxy-3,3,7-trimethyl-1H-indol-2-one and 250 mg (2.0 mmol) of N,N-dimethylaminopyridine in 80 ml of pyridine under cooling with ice, and the mixture was stirred overnight at room temperature. The reaction mixture was poured into ice water, washed with 10% hydrochloric acid, washed with water, and dried. The solvent was evaporated and the residue was purified by column chromatography (silica gel, 5:1 mixture of n-hexane and ethyl acetate) to obtain 8.0 g (yield, 85.2%) of colorless needles of the title compound.

IR(KBr): 3185, 1761, 1700, 1631, 1202 cm$^{-1}$.

$^1$H-NMR(CDCl$_3$) δ: 1.45(6H, s), 2.23(3H, s), 2.36(3H, s), 3.15 (2H, d, J=6.6 Hz), 5.06–5.13(2H, m), 5.16(2H, s), 5.85(1H, m), 6.80(1H, s), 7.09–7.34(5H, m). MS(m/z ): 363(M$^+$).

(4) 4-Acetoxy-1-benzyl-2,3-dihydro-5-(trans-3-methoxycarbonyl)allyl- 3,3,7-trimethyl-1H-indol-2-one (a) and 4-acetoxy-1-benzyl-2,3 -dihydro-cis-(3-methoxycarbonyl)allyl-3,3,7-trimethyl-1H-indol-2-one (b)

Ozone was bubbled through a solution of 8.2 g (22.6 mmol) of 4-acetoxy-5-allyl-1-benzyl-2,3-dihydro-3,3,7-trimethyl-1H-indol-2-one in 2 l of ethyl acetate for 3 hours under cooling with ice. After bubbling nitrogen through the reaction mixture, 34.6 g (558 mmol) of dimethylsulfide was added and the mixture was stirred for one hour at 50° C. The solvent was evaporated and the residue was dissolved in 800 ml of methanol, followed by addition of 15.7 g (47 mmol) of methyltriphenylphosphoranilidene acetate. The mixture was stirred overnight. After evaporating the solvent from the reaction mixture, the residue was purified by column chromatography (silica gel, 3:1 mixture of n-hexane and ethyl acetate) to obtain 1.5 g (yield, 15.7%) of the title compound (a) and 480 mg (yield, 5.0%) of the title compound (b), each as a light yellow oil.

Compound (a)

IR(CHCl$_3$): 3432, 1768, 1702, 1652, 1443, 1281, 1179 cm$^{-1}$.

$^1$H-NMR(CDCl$_3$) δ: 1.45(6H, s), 2.23(3H, s), 2.37(3H, s), 3.27 (2H, dd, J=1.7, 6.8 Hz), 3.74(3H, s), 5.17(2H, s), 5.84(1H, dt, J=1.7, 15.6 Hz), 6.75(2H, s), 6.98(1H, dt, J=6.8, 15.6 Hz), 7.09–7.34(5H, m).

MS(m/z): 421(M$^+$).

Compound (b)

$^1$H-NMR(CDCl$_3$) δ: 1.45(6H, s), 2.23(3H, s), 2.35(3H, s), 3.74 (3H, s), 3.81(2H, d, J=7.3 Hz), 5.16(2H, s), 5.84(1H, dt, J=11.2 Hz), 6.25(1H, dt, J=11.2 Hz), 6.83(1H, s), 7.09–7.33(5H, m).

MS(m/z ): 421(M$^+$).

(5) 1-Benzyl-2,3-dihydro-4-hydroxy-5-(4-hydroxy-2-butenyl)-3,3,7-trimethyl-1 H-indol-2-one 16.8 ml of 1M diisobutylaluminum hydride toluene solution was added to a solution of 1.5 g (3.6 mmol) of 4-acetoxy-1-benzyl-2,3 -dihydro-5-(trans-3-methoxycarbonyl)allyl-3,3,7-trimethyl-1H-indol-2-one in 11 ml of methylene chloride at −78° C. under a stream of argon, and the mixture was stirred for 1.5 hours at 0° C. The reaction mixture was diluted with 100 ml of ether and 2 ml of saturated aqueous solution of ammonium chloride was added to it, followed by stirring for 1.5 hours. The mixture was filtered through cerite and the mother liquor was concentrated. The residue was purified by column chromatography (silica gel, 2:1 mixture of n-hexane and ethyl acetate) to obtain 450 mg (yield, 37.3%) of the title compound as a light yellow oil.

$^1$H-NMR(CDCl$_3$) δ: 1.26(s) 1.37(s) (6H, altogether), 2.28(s) 2.30(s) (3H, altogether), 3.08(2H, d, J=5.1 Hz), 4.12–4.17(2H, m), 4.47(2H, s), 5.69–5.87(2H, m), 6.60(s) 6.73(s) (1H, altogether), 7.26–7.35(5H, m).

(6) 1-Benzyl-2,3,7,8-tetrahydro-5,8,8-trimethyl-2-vinyl-6H-furo[2,3-e]indol-7-one 1.27 g (8.9 mmol) of boron trifluoride diethyl ether was added to a solution of 437 mg (1.2 mmol) of 1-benzyl-2,3-dihydro-4-hydroxy-5 -(4-hydroxy-2-butenyl)-3,3,7-trimethyl-1H-indol-2-one in 11 ml of 1,2-dichloroethane under cooling with ice, and the mixture was stirred for 4 hours at 60° C. After cooling, 3 ml of saturated aqueous solution of sodium hydrogen carbonate was added and the mixture was stirred overnight at room temperature. The reaction mixture was extracted with chloroform. The extract was washed with water and dried. The, solvent was evaporated and the residue was purified by column chromatography (silica gel, 5:1 mixture of n-hexane and ethyl acetate) to obtain 100 mg (yield, 24.9%) of the title compound.

IR(CHCl$_3$): 3004, 2962, 1630, 1476, 1468, 1455, 1354 cm$^{-1}$.

$^1$H-NMR(CDCl$_3$) δ: 1.34(s) 1.35(s) (6H, altogether), 2.26(3H, s), 2.80–3.31(2H, m), 4.46(2H, s), 5.14–5.22(2H, m), 5.35(1H, dt, J=1.5, 17.1 Hz), 6.00(1H, m), 6.69(1H, s), 7.25–7.38(5H, m).

MS(m/z): 319(M$^+$).

(7) 6-Benzyl-2-(2-methanesulfonyloxy)ethyl-2,3,7,8-tetrahydro-5,8,8-trimethyl- 6H-furo[2,3-e]indol-7-one 3.0 ml of 0.5N 9-borabicyclo[3.3.1]nonane tetrahydrofuran solution was added to a solution of 98 mg (0.29 mmol) of 6-benzyl-2,3,7,8-tetrahydro-5,8,8-trimethyl-2-vinyl-6H-furo[2,3-e] indol-7-one in 2 ml of tetrahydrofuran under cooling with ice, and the mixture was stirred overnight at room temperature. Then, 0.6 ml of 3N aqueous solution of sodium hydroxide and 0.6 ml (6.2 mmol) 35% hydrogen peroxide were added and the mixture was stirred for 30 minutes at room temperature. The solvent was evaporated and the residue was purified by separation thin layer chromatography (silica gel, 2:1 mixture of n-hexane and ethyl acetate) to obtain 72 mg (yield, 73.7%) of a colorless oil of 6-benzyl-2-(2-hydroxy)ethyl-2,3,7,8-tetrahydro-5,8,8-trimethyl-6H-furo[2,3-e]indol-7 -one. To a solution of 36 mg (0.11 mmol) of this hydroxy compound in 1.5 ml of pyridine was added dropwise 13.8 mg (0.11 mmol) of methanesulfonyl chloride under cooling with ice, and the mixture was stirred for 1.5 hours at room temperature. The reaction mixture was poured into ice water and extracted with ethyl acetate. The extract was washed with 10% hydrochloric acid, washed with water, and dried. The solvent was evaporated and the residue was purified by column chromatography (silica gel, 3:1 mixture of n-hexane and ethyl acetate) to obtain 30 mg (yield, 68.2%) of the title compound as a light yellow oil.

IR(CHCl$_3$): 1701, 1631, 1468, 1222 cm$^{-1}$.

$^1$H-NMR(CDCl$_3$) δ: 1.31(6H, s), 1.60–1.81(2H, m), 2.26(3H, s), 2.69–3.31(2H, m), 3.03(3H, s), 4.42(2H, t, J=6.0 Hz), 4.46(s) 4.47(s) (2H, altogether), 4.90(1H, m), 6.70(1H, s), 7.26–7.35(5H, m).

MS(m/z): 415(M$^+$).

(8) 2-(2-Aminoethyl)-2,3,7,8-tetrahydro-5,8,8-trimethyl-6H-furo[2,3-e]indol-7-one 41.6 mg (0.58 mmol) of 90% sodium azide was added to a solution of 30 mg (0.072 mmol) of 6-benzyl-2-(2-methanesulfonyloxy)ethyl-2,3,7,8-tetrahydro- 5,8,8-trimethyl-6H-furo[2,3-e]indol-7-one dissolved in 1.5 ml of N,N-dimethylformamide, and the mixture was stirred for 2 hours at 150° C. After cooling, the reaction mixture was poured into water and extracted with ethyl acetate. The extract was washed with water and dried. The solvent was evaporated and the residue was purified by separation thin layer chromatography (silica gel, 3:1 mixture of n-hexane and ethyl acetate). Crude crystals obtained was dissolved in 1.5 ml of acetic acid, and 20 mg of 10% palladium-carbon catalyst and a drop of concentrated hydrochloric acid were added to it. The mixture was stirred for 2.5 hours under a hydrogen atmosphere. The reaction mixture was filtered and the filtrate was concentrated under reduced pressure, followed by purification using separation thin layer chromatography (silica gel, 5:1 mixture of chloroform and methanol) to obtain 1.0 mg (yield, 4.1%) of the title compound.

IR(CHCl$_3$): 3378, 1712, 1658, 1265, 1221 cm$^{-1}$.

$^1$H-NMR(CDCl$_3$) δ: 1.40(s) 1.41(s) (6H, altogether), 1.85–2.10(2H, m), 2.48(3H, s), 2.80–3.39(2H, m), 3.53(2H, t, J=7.0 Hz), 4.92(1H, m), 6.93(s) 6.94(s) (1H, altogether).

MS(m/z ): 336 (M$^+$).

Example 12

(1) 4-(1-(trans-4-chloro-2-butenyl)oxy)-2,3-dihydro-3,3,7-trimethyl-1H-indol-2-one 1.78 g (9.31 mmol) of 2,3-dihydro-3,3,7-trimethyl-1H-indol-2-one was dissolved in 20 ml of N,N-dimethylformamide and 20 ml of tetrahydrofuran. Then, after the addition of 5.8 g (46.6 mmol) of trans-1,4-dichloro-2-butene and 2.5 g (18.6 mmol) of potassium carbonate, the mixture was stirred overnight at 50° C. Tetrahydrofuran was evaporated under reduced pressure from the reaction mixture and water was added to the residue, followed by extraction with ether. The organic layer was washed with saturated brine, dried over anhydrous sodium sulfate, and concentrated under reduced pressure. The residue was purified by column chromatography (silica gel, benzene:n-hexane 20:1→10:1) to obtain 2.07 g (yield 90%) of a colorless solid of the title compound.

mp: 164°–165° C. (ethyl acetate-n-hexane, colorless needles).

IR(CHCl$_3$): 1705, 1608, 1501, 1455 cm$^{-1}$.

$^1$H-NMR(CDCl$_3$) δ: 1.48(6H, s), 2.21(3H, s), 4.07–4.14(2H, m), 4.54–4.63(2H, m), 5.96–6.64(2H, m), 6.46(1H, d, J=8.3 Hz), 6.94(1H, d, J=8.3 Hz), 8.23(1H, br. s).

(2) 4-(1-trans-4-acetoxy-2-butenyl)oxy)-2,3-dihydro-3,3,7-trimethyl-1H-indol-2-one 2.07 g (8.39 mmol) of 4-(1-(trans-4-chloro-2-butenyl)oxy)-2,3-dihydro-3,3,7 -trimethyl-1H-indol-2-one was dissolved in 30 ml of N,N-dimethylformamide. 6.88 g (83.9 mmol) of sodium acetate was added and the mixture was heated with stirring for 5 hours at 120° C. The reaction mixture was poured into water and extracted with ether. The organic layer was washed with saturated brine, dried over anhydrous sodium sulfate, and concentrated under reduced pressure. The residue was purified by column chromatography (silica gel, 10:1 mixture of benzene and ethyl acetate) to obtain 2.11 g (yield 82%) of a colorless solid of the title compound.

mp: 103° C. (ether-n-hexane, colorless needles).

IR(CHCl$_3$): 1708, 1608, 1500, 1455 cm$^{-1}$.

$^1$H-NMR(CDCl$_3$) δ: 1.48(6H, s), 2.09(3H, s), 2.21(3H, s), 4.56 (2H, d, J=3.4 Hz), 4.57–4.68(2H, m), 5.88–6.04(2H, m), 6.46(1H, d, J=8.3 Hz), 6.93(1H, d, J=8.3 Hz), 8.25(1H, br. s).

(3) 5-((1-hydroxymethyl)allyl)-2,3-dihydro-4-hydroxy-3,3,7-trimethyl-1H-indol-2-one 2.11 g (6.96 mmol) of 4-(1-trans-4-acetyloxy-2-butenyl)oxy)-2,3-dihydro-3,3,7 -trimethyl-1H-indol-2-one was heated for 7 hours at 210° C. under a stream of argon while stirring. After cooling, 20 ml of methanol was added, and 6.8 ml (20.4 mmol) of 3N aqueous solution of sodium hydroxide was added dropwise under cooling with ice. The mixture was then stirred for 45 minutes at room temperature. Methanol was evaporated under reduced pressure and the residue was poured into water. After adjusting pH to 2 with concentrated hydrochloric acid, the residue was extracted with ether. The organic layer was washed with saturated brine, dried over anhydrous sodium sulfate, and concentrated under reduced pressure. The residue was purified by column chromatography (silica gel, 1:2 mixture of ethyl acetate and n-hexane) to obtain 1.5 g (yield 82%) of a colorless solid of the title compound.

mp: 174° C. (chloroform-n-hexane, colorless needles).

IR(KBr): 3210, 1669, 1621, 1481, 1465, 1453 cm$^{-1}$.

$^1$H-NMR(CDCl$_3$+CD$_3$OD) δ: 1.47(6H, s), 2.16(3H, s), 3.60(1H, m), 3.91(1H, dd, J=6.3, 10.0 Hz), 3.99(1H, dd, J=3.3, 10.0 Hz), 5.07–5.24(2H, m), 6.11(1H, ddd, J=5.9, 10.8, 16.7 Hz).

(4) 2,3,7,8-tetrahydro-5,8,8-trimethyl-3-vinyl-6H-furo[2,3-e]indol-7-one 1.82 g (6.94 mmol) of 5-((hydroxymethyl)allyl)-2,3-dihydro-4-hydroxy-3,3,7-trimethyl-1H-indol-2-one was dissolved in 20 ml of tetrahydrofuran, and to this solution was added a solution of 1.2 g (6.94 mmol) of diethyl ester of azodicarboxylic acid in 5 ml of tetrahydrofuran under cooling with ice. The mixture was stirred for 30 minutes under cooling with ice, and for a further one hour at room temperature. The reaction mixture was then concentrated under reduced pressure. The residue was purified by column chromatography (silica gel, 10:1 mixture of benzene and ethyl acetate) to obtain 1.14 g (yield 81%) of a colorless solid of the title compound. colorless needles).

mp: 189°–190° C. (benzene-n-hexane, colorless needles).
IR(KBr): 1694, 1639 cm$^{-1}$.
$^1$H-NMR(CDCl$_3$+CD$_3$OD) δ: 1.41(3H, s), 1.42(3H, s), 2.18(3H, s), 4.03(1H, m), 4.24(1H, d, J=8.7 Hz), 4.73(1H, t, J=8.7 Hz), 5.12–5.24(2H, m), 5.83(1H, ddd, J=8.3, 9.7, 17.0 Hz), 6.75(1H, s).

The following compounds were prepared in the same manner as in Example 11 (7)–(8).

(5) 3-(2-hydroxyethyl)-2,3,7,8-tetrahydro-5,8,8-trimethyl-6H-furo[2,3-e]indol-7-one Yield: 38%
IR(KBr): 3419, 3184, 2914, 1696, 1639, 1479, 1454 cm$^{-1}$.
$^1$H-NMR(CDCl$_3$) δ: 1.43(6H, s), 1.82(1H, m), 2.03(1H, m), 2.19(3H, s), 3.51(1H, m), 3.77(2H, t, J=6.4 Hz), 4.29(1H, dd, J=6.3, 8.7 Hz), 4.69(1H, t, J=8.7 Hz), 6.81(1H, s), 8.06(1H, br. s).

(6) 3-(2-azidoethyl)-2,3,7,8-tetrahydro-5,8,8-trimethyl-6H-furo[2,3-e]indol-7-one Yield: 73% mp: 128°–129° C. (ether-n-hexane, colorless prisms)
IR(CHCl$_3$): 3420, 3180, 2920, 1703, 1639, 1480, 1454 cm$^{-1}$.
$^1$H-NMR(CDCl$_3$) δ:
1.43(6H, s), 1.78–2.06(2H, m), 2.20(3H, s), 3.32–3.50(3H, m), 4.27(1H, dd, J=5.7, 8.7 Hz), 4.67 (1H, t, J=8.7 Hz), 6.79(1H, s), 8.27(1H, br. s).

(7) 3-(2-amino)ethyl)-2,3,7,8-tetrahydro-5,8,8-trimethyl-6H-furo[2,3-e]indol-7-one•hydrochloride Yield: 65%
mp: 182°–185° C.
IR(KBr): 3400, 3180, 2960, 1675, 1640, 1520, 1490 cm$^{-1}$.
$^1$H-NMR(CD$_3$OD) δ: 1.35(6H, s), 1.81–2.11(2H, m), 2.19(3H, s), 2.87–3.09(2H, m), 3.46(1H, m), 4.30(1H, dd, J=5.3, 9.2 Hz), 4.65(1H, t, J=9.2 Hz), 6.88(1H, s).

Example 13

(1) 3-Hydroxymethyl-2,3,7,8-tetrahydro-5,8,8-trimethyl-6H-furo[2,3-e]indol-7-one 60 ml of acetone, 60 ml of t-butanole, and 20 ml of water were added to 700 mg (2.88 mmol) of 2,3,7,8-tetrahydro-5,8,8-trimethyl-3-vinyl-6 H-furo[2,3-e]indol-7-one. To the mixture were further added 4.31 g (20.16 mmol) of sodium periodate and 0.15 mmol of osmium tetraoxide, dissolved in 3.84 ml (0.57 mmol) of t-butanol, and the mixture was stirred overnight at room temperature. The reaction mixture was filtered through serite and the filtrate was concentrated under reduced pressure. After the addition of water, the residue was extracted with ethyl acetate. The organic layer was washed with saturated brine, dried over anhydrous sodium sulfate, and concentrated under reduced pressure. The residue was dissolved in 5 ml of methanol. 108 mg (2.88 mmol) of sodium borohydride was slowly added under cooling with ice, followed by stirring for 3 hours under cooling with ice, during which 54 mg (1.44 mmol) of sodium borohydride was added twice at 30 minute and at 2.5 hour. The reaction mixture was made pH 3 with the addition of 2N hydrochloric acid, and concentrated under reduced pressure. After the addition of water, the residue was extracted with ethyl acetate. The organic layer was washed with saturated brine, dried over anhydrous sodium sulfate, and concentrated under reduced pressure. The residue was purified by column chromatography (silica gel, 1:1 mixture of n-hexane and ethyl acetate) to obtain 247 mg (yield, 34%) of the title compound.

mp: 187°–188° C. (chloforoform-n-hexane, colorless prisms)
IR(KBr): 3460, 3290, 2800, 1704, 1636, 1452 cm$^{-1}$.
$^1$H-NMR(CDCl$_3$) δ: 1.40(6H, s), 2.18(3H, s), 3.47–3.81(3H, m), 4.48(1H, dd, J=5.3, 8.7 Hz), 4.66(1H, t, J=8.7 Hz), 6.85(1H, s).

(2) 3-Azidomethyl-2,3,7,8-tetrahydro-5,8,8-trimethyl-6H-furo[2,3-e]indol-7-one 245 mg (0.99 mmol) of 3-hydroxymethyl-2,3,7,8-tetrahydro-5,8,8-trimethyl-6 H-furo[2,3-e]indol-7-one was dissolved in 4 ml of pyridine. To the solution 170 mg (1.48 mmol) of methanesulfonyl chloride was added under cooling with ice, and the mixture was stirred for 20 minutes under cooling with ice, and for a further 1.5 hours at room temperature. 1 ml of methanol was added under cooling with ice, followed by stirring for one hour. The reaction mixture was concentrated under reduced pressure. After the addition of water, the residue was extracted with chloroform. The organic layer was washed with 1N hydrochloric acid and saturated brine, dried over anhydrous sodium sulfate, and concentrated under reduced pressure. The residue was dissolved in 8 ml of N,N-dimethylformamide. After the addition of 193 mg (2.97 mmol) of sodium azide, the mixture was stirred for 2 hours at 150° C. The reaction mixture was concentrated under reduced pressure. After the addition of water, the residue was extracted with ethyl acetate. The organic layer was washed with saturated brine, dried over anhydrous sodium sulfate, and concentrated under reduced pressure. The residue was recrystallized from benzene-n-hexane to obtain 210 mg (yield, 77%) of yellow prisms of the title compound.

mp: 183°–184° C.
IR(KBr): 3154, 2930, 2087, 1697, 1638, 1493, 1451, 1438 cm$^{-1}$.
$^1$H-NMR(CDCl$_3$) δ: 1.43(6H, s), 2.20(3H, s), 3.40–3.63(3H, m), 4.41(1H, dd, J=5.2, 8.7 Hz), 4.61(1H, t, J=8.7 Hz), 6.86(1H, s), 8.22(1H, br. s).

(3) 3-Aminomethyl-2,3,7,8-tetrahydro-5,8,8-trimethyl-6H-furo[2,3-e]indol-7-one•hydrochloride 220 mg (0.81 mmol) of 3-azidomethyl-2,3,7,8-tetrahydro-5,8,8-trimethyl-6 H-furo[2,3-e]indol-7-one was dissolved in a mixture of 2 ml of methanol and 2 ml of tetrahydrofuran, and 50 mg of 10% palladium-carbon catalyst was added to the solution. The mixture was stirred for 1.5 hours at room temperature under a hydrogen atmosphere. The reaction mixture was filtered through cerite and the filtrate was concentrated under reduced pressure. The residue obtained was submitted to column chromatography (silica gel, 20:1:0.1 mixture of chloroform, methanol, and ammonia water) to obtain a free base. This free base was dissolved in 3 ml of methanol. After the addition of 0.86 ml of 1.35N methanol solution of hydrochloric acid, the mixture was concentrated under reduced pressure. The residue was made into powder with the addition of ether and filtered, to obtain 190 mg (yield, 83%) of a yellow solid of the title compound.

IR(KBr): 3415, 2957, 1675, 1639, 1505, 1451, 1419 cm$^{-1}$.

$^1$H-NMR(CD$_3$OD) δ: 1.35(3H, s), 1.36(3H, s), 2.20(3H, s), 3.39 (1H, dd, J=8.1, 13.5 Hz), 3.22(1H, dd, J=5.4, 13.5 Hz), 3.69(1H, m), 4.49(1H, dd, J=4.8, 9.7 Hz), 4.67(1H, dd, J=8.7, 9.7 Hz), 6.96(1H, s).

Example 14

2-Methylaminomethyl-2,3,7,8-tetrahydro-5,8,8-trimethyl-6H-furo[2,3-e]indol-7-one•hydrochloride 606 mg (1.95 mmol) of 2-bromomethyl-2,3,7,8-tetrahydro-5,8,8-trimethyl-6H-furo[2,3-e]indol-7-one was dissolved in 7 ml of 30% methylamine solution in ethanol. The mixture was stirred for one hour at 150° C. in a sealed tube. After the reaction, the reaction mixture was concentrated under reduced pressure. The residue was diluted with a mixed solvent of 4:1 chloroform and methanol, washed with an aqueous solution of sodium hydrogen carbonate and saturated brine and dried over anhydrous sodium sulfate. The solvent was evaporated and the residue was purified by column chromatography (silica gel, chloroform:methanol= 20:1 →10:1) to obtain 458 mg (1.76 mmol, yield: 90.0%) of a free base. This free base was made into hydrochloride and recrystallized from methanol-ether mixture to obtain 430 mg of the title compound.

mp: 278°–280° C.

IR(KBr): 2921, 2657, 1689, 1641, 1473, 1260, 1090, 1030 cm$^{-1}$.

$^1$H-NMR(CD$_3$OD) δ: 1.39(3H, s), 1.42(3H, s), 2.18(3H, s), 2.83 (3H, s), 2.91(1H, dd, J=7.7, 15.5 Hz), 3.31(2H, d, J=7.7 Hz), 3.30–3.42(1H, m), 5.03–5.15(1H, m), 6.88(1H, s).

Compounds in Examples 15–22 were prepared in the same manner as in Example 14.

Example 15

2-Benzylaminomethyl-2,3,7,8-tetrahydro-5,8,8-trimethyl-6H-furo[2,3-e]indol-7-one•hydrochloride mp: 169°–172° C.

IR(KBr): 2956, 2853, 1706, 1641, 1480, 1456, 1242, 1086 cm$^{-1}$.

$^1$H-NMR(CD$_3$OD) δ: 1.39(3H, s), 1.40(3H, s), 2.17(3H, s), 2.90 (1H, dd, J=7.2, 16.0 Hz), 3.28–3.38(3H, m), 3.90(2H, d, J=2.2 Hz), 5.05–5.17(1H, m), 6.87(1H, s), 7.46–7.53(5H, m).

Example 16

2-(1-Imidazolyl)methyl-2,3,7,8-tetrahydro-5,8,8-trimethyl-6H-furo[2,3-e]indol-7-one•hydrochloride mp: 267°–270° C.

IR(KBr): 3142, 2920, 1700, 1638, 1478, 1454, 1306, 1245, 1086 cm$^{-1}$.

$^1$H-NMR(CD$_3$OD) δ: 1.31(3H, s), 1.38(3H, s), 2.15(3H, s), 2.97 (1H, dd, J=6.1, 15.6 Hz), 3.36–3.45(1H, m), 4.49(1H, dd, J=7.6, 14.4 Hz), 4.65(1H, dd, J=3.1, 14.4 Hz), 5.12–5.28(1H, m), 6.85(1H, s), 7.58(1H, d, J=1.6 Hz), 7.70(1H, d, J=1.6 Hz), 8.98(1H, s).

Example 17

2-Dimethylaminomethyl-2,3,7,8-tetrahydro-5,8,8-trimethyl-6H-furo[2,3-e]indol-7-one•hydrochloride mp: 268°–270° C.

IR(KBr): 3376, 3125, 1701, 1638, 1473, 1434, 1245, 1088 cm$^{-1}$.

$^1$H-NMR(CD$_3$OD) δ: 1.39(3H, s), 1.40(3H, s), 2.18(3H, s), 2.89 (1H, dd, J=7.6, 16.6 Hz), 3.05(6H, s), 3.35–3.59(3H, m), 5.19–5.27(1H, m), 6.89(1H, s).

Example 18

2-n-Butylaminomethyl-2,3,7,8-tetrahydro-5,8,8-trimethyl-6H-furo[2,3-e]indol-7-one•hydrochloride mp: 195°–197° C.

IR(KBr): 3140, 2947, 1704, 1661, 1478, 1455, 1242, 1087 cm$^{-1}$.

$^1$H-NMR(CD$_3$OD) δ: 1.01(3H, t, J=7.3 Hz), 1.39(3H, s), 1.42(3H, s), 1.40–1.50(4H, m), 1.73(2H, dt, J=7.6, 15.9 Hz), 2.18 (3H, s), 2.91(1H, dd, J=8.3, 15.6 Hz), 3.05–3.22(2H, m), 3.35–3.42(1H, m), 5.03–5.13(1H, m), 6.88(1H, s).

Example 19

2-(1-Piperidinyl)methyl-2,3,7,8-tetrahydro-5,8,8-trimethyl-6H-furo[2,3-e]indol-7-one•hydrochloride mp: 261°–265° C. (Decomposed).

IR(KBr): 2924, 2703, 1710, 1661, 1481, 1457, 1245, 1086, 1002 cm$^{-1}$.

$^1$H-NMR(CD$_3$OD) δ: 1.38(3H, s), 1.39(3H, s), 1.50–1.70(2H, m), 1.77–2.05(4H, m), 2.18(3H, s), 2.89(1H, dd, J=7.1, 16.1 Hz), 3.05–3.23(2H, m), 3.39(1H, dd, J=8.8, 16.1 Hz), 3.49(2H, d, J=7.1 Hz), 3.52–3.65(1H, m), 3.70–3.87(1H, m), 5.21–5.31(1H, m), 6.89(1H, s).

Example 20

2-(4-Benzyl-1-piperadinyl )methyl-2,3,7,8-tetrahydro-5,8,8-trimethyl-6H-furo[2,3-e]indol-7-one•dihydrochloride mp: 265°–271° C. (Decomposed).

IR(KBr): 3161, 3051, 1707, 1642, 1479, 1454, 1266, 1087 cm$^{-1}$.

$^1$H-NMR(CD$_3$OD) δ: 1.37(6H, s), 2.17(3H, s), 2.92(1H, dd, J=7.7, 15.0 Hz), 3.47(2H, d, J=5.5 Hz), 3.35–3.75(9H, m), 4.43(2H, s), 5.18–5.32(1H, m), 6.87(1H, s), 7.46–7.60(5H, m).

Example 21

2-[(N-Methyl-N-phenyl)aminomethyl]-2,3,7,8-tetrahydro-5,8,8-trimethyl-6H-furo[2,3-e]indol-7-one IR(CHCl$_3$): 2958, 1705, 1640, 1503, 1478, 1241, 1215, 1087 cm$^{-1}$.

$^1$H-NMR(CDCl$_3$) δ: 1.44(6H, s), 2.19(3H, s), 2.80–2.90(1H, m), 3.06(3H, s), 3.13–3.38(1H, m), 3.48–3.62(2H, m), 4.98–5.15(1H, m), 6.65–6.80(4H, m), 6.99–7.06(1H, m), 7.19–7.28(1H, m), 8.18–8.23(1H, m).

Example 22

2-(1-Piperadinyl)methyl-2,3,7,8-tetrahydro-5,8,8-trimethyl-6H-furo[2,3-e] indol-7-one•dihydrochloride 2.03 g (4.24 mmol) of 2-(4-benzyl-1-piperadinyl)-methyl-2,3,7,8-tetrahydro-5,8,8 -trimethyl-6H-furo[2,3e]indol-7-one dihydrochloride was dissolved in 100 ml of water, and 10% palladium-carbon catalyst was added to the solution. The mixture was stirred for 1.5 hours at 80° C. under a hydrogen atmosphere. After the reaction, the mixture was filtered and the solvent was evaporated. The residue was recrystallized from methanol-ether to obtain 1.43 g (3.68 mmol, yield: 86.8%) of the title compound.

mp: 241°–243° C (Decomposed).

IR(KBr): 2912, 2645, 1702, 1640, 1450, 1380, 1309, 1256, 1088 cm$^{-1}$.

$^1$H-NMR(CD$_3$OD) δ: 1.40(6H, s), 2.18(3H, s), 2.94(1H, dd, J=7.5, 16.2 Hz), 3.40(1H, dd, J=9.2, 16.2 Hz), 3.61 (2H, d, J=5.9 Hz), 3.57–3.72(6H, m), 3.72–3.87(2H, m), 5.28–5.38(1H, m), 6.88(1H, s).

Example 23

2-[4-(3,4-dimethoxybenzoyl)-1-piperadinyl]methyl-2,3,7,8-tetrahydro-5,8,8-trimethyl-6 H-furo[2,3-e]indol-7-one•hydrochloride 492 mg (1.56 mmol) of 2-(1-piperadinyl)methyl-2,3,7,8-tetrahydro-5,8,8-trimethyl-6 H-furo[2,3-e]indol-7-one was dissolved in 5 ml of pyridine. 376 mg (1.87 mmol) of 3,4-dimethoxybenzoyl chloride was added, and the mixture was stirred for 18 hours at room temperature. After the reaction, 1 ml of methanol was added and the mixture was further stirred for 10 minutes at room temperature and concentrated under reduced pressure. The residue obtained was diluted with a mixed solvent of 5:1 chloroform and methanol, washed with an aqueous solution of sodium hydrogen carbonate and brine and dried over anhydrous sodium sulfate. The solvent was evaporated and the residue was purified by column chromatography (silica gel, chloroform:methanol=20:1) to obtain 683 mg (1.42 mmol, yield: 91.0%) of a free base. This free base was made into hydrochloride and recrystallized from methanol-ether to obtain 638 mg of the title compound.

mp: 184°–187° C.

IR(KBr): 3395, 2952, 1699, 1636, 1459, 1422, 1260, 1018 cm$^{-1}$.

$^1$H-NMR(CD$_3$OD) δ: 1.39(6H, s), 2.18(3H, s), 2.92(1H, dd, J=7.9, 15.8 Hz), 3.41(1H, dd, J=9.3, 15.8 Hz), 3.61 (2H, d, J=4.9 Hz), 3.30–3.70(8H, m), 3.87(3H, s), 3.88(3H, s), 5.25–5.38(1H, m), 6.89(1H, s), 7.04 (1H, d, J=7.7 Hz), 7.10(1H, s), 7.12(1H, d, J=7.7 Hz).

Example 24

(1) 4-Allyloxy-2,3-dihydro-3,3-dimethyl-1H-indol-2-one 1.01 g (5.71 mmol) of 2,3-dihydro-3,3-dimethyl-4-hydroxy-1H-indol-2-one, 1.92 g (5.99 mmol) of allyl iodide, and 1.57 g (11.4 mmol) of potassium carbonate were added to 8.73 ml of N,N-dimethylformamide, and the mixture was stirred for one hour over a water bath at 70° C. After the reaction, the solvent was evaporated and chloroform was added to the residue. The residue was then washed with water, 2N aqueous solution of sodium hydroxide, and brine, dried over anhydrous sodium sulfate, and concentrated under reduced pressure. The residue obtained was purified by column chromatography (silica gel, chloroform) to obtain 914 mg (yield: 70.2%) of colorless prisms of the title compound.

mp: 114°–116° C.

IR(KBr): 3160, 1707, 1668, 1616, 1605, 1463, 1455, 1271, 1248, 1052, 760 cm$^{-1}$.

$^1$H-NMR(CDCl$_3$) δ: 1.49(6H, s), 4.58(2H, m), 5.31(1H, ddd, J=1.5, 2.9, 10.7 Hz), 5.43(1H, ddd, J=1.5, 3.4, 17.1 Hz), 7.16(1H, t, J=8.3 Hz), 8.25(1H, br.).

(2) 5-Allyl-2,3-dihydro-4-hydroxy-3,3-dimethyl-1H-indol-2-one 914 mg (4.21 mmol) of 4-allyloxy-2,3-dihydro-3,3-dimethyl-1H-indol-2-one was added to 4 ml of N,N-dimethylaniline, and the mixture was heated for 30 hours at 205° C. while stirring. After the reaction, N,N-dimethylaniline was evaporated under reduced pressure. The residue was dissolved in chloroform, washed with water, 2N hydrochloric acid, and saturated brine, dried over anhydrous sodium sulfate, and concentrated under reduced pressure. The residue obtained was purified by column chromatography (silica gel, chloroform:ethyl acetate=20:1), washed with ether-n-hexane, and filtered to obtain 890 mg (yield: 97.4%) of a brown oil of the title compound.

IR(Cap.): 3213, 2964, 1696, 1627, 1476, 1452, 1378, 1266, 1245, 1048, 754 cm$^{-1}$.

$^1$H-NMR(CDCl$_3$) δ: 1.49(6H, s), 3.40(2H, d, J=6.4 Hz), 5.20–5.30 (2H, m), 6.03(1H, m), 6.47(1H, d, J=7.8 Hz), 6.93 (1H, d, J=7.8 Hz), 8.14(1H, br. s).

(3) 5-Bromo-2-bromomethyl-8,8-dimethyl-2,3,7,8-tetrahydro-6H-furo[2,3-e] indol-7-one 890 mg (4.1 mmol) of 5-allyl-2,3-dihydro-4-hydroxy-3,3-dimethyl-1H-indol-2-one and 795 mg (4.47 mmol) of N-bromosuccinimide were added to 29 ml of chloroform, and the mixture was stirred for 2 hours at room temperature. 480 mg (2.70 mmol) of N-bromosuccinimide was further added and the mixture was stirred for a further 1.5 hours. After the reaction, the reaction mixture was washed with water, dried over anhydrous sodium sulfate, and concentrated under reduced pressure. The residue obtained was purified by column chromatography (silica gel, chloroform) to obtain 1.2 g (yield: 78.0%) of light brown crystals of the title compound.

IR(KBr): 3160, 1700, 1643, 1454, 1436, 1246, 1060 cm$^{-1}$.

$^1$H-NMR(CDCl$_3$) δ: 1.48(6H, s), 3.10(1H, ddd, J=1.0, 5.9, 15.6 Hz), 3.38(1H, ddd, J=1.0, 9.3, 15.6 Hz), 3.51–3.67(2H, m), 5.11(1H, m), 7.13(1H, s), 8.00(1H, br. s).

(4) 2-Azidomethyl-5-bromo-8,8-dimethyl-2,3,7,8-tetrahydro-6H-furo[2,3 -e]indol-7-one 21.5 ml of N,N-dimethylformamide was added to 1.2 g (3.2 mmol) of 5-bromo-2-bromomethyl-8,8-dimethyl-2,3,7,8-tetrahydro-6H-furo[2,3-e] indol-7-one and 1.5 g (23 mmol) of sodium azide, and the mixture was heated for 40 minutes over a water bath at 100° C. while stirring. After cooling, the solvent was evaporated. After the addition of chloroform, the residue was washed with water and saturated brine, dried over anhydrous sodium sulfate, and concentrated under reduced pressure. The residue obtained was purified by column chromatography (silica gel, 2:1 mixture of benzene and ethyl acetate) to obtain 600 mg (yield: 79.1%) of colorless crystals of the title compound.

IR(KBr): 3109, 2088, 1694, 1638, 1454, 1431, 1276, 1244, 1059 cm$^{-1}$.

$^1$H-NMR (CDCl$_3$) δ: 1.45(6H, s), 2.99(1H, dd, J=6.8, 15.6 Hz), 3.28(1H, dd, J=9.3, 15.6 Hz), 3.43(1H, dd, J=5.4, 13.2 Hz), 3.53(1H, dd, J=3.9, 13.2 Hz), 5.06(1H, m), 7.10(1H, s), 7.43(1H, br.).

(5) 2-Aminomethyl-5-bromo-8,8-dimethyl-2,3,7,8-tetrahydro-6H-furo[2,3-e]indol-7 -one•hydrochloride 600 mg (2.53 mmol) of 2-azidomethyl-5-bromo-8,8-dimethyl-2,3,7,8-tetrahydro-6 H-furo[2,3-e]indol-7-one was dissolved in 60 ml of 1:1 mixture of tetrahydrofuran and methanol, and 600 mg of 10% palladium-carbon catalyst was added to the solution. The mixture was stirred for 2 hours over a water bath at 50° C. under a hydrogen atmosphere. After the reaction, the catalyst was removed by filtration and the filtrate was concentrated under reduced pressure. After the addition of 2 ml of 2N aqueous solution of sodium hydroxide, the residue was extracted with chloroform. The extract was dried over anhydrous sodium sulfate and concentrated under reduced pressure to obtain 450 mg of colorless crystals. This product was made into hydrochloride and recrystallized from methanol-ether, thus obtaining 293 mg (yield: 43.1%) of light yellow crystals of the title compound.

mp: >250° C.

IR(KBr): 3379, 2956, 1694, 1645, 1612, 1468, 1453, 1248, 1045 cm$^{-1}$.

$^1$H-NMR(CD$_3$OD) δ: 1.39(3H, s), 1.43(3H, s), 2.94(1H, dd, J=7.3, 15.6 Hz), 3.24(1H, dd, J=7.6, 15.6 Hz), 3.25–3.44(2H, m), 5.06(1H, m), 6.48(1H, d, J=7.7 Hz), 7.04(1H, d, J=7.7 Hz).

Example 25

(1) 2-Bromo-4-n-hexyl-1-methoxybenzene 26.4 g (0.137 mol) of 4-n-hexyl-1-methoxybenzene was dissolved in 200 ml of methanol. 26.4 g (0.156 mol) of bromine was added while stirring under cooling with ice. The mixture was stirred for 2 hours, while raising the temperature to room temperature. Sodium sulfite was added to the reaction mixture to decompose an excess amount of bromine, whereupon the mixture was extracted with chloroform-water. The organic layer was washed with saturated brine, dried over anhydrous sodium sulfate, and concentrated under reduced pressure. The residue obtained was purified by column chromatography (silica gel, 20:1 mixture of n-hexane and ethyl acetate) to obtain 35.18 g (yield, 95.8%) of a colorless oil of the title compound.

IR(Cap.): 3411, 2923, 1630, 1605, 1497, 1460, 1440, 1275, 1253, 1053, 1020, 803 cm$^{-1}$.

$^1$H-NMR(CDCl$_3$) δ: 1.23–1.38(6H, m), 1.49–1.62(2H, m), 2.52(2H, t, J=7.3 Hz), 3.87(3H, s), 6.81(1H, d, J=8.3 Hz), 7.06(1H, dd, J=2.4, 8.3 Hz), 7.36(1H, d, J=2.4 Hz).

The following compounds were prepared in the same manner as in Examples 1 and 2.

(2) 2-Benzylamino-1-n-hexyl-1-methoxybenzene

IR(Cap.): 3479, 2900, 2846, 1609, 1583, 1505, 1445, 1290, 1204, 1184, 1040 cm$^{-1}$.

$^1$H-NMR(CDCl$_3$) δ: 1.29–1.40(6H, m), 1.57(2H, m), 2.42(2H, t, J=7.3 Hz), 3.73(3H, s), 4.34(2H, s), 6.21(1H, d, J=2.4 Hz), 6.24(1H, dd, J=2.4, 7.8 Hz), 6.95(1H, d, J=7.8 Hz), 7.27–7.38(5H, m).

(3) N-Benzyl-2-n-hexyl-5-methoxy(2-bromoisobutylo)anilide

IR (Cap.): 2917, 1639, 1607, 1479, 1463, 1387, 1286, 1239, 1196, 1167, 1104, 1076, 1032, 697 cm$^{-1}$.

$^1$H-NMR(CDCl$_3$) δ: 0.91(3H, t, J=6.8 Hz), 1.25–1.54(6H, m), 1.55–1.61(2H, m), 1.95(6H, s), 2.47(2H, t, J=7.3 Hz), 3.56(3H, s), 3.87(1H, d, J=14.2 Hz), 5.69 (1H, d, J=14.2 Hz), 6.51(1H, d, J=2.4 Hz), 6.82(1H, dd, J=2.4, 7.8 Hz), 7.19(1H, d, 7.25–7.27 (5H, m).

(4) 2,3-Dihydro-3,3-dimethyl-7-n-hexyl-4-hydroxy-1H-indol-2-one

IR(Cap.): 3206, 2910, 2848, 1676, 1624, 1502, 1444, 1382, 1316, 1277, 1214, 1159, 1038, 801,755, 666 cm$^{-1}$.

$^1$H-NMR (CDCl$_3$) δ: 0.88(3H, t, J=6.8 Hz), 1.31–1.42(6H, m), 1.51 (6H, s, overlapped with 1.49–1.57, 2H, m), 2.47(2H, t, J=7.3 Hz), 4.87(1H, br. s), 6.38(1H, d, J=8.3 Hz), 6.86(1H, d, J=8.3 Hz), 8.04(1H, br.).

(5) 4-Allyloxy-2,3-dihydro-3,3-dimethyl-7n-hexyl-1H-indol-2-one

IR(Cap.): 3154, 3060, 2910, 2848, 1705, 1684, 1622, 1603, 1501, 1457, 1431, 1377, 1325, 1257, 1164, 1111, 1090, 1076, 971, 920, 788, 756 cm$^{-1}$.

$^1$H-NMR(CDCl$_3$) δ: 0.88(3H, t, J=6.8 Hz), 1.31–1.44(6H, m), 1.49 (6H, s, overlapped with 1.45–1.62, 2H, m), 2.49(2H, t, J=7.3 Hz), 4.55(2H, ddd, J=2.9, 3.4, 4.9 Hz), 5.28 (1H, ddd, J=17. 2.9, 10.5 Hz), 5.42(1H, ddd, J=1.7, 3.4, 17.3 Hz), 6.06(1H, ddt, J=4.9, 10.5, 17.3 Hz), 6.49(1H, d, J=8.5 Hz), 6.94(1H, d, J=8.5 Hz), 8.10(1H, br.).

(6) 5-Allyl-2,3-dihydro-3,3-dimethyl-7-n-hexyl-4-hydroxy-1H-indol-2-one

IR(Cap.): 3192, 2918, 2850, 1697, 1622, 1484, 1452, 1379, 1353, 1312, 1255, 1227, 1110, 992, 910, 755, 724 cm$^{-1}$.

$^1$H-NMR(CDCl$_3$) δ: 0.89(3H, t, J=6.8 Hz), 1.26–1.41(6H, m), 1.49 (6H, s, overlapped with 1.43–1.58, 2H, m), 2.47(2H, t, J=7.3 Hz), 3.37(2H, d, J=6.4 Hz), 5.08(1H, s), 5.22(1H, dd, J=1.5, 9.8 Hz), 5.24(1H, dd, J=1.5, 20.5 Hz), 6.04(1H, ddt, J=6.4, 9.8, 20.5 Hz), 6.74 (1H, s), 8.16(1H, br.).

(7) 8,8-Dimethyl-5-n-hexyl-2-iodomethyl-2,3,7,8-tetrahydro-6H-furo[2,3-e]indol-7-one 2.53 g (8.41 mmol) of 5-allyl-2,3-dihydro-3,3-dimethyl-7-n-hexyl-4-hydroxy-1 H-indol-2-one was dissolved in 200 ml of a 4:1 chloroform-methanol mixture. 7.0 g (16.9 mmol) of potassium carbonate, 4.5 g (20.1 mmol) of potassium iodide, and 4.3 g (16.9 mmol) of iodine were successively added in this order, and the mixture was stirred for 25 hours at room temperature. Sodium sulfite was added to the reaction mixture to decompose an excess amount of iodine, whereupon the mixture was extracted with chloroform-water. The organic layer was washed with saturated brine, dried over anhydrous sodium sulfate, and concentrated under reduced pressure. The residue obtained was recrystallized from n-hexane to obtain 2.40 g (yield, 66.9%) of colorless needles of the title compound.

mp: 126°–127° C.

IR(KBr): 3400, 3300, 2916, 1709, 1640, 1476, 1433, 1315, 1212, 1094 cm$^{-1}$.

$^1$H-NMR(CDCl$_3$) δ: 0.89(3H, t, J=6.8 Hz), 1.25–1.40(6H, m), 1.44 (3H, s), 1.45(3H, s), 1.49–1.57(2H, m), 2.44(2H, t, J=7.3 Hz), 2.95(1H, ddd, J=1.0, 6.1, 15.6 Hz), 3.33 (1H, ddd, J=1.9, 6.6, 15.6 Hz), 3.34(1H, dd, J=7.3, 9.8 Hz), 3.43(1H, dd, J=4.9, 9.8 Hz), 4.89(1H, m), 6.80(1H, s), 7.71(1H, br.).

The following compound was prepared in the same manner as in Example 1.

(8) 2-Azidomethyl-8,8-dimethyl-5-n-hexyl-2,3,7,8-tetrahydro-6H-furo[2,3-e] indol-7-one mp: 119°–121° C.

IR(KBr): 3156, 3070, 2919, 2850, 2083, 1695, 1641, 1477, 1460, 1431, 1378, 1316, 1258, 1222, 1100, 1037, 863, 639 cm$^{-1}$.

$^1$H-NMR(CDCl$_3$) δ: 0.88(3H, t, J=6.8 Hz), 1.22–1.41(6H, m), 1.45 (6H, s) 1.49–1.64(2H, m), 2.49(2H, t, J=7.3 Hz), 2.94(1H, dd, J=6.8, 15.6 Hz), 3.22(1H, dd, J=8.8, 15.6 Hz), 3.45(2H, d, J=4.9 Hz), 5.01(1H, m), 6.82 (1H, s), 8.50(1H, br.).

(9) 2-Aminomethyl-8,8-dimethyl-5-n-hexyl-2,3,7,8-tetrahydro-6H-furo[2,3-e]indol-7-one·hydrochloride mp: 242°–245° C. (Decomposed).

IR(KBr): 67, 3144, 2916, 1705, 1641, 1478, 1458, 1433, 1380, 1310, 1244, 1223, 1095, 1082, 1010, 977, 756, 639 cm$^{-1}$.

$^1$H-NMR(CD$_3$OD) δ: 0.88(3H, t, J=6.8 Hz), 1.25–1.37(6H, m), 1.38 (3H, s), 1.42(3H, s), 1.45–1.57(2H, m), 2.51(2H, t, J=7.3 Hz), 2.92(1H, dd, J=7.3, 15.6 Hz), 3.19(1H, dd, J=9.0, 13.4 Hz), 3.22(1H, dd, J=6.8, 15.6 Hz), 3.36 (1H, dd, J=9.3, 13.4 Hz), 5.03(1H, m), 6.88(1H, s).

Example 26

The following compounds were prepared in the same manner as in Examples 1, 2, and 25.

(1) N-Benzyl-2-ethyl-5-methoxy(2-bromoisobutyl)anilide
mp: 79°–80° C.
IR(KBr): 2951, 2905, 1630, 1610, 1570, 1493, 1459, 1428, 1391, 1363, 1352, 1288, 1236, 1197, 1183, 1166, 1134, 1106, 1076, 1035, 990, 932, 826, 736, 697 cm$^{-1}$.
$^1$H-NMR(CDCl$_3$) δ: 1.23(3H, t, J=7.3 Hz), 1.46(3H, s), 1.95(3H, s), 2.53(2H, t, J=7.3 Hz), 3.57(3H, s), 3.85(1H, d, J=13.7 Hz), 5.70(1H, d, J=13.7 Hz), 6.83(1H, d, J=2.4 Hz), 6.85(1H, dd, J=2.4, 8.3 Hz), 7.00(1H, d, J=8.3 Hz), 7.24–7.31(5H, m).

(2) 4-Allyloxy-2,3-dihydro-3,3-dimethyl-7-ethyl-1H-indol-2-one
mp: 149°–151° C.
IR(KBr): 3151, 3050, 2960, 1691, 1620, 1602, 1501, 1456, 1431, 1377, 1321, 1262, 1075, 1052, 973, 949, 863, 798, 780, 689, 640 cm$^{-1}$.
$^1$H-NMR(CDCl$_3$) δ: 1.22(3H, t, J=7.6 Hz), 1.49(6H, s), 2.53(2H, q, J=7.6 Hz), 4.55(2H, ddd, J=2.9, 3.4, 4.9 Hz), 5.28(1H, ddd, J=1.7, 2.8, 10.5 Hz), 5.42(1H, ddd, J=1.7, 3.4, 17.3 Hz), 6.05(1H, ddt, J=4.9, 10.5, 17.3 Hz), 6.51(1H, d, J=8.5 Hz), 6.98(1H, d, J=8.5 Hz), 7.72 (1H, br.).

(3) 5-Allyl-2,3-dihydro-3,3-dimethyl-7ethyl-4-hydroxy-1H-indol-2-one
IR(Cap.): 3189, 2954, 1696, 1623, 1482, 1448, 1445, 1377, 1310, 1253, 1219, 1105, 1040, 990, 911, 868, 753 cm$^{-1}$.
$^1$H-NMR(CDCl$_3$) δ: 1.21(3H, t, J=7.6 Hz), 1.50(6H, s), 2.56(2H, q, J=7.6 Hz), 3.38(2H, d, J=6.4 Hz), 5.21(1H, dd, J=1.5, 9.8 Hz), 5.23(1H, dd, J=1.5, 20.5 Hz), 5.24 (1H, s), 6.02(1H, ddt, J=6.4, 9.8, 20.5 Hz), 6.76 (1H, s), 9.09(1H, br.).

(4) 8,8-Dimethyl-5-ethyl-2-iodomethyl-2,3,7,8-tetrahydro-6H-furo[2,3-e]indol-7-one
mp: 169°–171° C.
IR(KBr): 3161, 2955, 1708, 1641, 1476, 1456, 1432, 1313, 1261, 1238, 1093, 994, 641 cm$^{-1}$.
$^1$H-NMR(CDCl$_3$) δ: 1.21(3H, t, J=7.6 Hz), 1.44(3H, s), 1.45(3H, s), 2.50(2H, q, J=7.6 Hz), 2.96(1H, ddd, J=1.0, 6.1, 15.6 Hz), 3.30(1H, ddd, J=1.0, 6.6, 15.6 Hz), 3.35 (1H, dd, J=7.3, 10.3 Hz), 3.43(1H, dd, J=4.9, 10.3 Hz), 4.89(1H, m), 6.83(1H, s), 8.46(1H, br.).

(5) 2-Azidomethyl-8,8-dimethyl-5-ethyl-2,3,7,8-tetrahydro-6H-furo[2,3-e] indol-7-one
mp: 151°–153° C.
IR(KBr): 3402, 3153, 2957, 2091, 1696, 1637, 1481, 1457, 1431, 1378, 1312, 1252, 1091, 1030, 887, 868, 638 cm$^{-1}$.
$^1$H-NMR(CDCl$_3$) δ: 1.21(3H, t, J=7.6 Hz), 1.46(6H, s), 2.52(2H, q, J=7.6 Hz), 2.95(1H, dd, J=6.8, 15.6 Hz ), 3.27(1H, dd, J=8.8, 15.6 Hz), 3.46(2H, d, J=4.9 Hz), 5.03(1H, m), 6.85(1H, s), 8.19(1H, br.).

(6) 2-Aminomethyl-8,8-dimethyl-5-ethyl-2,3,7,8-tetrahydro-6H-furo[2,3-e] indol-7-one•hydrochloride
mp: 265°–267° C. (Decomposed).
IR(KBr): 3386, 2956, 1704, 1642, 1478, 1457, 1433, 1381, 1310, 1260, 1240, 1092, 1012, 984, 959, 869, 825, 751, 637 cm$^{-1}$.
$^1$H-NMR(CD$_3$OD) δ: 1.12(3H, t, J=7.6 Hz), 1.38(3H, s), 1.42(3H, s), 2.53(2H, q, J=7.6 Hz), 2.89(1H, dd, J=7.3, 15.6 Hz), 3.15–3.36(3H, m), 4.99(1H, m), 6.91(1H, s).

Example 27

The following compounds were prepared in the same manner as in Examples 1 and 2.

(1) 1-Benzyl-2,3-dihydro-3,3-dimethyl-4-hydroxy-7-(-n-propyl)-1H-indol-2-one
Yield: 23.5%, colorless needles
IR(KBr): 3356, 1679, 1633, 1608, 1445, 1385, 1274, 953, 801 cm$^{-1}$.
$^1$H-NMR(CDCl$_3$) δ: 0.86(3H, t, J=7.3 Hz), 1.35–1.50(2H, m), 1.57 (6H, s), 2.41(2H, t, J=7.8 Hz), 5.13(2H, s), 5.24 (1H, s), 6.40(1H, d, J=8.3 Hz), 6.79(1H, d, J=8.3 Hz), 7.09–7.35(5H, m).

(2) 2,3-Dihydro-3,3-dimethyl-4-hydroxy-7-(n-propyl)-1H-indol-2-one
IR(CHCl$_3$): 3239, 1667, 1627, 1508, 1448, 1279, 1039, 808 cm$^{-1}$.
$^1$H-NMR(CDCl$_3$) δ: 0.96(3H, t, J=7.3 Hz), 1.50(6H, s), 1.50–1.70 (2H, m), 2.46(2H, t, J=7.8 Hz), 5.39(1H, s), 6.38 (1H, d, J=8.3 Hz), 6.85(1H, d, J=8.3 Hz), 8.10(1H, br. s).

(3) 4-Allyloxy-2,3-dihydro-3,3-dimethyl-7-(n-propyl)-1H-indol-2-one
Yield: 43.8%, colorless powder
mp: 143°–145° C.
IR(KBr): 1700, 1609, 1434, 1258, 1090, 935, 802 cm$^{-1}$.
$^1$H-NMR(CDCl$_3$) δ: 1.00(3H, t, J=7.3 Hz), 1.49(6H, s), 1.55–1.70 (2H, m), 2.49(2H, t, J=8.1 Hz), 4.56(2H, d, J=4.9 Hz), 5.28(1H, dd, J=1.7, 10.6 Hz), 5.42(1H, dd, J=1.7, 17.3 Hz), 6.05(1H, m), 6.50(1H, d, J=8.5 Hz), 6.94(1H, d, J=8.5 Hz), 8.25(1H, br. s).

(4) Allyl-2,3-dihydro-3,3-dimethyl-4-hydroxy-7-(n-propyl)-1H-indol-2-one
Yield: 90%, light yellow powder
mp: 143°–144° C.
IR(KBr): 3501, 1706, 1629, 1485, 1447, 1259, 1121, 935, 469 cm$^{-1}$.
$^1$H-NMR(CDCl$_3$) δ: 0.97(3H, t, J=7.3 Hz), 1.49(6H, s), 1.55–1.65 (2H, m), 2.46(2H, t, J=8.1 Hz), 3.37(2H, d, J=7.6 Hz), 5.07(1H, s), 5.20–5.30(2H, m), 6.05(1H, m), 6.74(1H, s), 8.25(1H, br. s).

(5) 2-Bromomethyl-8,8-dimethyl-5-(n-propyl)-2,3,7,8-tetrahydro-6H-furo[2,3-e]indol-7-one
Yield: 85.4%, colorless needles
mp: 188°–190° C.
IR(KBr): 1712, 1646, 1480, 1439, 1097, 1003, 766, 645 cm$^{-1}$.
$^1$H-NMR(CDCl$_3$) δ: 0.97(3H, t, J=7.3 Hz), 1.44(6H, s), 1.40–1.65 (2H, m), 2.46(2H, t, J=7.8 Hz), 3.03(1H, dd, J=5.9, 16.5 Hz), 3.33(1H, dd, J=8.8, 16.5 Hz), 3.45–3.63(2H, m), 5.05(1H, m), 6.81(1H, s), 8.30(1H, br. s).

(6) 2-Azidomethyl-8,8-dimethyl-5-(n-propyl)-2,3,7,8-tetrahydro-6H-furo[2,3-e]indol-7-one
Yield: 96.8%, light yellow prisms mp: 119°–121° C.
IR(KBr): 2101, 1713, 1645, 1481, 1438, 1260, 1101, 843, 643 cm$^{-1}$.
$^1$H-NMR(CDCl$_3$) δ: 0.98(3H, t, J=7.3 Hz), 1.45(6H, s), 1.55–1.65 (2H, m), 2.46(2H, t, J=7.3 Hz), 2.94(1H, dd, J=6.8, 15.5 Hz), 3.25(1H, dd, J=8.5, 15.5 Hz), 3.45(2H, d, J=5.1 Hz), 5.00(1H, m), 6.82(1H, s), 8.20(1H, br. s).

(7) 2-Aminomethyl-8,8-dimethyl-5-(n-propyl)-2,3,7,8-tetrahydro-6H-furo[2,3-e] indol -7 -one•hydrochloride
Yield: 69.7%, slight yellow needles
mp: 282°–284° C.
IR(KBr): 3440, 1709, 1647, 1482, 1460, 1436, 1247, 1097, 981, 640 cm$^{-1}$.
$^1$H-NMR(D$_2$O) δ: 0.91(3H, t, J=7.3 Hz), 1.40(3H, s), 1.42(3H, s), 1.55(2H, septet, J=7.3 Hz ), 2.51 (2H, t, J=7.3 Hz), 2.96(1H, dd, J=7.0, 17.0 Hz), 3.25–3.50(3H, m), 5.15(1H, m), 7.03(1H, s).

Example 28

The following compounds were prepared in the same manner as in Examples 1 and 2.

(1) N-Benzyl-2-n-butyl-5-methoxyaniline

IR(Cap.): 2916, 1611, 1584, 1512, 1450, 1292, 1206, 1164 cm$^{-1}$.

$^1$H-NMR(CDCl$_3$) δ: 0.93(3H, t, J=7.5 Hz), 1.22–1.65(4H, m), 2.43 (2H, t, J=7.5 Hz), 3.73(3H, s), 4.36(2H, s), 6.22–6.32(2H, m), 6.98(1H, d, J=7.7 Hz), 7.24–7.46 (6H, m).

(2) N-Benzyl-2-bromo-2'-n-butyl-5'-methoxyisobutyranilide

R(KBr): 2915, 1635, 1607, 1491, 1285, 1165 cm$^{-1}$.

$^1$H-NMR(CDCl$_3$) δ: 0.96(3H, t, J=7.6 Hz), 1.28–1.70(4H, m), 1.46 (3H, s), 1.96(3H, s), 2.48(2H, t, J=7.8 Hz), 3.58 (3H, s), 3.89(1H, br.), 5.73(1H, d, J=14.3 Hz), 6.55 (1H, br. s), 6.85(1H, dd, J=2.9, 8.6 Hz), 7.22(1H, d, J=8.6 Hz), 7.28(5H, s).

(3) 1-Benzyl-7-n-butyl-2,3-dihydro-3,3-dimethyl-4-hydroxy-1H-indol-2-one

IR(CHCl$_3$): 1691, 1626, 1604, 1441, 1380, 1353, 1264 cm$^{-1}$.

$^1$H-NMR(CDCl$_3$) δ: 0.87(3H, t, J=7.5 Hz), 1.16–1.63(4H, m), 1.58 (6H, s), 2.43(2H, t, J=7.6 Hz), 5.16(2H, s), 5.90 (1H, s), 6.45(1H, d, J=8.3 Hz), 6.80(1H, d, J=8.3 Hz), 7.22–7.40(5H, m).

(4) 7-n-Butyl-2,3-dihydro-3,3-dimethyl-4-hydroxy-1H-indol-2-one

IR(CHCl$_3$): 2920, 1705, 1624, 1502, 1443, 1380 cm$^{-1}$.

$^1$H-NMR (CDCl$_3$) δ: 0.94(3H, t, J=7.1 Hz), 1.24–1.68(5H, m), 1.51 (6H, s), 2.50(2H, t, J=7.1 Hz), 6.40(1H, d, J=8.5 Hz), 6.87(1H, d, J=8.5 Hz), 8.28(1H, br. s).

(5) 4-Allyloxy-7-n-butyl-2,3-dihydro-3,3-dimethyl-1H-indol-2-one

IR(KBr): 2920, 1700, 1605, 1500, 1455, 1432, 1267 cm$^{-1}$.

$^1$H-NMR(CDCl$_3$) δ: 0.95(3H, t, J=7.1 Hz), 1.32–1.70(4H, m), 1.50 (6H, s), 2.53(2H, t, J=7.1 Hz), 4.56(2H, d, J=5.1 Hz), 5.25–5.50(2H, m), 6.08(1H, m), 6.50(1H, d, J=8.8 Hz), 6.95(1H, d, J=8.8 Hz), 8.40(1H, br. s).

(6) 5-Allyl-7-n-butyl-2,3-dihydro-3,3-dimethyl-4-hydroxy-1H-indol-2-one mp: 109°–111° C.

IR(KBr): 2950, 1705, 1623, 1482, 1458, 1431, 1376, 1259 cm$^{-1}$.

$^1$H-NMR(CDCl$_3$) δ: 0.94(3H, t, J=7.1 Hz), 1.22–1.65(4H, m), 1.49 J=7.3 Hz), 4.90–5.34(3H, m), 6.04(1H, m), 6.77(1H, s), 8.40(1H, s).

(7) 2-Bromomethyl-5-n-butyl-8,8-dimethyl-2,3,7,8-tetrahydro-6H-furo[2,3-e] indol-7-one mp: 155°–157° C.

IR(KBr): 2925, 1706, 1640, 1477, 1457, 1433 cm$^{-1}$.

$^1$H-NMR(CDCl$_3$) δ: 0.95(3H, t, J=7.1 Hz), 1.32–1.67(4H, m), 1.46 (6H, s), 2.51(2H, t, J=7.1 Hz), 3.05(1H, dd, J=6.3, 15.7 Hz), 3.34(1H, dd, J=9.2, 15.7 Hz), 3.42–3.66(2H, m), 5.04(1H, m), 6.83(1H, s), 8.54(1H, br. s).

(8) 2-Azidomethyl-5-n-butyl-8,8-dimethyl-2,3,7,8-tetrahydro-6H-furo[2,3-e] indol-7-one mp: 108°–109° C.

IR(KBr): 2943, 2089, 1700, 1635, 1431, 1250 cm$^{-1}$.

$^1$H-NMR(CDCl$_3$) δ: 0.95(3H, t, J=7.1 Hz), 1.12–1.72(4H, m), 1.46 (6H, s), 2.51(2H, t, J=7.4 Hz), 2.95(1H, dd, J=7.4, 15.4 Hz), 3.27(1H, dd, J=9.7, 15.4 Hz), 3.46(2H, d, J=5.2 Hz), 5.03(1H, m), 6.83(1H, s), 8.74(1H, br. s).

(9) 2-Aminomethyl-5-n-butyl-8,8-dimethyl-2,3,7,8-tetrahydro-6H-furo[2,3-e] indol-7-one mp: 105°–107° C.

2Aminomethyl-5-n-butyl-8,8-dimethyl-2,3,7,8-tetrahydro-6H-furo[ 2,3-e]indol-7-one•hydrochloride mp: 262°–268° C. (Decomposed).

IR(KBr): 2916, 1697, 1640, 1478, 1457, 1431, 1310, 1241, 1091 cm$^{-1}$.

$^1$H-NMR(CD$_3$OD) δ: 0.93(3H, t, J=7.2 Hz), 1.39(3H, s), 1.28–1.57 (4H, m), 1.43(3H, s), 2.52(2H, t, J=7.4 Hz), 2.92 (1H, dd, J=7.3, 15.6 Hz), 3.15–3.40(3H, m), 5.03(1H, m), 6.89(1H, s).

Example 29

The following compounds were prepared in the same manner as in Examples 1 and 2.

(1) 2-Benzylamino-4-methoxy-1-n-pentylbenzene

IR(neat): 3440, 2928, 1617, 1586, 1518, 1454, 1209, 1169, 1047, 698 $^{-1}$.

$^1$H-NMR(CDCl$_3$) δ: 0.96(3H, t, J=7.3 Hz), 1.34–1.48(4H, m), 1.59–1.73(2H, 2.49(2H, t, J=8.1 Hz), 3.79 (3H, s), 3.97–4.16(1H, br.), 4.05(2H, s), 6.27–6.35 (2H, m), 7.02(1H, d, J=8.1 Hz), 7.30–7.48 (5H, m).

(2) N-Benzyl-2-bromo-5'-methoxy-2'-n-pentylisobutyranilide

IR(neat): 2930, 2859, 1645, 1610, 1505, 1467, 1390, 1288, 1171, 1039, 700 cm$^{-1}$.

$^1$H-NMR(CDCl$_3$) δ: 0.89–1.02(3H, 1.32–1.74(9H, m), 1.98(3H, s), 2.49(2H, t, J=8.1 Hz), 3.58(3H, s), 3.89(1H, m), 5.72(1H, d, J=14.2 Hz), 6.54(1H, d, J=2.2 Hz), 6.85(1H, dd, J=2.2, 8.6 Hz), 7.21 (1H, d, J=8.6 Hz), 7.18–7.34(5H, m).

(3) 1-Benzyl-2,3-dihydro-3,3-dimethyl-4-hydroxy-7-n-pentyl-1H-indol-1-2 -one

IR(firm): 3019, 2401, 1699, 1444, 1216, 767, 669 cm$^{-1}$.

$^1$H-NMR(CDCl$_3$) δ: 0.85(3H, J=8.3 Hz), 1.10–1.55(6H, 1.57 (6H, s), 2.43(2H, t, J=8.3 Hz), 5.14(2H, s), 5.40 (1H, s), 6.41(1H, d, J=8.3 Hz), 6.79(1H, d, J=8.3 Hz), 7.10–7.30(5H, m).

(4) 2,3-Dihydro-3,3-dimethyl-4-hydroxy-7-(n-pentyl)-1H-indol-2-one

IR(firm): 3308, 1683, 1506, 1385, 1163, 1090, 806 cm$^{-1}$.

$^1$H-NMR(CDCl$_3$) δ: 0.89(3H, t, J=7.8 Hz), 1.20–1.70(6H, m), 1.50 (6H, s), 2.47(2H, t, J=7.6 Hz), 5.20(1H, br.), 6.38 (1H, d, J=8.3 Hz), 6.86(1H, d, J=8.3 Hz), 8.20(1H, br. s).

(5) 4-Allyloxy-2,3-dihydro-3,3-dimethyl-7-(n-pentyl)-1H-indol-2-one

Yield: 63.6%, colorless needles mp: 116°–117° C.

IR(KBr): 3277, 1656, 1532, 1494, 1287, 1231, 1042, 836, 717 cm$^{-1}$.

$^1$H-NMR(CDCl$_3$) δ: 0.90(3H, t, J=7.8 Hz), 1.20–1.70(6H, m), 1.49 (6H, s), 2.49(2H, t, J=7.3 Hz), 4.55(2H, d, J=4.9 Hz), 5.28(1H, dd, J=1.5, 10.5 Hz), 5.42(1H, dd, J=1.5, 17.2 Hz), 6.10(1H, m), 6.50(1H, d, J=8.6 Hz), 6.94(1H, d, J=8.6 Hz), 8.15(1H, br. s).

(6) Allyl-2,3-dihydro-3,3-dimethyl-4-hydroxy-7-(n-pentyl)-1H-indol-2-one

Yield: 64.8%

IR(firm): 3207, 1705, 1627, 1487, 1455, 1262, 1117, 915 $^{-1}$.

$^1$H-NMR(CDCl$_3$) δ: 0.90(3H, t, J=6.8 Hz), 1.20–1.60(6H, m), 1.49 (6H, s), 2.45(2H, t, J=7.0 Hz), 3.37(2H, d, J=6.6 Hz), 5.06(1H, s), 5.20–5.35(2H, m), 6.05(1H, m), 6.74(1H, s), 7.80(1H, br. s).

(7) 2-Bromomethyl-8,8-dimethyl-(5-n-pentyl)-2,3,7,8-tetrahydro-6H-furo[2,3-e] indol-7 -one Yield: 63.2%, colorless needles mp: 160°–161° C.

IR(KBr): 1713, 1645, 1436, 1243, 1098, 1004, 764, 645 $^{-1}$.

$^1$H-NMR(CDCl$_3$) δ: 0.90(3H, t, J=6.8 Hz), 1.25–1.60(6H, m), 1.44 (6H, s), 2.45(2H, t, J=7.3 Hz), 3.04(1H, dd, J=5.9, 15.6 Hz), 3.33(1H, dd, J=9.0, 15.6 Hz), 3.47–3.63(2H, m), 5.01(1H, m), 6.81(1H, s), 7.85(1H, br. s).

(8) 2-Azidomomethyl-8,8-dimethyl-(5-n-pentyl)-2,3,7,8-tetrahydro-6H-furo[2,3-e]indol- 7-one Yield: 100%, pale yellow powder mp: 92°–94° C.

IR(KBr): 2105, 1702, 1639, 1482, 1464, 1434, 1257, 1098, 875, 641 cm$^{-1}$.

$^1$H-NMR(CDCl$_3$) δ: 0.90(3H, t, J=7.0 Hz), 1.20–1.65(6H, m), 1.45 (6H, s), 2.47(2H, t, J=7.3 Hz), 2.94(1H, dd, J=7.6, 15.5 Hz), 3.26(1H, dd, J=9.3, 15.5 Hz), 3.45(2H, d, J=5.1 Hz), 5.05(1H, m), 6.82(1H, s), 8.25(1H, br. s).

(9) 2-Aminomethyl-8,8-dimethyl-(5-n-pentyl)-2,3,7,8-tetrahydro-6H-furo[2,3-e] indol-7-one•hydrochloride Pale yellow powder, mp: 250°–256° C. (decomposed).

IR(KBr): 3432, 1709, 1645, 1482, 1460, 1247, 1097, 982, 640 cm$^{-1}$.

$^1$H-NMR(CD$_3$OD) δ: 0.90(3H, t, J=6.8 Hz), 1.20–1.60(6H, m), 1.39 (3H, s), 1.42(3H, s), 2.51(2H, t, J=7.8 Hz), 2.93 (1H, dd, J=7.6, 15.6 Hz), 3.15–3.45(3H, m), 5.05(1H, m), 6.89(1H, s).

Example 30

The following compounds were prepared in the same manner as in Examples 1 and 2.

(1) N-Benzyl-2-bromo-2',3'-dimethyl-5'-ethoxyisobutyranilide mp: 66°–68° C.

IR(Cap. ): 2966, 2920, 1734, 1638, 1467, 1388, 1308, 1160 cm$^{-1}$.

$^1$H-NMR(CDCl$_3$) δ: 1.26(3H, t, J=7.1 Hz), 1.47(3H, S), 1.94(3H, s), 2.03(3H, s), 2.24(3H, s), 3.66–3.96(3H, m), 5.61(1H, d, J=13.9 Hz), 6.41(1H, d, J=2.2 Hz), 6.70 (1H, d, J=2.2 Hz), 7.17–7.30(5H, m).

(2) 1-Benzyl-2,3-dihydro-4-hydroxy-3,3,6,7-tetramethyl-1H-indol-2-one mp: 145°–147° C.

IR(KBr): 3171, 1663, 1610, 1432, 1352, 1283, 1231, 1122 cm$^{-1}$.

$^1$H-NMR(CDCl$_3$) δ: 1.56(6H, s), 2.08(3H, s), 2.13(3H, s), 5.23 (2H, s), 5.41(1H, br. s), 6.36(1H, s), 7.10–7.38(5H, m).

(3) 2,3-Dihydro-4-hydroxy-3,3,6,7-tetramethyl-1H-indol-2-one mp: 256°–260° C. (decomposed).

IR(KBr): 3146, 1670, 1634, 1440, 1383, 1310, 1236, 1090 cm$^{-1}$.

$^1$H-NMR(CDCl$_3$–CD$_3$OD) δ: 1.46(6H, s), 2.08(3H, s), 2.19(3H, s), 6.33(1H, s).

(4) 4-Allyloxy-2,3-dihydro-3,3,6,7-tetramethyl-1H-indol-2-one mp: 152°–155° C.

IR(KBr): 3143, 1695, 1626, 1602, 1304, 1254, 1121 cm$^{-1}$.

$^1$H-NMR(CDCl$_3$) δ: 1.48(6H, s), 2.12(3H, s), 2.26(3H, s), 4.55 (2H, d, J=4.8 Hz), 5.24–6.18(3H, m), 6.40(1H, s), 8.55(1H, br. s).

(5) 5-Allyl-2,3-dihydro-4-hydroxy-3,3,6,7-tetramethyl-1H-indol-2-one mp: 145°–147° C.

IR(KBr): 3143, 1695, 1626, 1602, 1453, 1304, 1121 $^{-1}$.

$^1$H-NMR(CDCl$_3$) δ: 1.49(6H, s), 2.15(3H, s), 2.20(3H, s), 3.43 (2H, d, J=7.6 Hz), 4.90(1H, m), 5.04–5.17(2H, m), 5.96(1H, m), 8.62(1H, br. s).

(6) Bromomethyl-2,3,7,8-tetrahydro-4,5,8,8-tetramethyl-6H-furo[2,3-e]indol-7-one mp: 225°–230° C. (Decomposed).

IR(KBr): 1691, 1642, 1424, 1241, 1106 cm$^{-1}$.

$^1$H-NMR(CDCl$_3$) δ: 1.44(6H, s), 2.10(3H, s), 2.16(3H, s), 3.00 (1H, dd, J=5.0, 13.8 Hz), 3.29(1H, dd, J=8.1, 13.8 Hz), 3.51(1H, dd, J=6.1, 9.1 Hz), 3.62 (1H, dd, J=4.3, 9.1 Hz), 5.04(1H, m), 8.18(1H, br. s).

(7) 2-Azidomethyl-2,3,7,8-tetrahydro-4,5,8,8-tetramethyl-6H-furo[2,3-e]indol-7-one mp: 219°–222° C. (Decomposed).

IR(KBr): 3165, 2087, 1690, 1645, 1447, 1423, 1321, 1264 cm$^{-1}$.

$^1$H-NMR(CDCl$_3$) δ: 1.44(6H, s), 2.12(3H, s), 2.15(3H, s), 2.90 (1H, dd, J=6.3, 15.4 Hz), 3.24(1H, dd, J=9.4, 15.4 Hz), 3.46(2H, d, J=4.9 Hz), 5.02(1H, m), 8.55 (1H, br. s).

(8) 2-Aminomethyl-2,3,7,8-tetrahydro-4,5,8,8-tetramethyl-6H-furo[2,3-e]indol-7-one mp: 234°–237° C.

2-Aminomethyl-2,3,7,8-tetrahydro-4,5,8,8-tetramethyl-6H-furo[2,3-e]indol-7-one•hydrochloride mp: 206°–211° C. (Decomposed).

IR(KBr): 2894, 1685, 1646, 1424, 1247, 1101 cm$^{-1}$.

$^1$H-NMR(D$_2$O) δ: 1.36(3H, s), 1.39(3H, s), 2.11(3H, s), 2.17 (3H, s), 2.93(1H, dd, J=6.1, 14.2 Hz), 3.19–3.50(3H, m), 5.15(1H, m).

Example 31

(2R*,3R*)-2-(t-butoxycarbonylamino)methyl-2,3,7,8-tetrahydro-3,5,8,8-tetramethyl-6 H-furo[2,3-e]indol-7-one 400 mg (1.54 mmol) of (2R*,3R*)-2-aminomethyl-2,3,7, 8-tetrahydro-3,5,8,8-tetramethyl-6 H-furo[2,3e]indol-7-one and 437 mg (2.00 mmol) of di-t-butyldicarbonate were added to 7 ml of tetrahydrofuran, and the mixture was stirred for 1.5 hours at room temperature. After the reaction, the solvent was evaporated. The residue was recrystallized from a mixed solvent of chloroform and ether to obtain 493 mg (yield, 89.0%) of a colorless powder of the title compound.

IR(KBr): 1709, 1687, 1537, 1460, 1267, 1170, 1072, 887, 642 cm$^{-1}$.

$^1$H-NMR(CDCl$_3$) δ: 1.32(3H, d, J=6.7 Hz), 1.44(3H, s), 1.45(3H, s), 1.46(9H, s), 2.19(3H, s), 3.10–3.70(3H, m), 4.35(1H, m), 4.85(1H, m), 6.75(1H, s), 7.93(1H, br. s).

Example 32

(2R*,3S*)-2-(t-butoxycarbonylamino)methyl-2,3,7,8 -tetrahydro-3,5,8,8-tetramethyl-6H-furo[2,3-e]indol-7-one The title compound was prepared in the same manner as in Example 31.

Yield: 91.2%, pale yellow powder, mp: 233°–234° C. (chloroform-methanol).

IR(KBr): 1705, 1645, 1512, 1482, 1457, 1258, 1168, 1094, 764, 639 cm$^{-1}$.

$^1$H-NMR(CDCl$_3$) δ: 1.22(3H, d, J=7.0 Hz), 1.44(3H, s), 1.45(3H, s), 1.47(9H, s), 2.18(3H, s), 3.10–3.70(3H, m), 4.75–4.90(2H, m), 6.75(1H, s), 7.80(1H, br. s).

Example 33

(2R*,3R*)-2-(t-butoxycarbonylamino)methyl-2,3,7,8-tetrahydro-3,5,8,8-tetramethyl-6 H-furo[2,3-e]indol-7-thione 460 mg (1.28 mmol) of (2R*,3R*)-2-(t-butoxycarbonylamino)methyl-2,3,7,8 -tetrahydro-3,5,8,8-tetramethyl-6H-furo[2,3-e]indol-7-one and 667 mg (1.66 mmol) of Lawesson's reagent were added to 20 ml of toluene, and the mixture was stirred for one hour at 110° C., then the solvent was evaporated. The residue obtained was purified by column chromatography (silica gel, chloroform) and recrystallized from a mixed solvent of chloroform and n-hexane to obtain 370 mg (yield, 77.0%) of colorless needles of the title compound.

mp: 203°–204° C.

IR(KBr): 3338, 1687, 1537, 1494, 1268, 1169, 1068, 885 cm$^{-1}$.

$^1$H-NMR(CDCl$_3$) δ: 1.34(3H, d, J=6.8 Hz), 1.46(9H, s), 1.50(3H, s), 1.51(3H, s), 2.26(3H, s), 3.10–3.70(3H, m), 4.36(1H, m), 4.85(1H, m), 6.79(1H, s), 9.62(1H, br. s).

Example 34

(2R*,3S*)-2-(t-butoxycarbonylamino)methyl-2,3,7,8-tetrahydro-3,5,8,8-tetramethyl-6 H-furo[2,3-e]indol-7-thione This compound was prepared in the same manner as in Example 33

Yield: 74.5%, pale yellow powder, mp: 215°–216° C. (chloroform-n-hexane).

IR(KBr): 3468, 2974, 1717, 1641, 1476, 1253, 1168, 1087, 1063, 871 cm$^{-1}$.

$^1$H-NMR(CDCl$_3$) δ: 1.24(3H, d, J=7.3 Hz), 1.48(9H, s), 1.50(3H, s), 1.51(3H, s), 2.26(3H, s), 3.10–3.70(3H, m), 4.85(1H, m), 6.79(1H, s), 9.60(1H, br. s).

Example 35

(2R*,3R*)-2-aminomethyl-2,3,7,8-tetrahydro-3,5,8,8-tetramethyl-6H-furo[2,3-e] indol-7-thione•hydrochloride 370 mg (0.98 mmol) of (2R*,3R*)-2-(t-butoxycarbonylamino)methyl-2,3,7,8 -tetrahydro-3,5,8,8-tetramethyl-6H-furo[2,3-e]indol-7-thione was added to 4 ml of 4N hydrogen chloride solution in ethyl acetate, and the mixture was stirred for 75 minutes at room temperature. n-Hexane was added to the reaction mixture, and crystals were collected by filtration. The crystals were recrystallized from a mixed solvent of methanol and ether to obtain 245 mg (yield, 79.7%) of a pale yellow powder of the title compound.

mp: >300° C.

IR(KBr): 3432, 1642, 1493, 1445, 1086, 1044, 977, 763 cm$^{-1}$.

$^1$H-NMR(CD$_3$OD) δ: 1.38(3H, d, J=6.8 Hz), 1.43(3H, s), 1.46(3H, s), 2.27(3H, s), 3.20–3.45(3H, m), 4.55(1H, m), 6.90(1H, s).

Example 36

(2R*,3S*)-2-aminomethyl-2,3,7,8-tetrahydro-3,5,8,8-tetramethyl-6H-furo[2,3-e] indol-7-thione•hydrochloride This compound was synthesized in the same manner as in Example 35.

Yield: 90.9%, pale yellow powder, mp: >300° C. (methanol-ether).

IR(KBr): 3473, 1642, 1495, 1456, 1275, 1087, 1040, 947, 882, 771 cm$^{-1}$.

$^1$H-NMR(CD$_3$OD) δ: 1.21(3H, d, J=7.1 Hz), 1.43(3H, s), 1.46(3H, s), 2.27(3H, s), 3.18–3.66(3H, m), 4.95(1H, m), 6.92(1H, s).

Example 37

(2R*,3S*)-2-t-butoxycarbonylaminomethyl-2,3,5,8,8-pentamethyl-2,3,7,8-tetrahydro-6 H-furo[2,3-e]indol-7-one This compound was synthesized in the same manner as in Example 31.

Yield: 85.4%, colorless crystals, mp: 181° C.

IR(KBr): 3184, 2961, 1696, 1642, 1451, 1268, 1160 cm$^{-1}$.

$^1$H-NMR(CDCl$_3$) δ: 1.25(3H, d, J=7.3 Hz), 1.46(18H, s), 2.19(3H, s), 3.10–3.51(3H, m), 4.69(1H, br. s), 6.71(1H, s), 8.05(1H, br. s).

Example 38

(2R*,3S*)-2-t-butoxycarbonylaminomethyl-2,3,5,8,8-pentamethyl-2,3,7,8-tetrahydro-6 H-furo[2,3-e]indol-7-thione This compound was synthesized in the same manner as in Example 33.

Yield: 72.8%, colorless powder, mp: 177°–183° C.

IR(KBr): 2957, 2910, 1706, 1638, 1494, 1447, 1271, 1163 cm$^{-1}$.

$^1$H-NMR(CDCl$_3$) δ: 1.27(3H, d, J=7.3 Hz), 1.46(12H, s), 1.48(3H, s), 1.50(3H, s), 2.26(3H, s), 3.10–3.52(3H, m), 4.71(1H, br. s), 6.75(1H, s), 9.65(1H, br. s).

Example 39

(2R*,3S*)-2-aminomethyl-2,3,5,8,8-pentamethyl-2,3,7,8-tetrahydro-6H- furo[ 2,3-e]indol-7-thione This compound was synthesized in the same manner as in Example 35.

Yield: 99.6%, colorless needles, mp: 262°–270° C. (Decomposed).

IR(KBr): 2900, 1738, 1636, 1482, 1446, 1263, 1086, 1054 cm$^{-1}$.

$^1$H-NMR(CD$_3$OD) δ: 1.28(3H, d, J=7.3 Hz), 1.43(3H, s), 1.46(3H, s), 1.57(3H, s), 2.28(3H, s), 3.16(2H, s), 3.34(1H, m), 6.90(1H, s).

Example 40

(1) 2-(t-Butoxycarbonylamine)methyl-2,3,7,8-tetrahydro-5,8,8-trimethyl-6 H-furo[2,3-e]indol-7-one This compound was synthesized in the same manner as in Example 31.

Yield: 87.7%, colorless powder, mp: 181°–182° C.

$^1$H-NMR(CDCl$_3$) δ: 1.44(6H, s), 1.46(9H, s), 2.18(3H, s), 2.83(1H, dd, J=6.8, 15.6 Hz), 3.19(1H, dd, J=9.3, 15.6 Hz), 3.26–3.62(2H, m), 4.75–4.98(2H, m), 6.80(1H, s), 8.11(1H, br. s).

IR(KBr): 3304, 3176, 1709, 1689, 1643, 1458, 1256, 1087.

(2) 2-(t-Butoxycarbonylamine)methyl-2,3,7,8-tetrahydro-5,8,8-trimethyl-6H-furo[2,3 -e]indol-7-thione This compound was synthesized in the same manner as in Example 33.

Yield: 74.9%, colorless prisms, mp: 163°–165° C. (ether-hexane).

$^1$H-NMR(CDCl$_3$) δ: 1.46(9H, s), 1.50(6H, s), 2.26(3H, s), 2.85 (1H, dd, J=7.3, 16.1 Hz), 3.21(1H, dd, J=8.3, 16.1 Hz), 3.26–3.52(2H, m), 4.74–5.00(2H, m), 6.85 (1H, s), 9.90(1H, s).

IR(KBr): 3301, 1688, 1537, 1439, 1319, 1249, 1168, 1079, 784.

(3) 2-Aminomethyl-2,3,7,8-tetrahydro-5,8,8-trimethyl-6H-furo[2,3-e]indol-7-thione•hydrochloride This compound was synthesized in the same manner as in Example 35.

Yield: 84.6%, pale yellow powder, mp: >300° C.

$^1$H-NMR(CD$_3$OD) δ: 1.42(3H, s), 1.45(3H, s), 2.26(3H, s), 2.94 (1H, dd, J=6.6, 16.0 Hz), 3.15–3.40(3H, m), 4.98–5.12(1H, m), 6.93(1H, s).

IR(KBr): 1642, 1493, 1441, 1313, 1273, 1249, 1083.

Example 41

(1) 2-(t-Butoxycarbonylamino)methyl-2,3,7,8-tetrahydro-2,5,8,8-tetramethyl-6H-furo[ 2,3-e]indol-7-one This compound was synthesized in the same manner as in Example 31.

Yield: 91.0%, colorless powder, mp: 204°–205° C. (n-hexane).

$^1$H-NMR(CDCl$_3$) δ: 1.41(3H, s), 1.43(15H, s), 2.18(3H, s), 2.83(1H, d, J=15.6 Hz), 3.04(1H, d, J=15.6 Hz), 3.40(2H, d, J=5.9 Hz), 4.73(1H, m), 6.79(1H, s).

IR (KBr): 3330, 1701, 1538, 1276, 1170, 1087.

(2) 2-(t-Butoxycarbonylamino)methyl-2,3,7,8-tetrahydro-2,5,8,8-tetramethyl-6 H-furo[2,3-e]indol-7-thione This compound was synthesized in the same manner as in Example 33.

Yield: 55.2%, pale yellow prisms, mp: 191°–192° C. (ether-n-hexane).

$^1$H-NMR(CDCl$_3$) δ: 1.41(3H, s), 1.43(9H, s), 1.49(3H, s), 1.50(3H, s), 2.26(3H, s), 2.85(1H, d, J=15.9 Hz), 3.08(1H, d, J=15.9 Hz), 3.41(2H, d, J=6.4 Hz), 4.73(1H, m), 6.83(1H, s).

IR(KBr): 3374, 1714, 1689, 1637, 1525, 1495, 1475.

(3) 2-Aminomethyl-2,3,7,8-tetrahydro-2,5,8,8-tetramethyl-6H-furo[2,3-e]indol-7 -thione•hydrochloride This compound was synthesized in the same manner as in Example 35.

Yield: 91.2%, pale yellow powder, mp: >300° C.

$^1$H-NMR(CD$_3$OD) δ: 1.40(3H, s), 1.44(3H, s), 1.53(3H, s), 2.26 (3H, s), 3.03(1H, d, J=15.9 Hz), 3.17(1H, d, J=15.9 Hz), 3.26(2H, s), 6.92(1H, s).

IR(KBr): 3154, 1639, 1493, 1441, 1274, 1084.

Example 42

(1) (2R*,3R*)-2-(t-butoxycarbonylamino)methyl-2,3,5,8,8-pentamethyl-2,3,7,8-tetrahydro-6 H-furo[2,3-e]indol-7-one This compound was synthesized in the same manner as in Example 27.

Yield: 88.8%, colorless powder, mp: 135–136° C.

$^1$NMR (CDCl$_3$) δ: 1.23(3H, d, J=7.1 Hz), 1.23(3H, s), 1.43(3H, s), 1.44(12H, s), 2.19(3H, s), 3.19(1H, q, J=7.1 Hz), 3.39(2H, d, J=6.4 Hz), 4.77(1H, m), 6.73 (1), s).

IR(KBr): 3427, 3189, 1704, 1642, 1525, 1173.

(2) (2R*,3R*)-2-(t-butoxycarbonylamino)methyl-2,3,5,8,8-pentamethyl-2,3,7,8-tetrahydro-6 H-furo[2,3-e]indol-7-thione This compound was synthesized in the same manner as in Example 33.

Yield: 67.1%, pale yellow prisms, mp: 171°–172° C. (ether-n-hexane).

$^1$H-NMR(CDCl$_3$) δ: 1.24(3H, s), 1.24(3H, d, J=6.8 Hz), 1.44(9H, s), 1.48(3H, s), 1.50(3H, s), 2.27(3H, s), 3.22(1H, q, J=6.8 Hz), 3.40(2H, d, J=6.2 Hz), 4.78(1H, m), 6.77(1H, s), 9.83(1H, br. s).

IR(KBr): 3387, 1713, 1689, 1637, 1496, 1367, 1175, 1087.

(3) (2R*,3R*)-2-aminomethyl-2,3,5,8,8-pentamethyl-2,3,7,8-tetrahydro-6 H-furo[2,3-e]indol-7thione•hydrochloride This compound was synthesized in the same manner as in Example 35.

Yield: 73.3%, colorless powder, mp: 295°–296° C. (decomposed) (ethanol).

$^1$H-NMR(CD$_3$OD) δ: 1.29(3H, d, J=7.1 Hz), 1.36(3H, s), 1.41 (3H, s), 1.44(3H, s), 2.27(3H, s), 3.25(2H, s), 6.89(1H, s).

IR(KBr): 1643, 1502, 1477, 1449, 1273, 1092, 1051, 890.

Example 43

(1) 2-(t-Butoxycarbonylamino)methyl-3-ethyl-2,3,7,8-tetrahydro-5,8,8-trimethyl-6 H-furo[2,3-e]indol-7-one This compound was synthesized in the same manner as in Example 27.

Yield: 92.8%, colorless prisms, mp: 210°–212° C. (n-hexane).

$^1$H-NMR(CDCl$_3$) δ: 1.06(3H, t, J=7.3 Hz), 1.44(3H, s), 1.45(3H, s), 1.47(9H, s), 1.62(2H, q, J=7.3 Hz), 2.22(3H, s), 3.10–3.30(2H, m), 3.68(1H, m), 4.68–4.92(2H, m), 6.80(1H, s), 8.39(1H, s).

IR(KBr): 3466, 1705, 1644, 1481, 1257, 1066.

(2) 2-(t-Butoxycarbonylamino)methyl-3-ethyl-2,3,7,8-tetrahydro-5,8,8-trimethyl-6 H-furo[2,3-e]indol-7-thione This compound was synthesized in the same manner as in Example 33.

Yield: 70.8%, colorless prisms, mp: 219°–220° C. (decomposed) (ether-n-hexane).

$^1$H-NMR(CDCl$_3$) δ: 1.06(3H, t, J=7.8 Hz), 1.44(9H, s), 1.50(3H, s), 1.51(3H,s), 1.55–1.74(2H, m), 2.27(3H, s), 3.12–3.35(2H, m), 3.70(1H, br. s), 4.70–4.94(2H, m), 6.84(1H, s), 9.83(1H, br. s).

IR(KBr): 3461, 1718, 1638, 1496, 1448, 1255, 1166, 1060.

(3) 2-Aminomethyl-3-ethyl-2,3,7,8-tetrahydro-5,8,8-trimethyl-6H-furo[2,3-e] indol-7-thione•hydrochloride This compound was synthesized in the same manner as in Example 35.

Yield: 60.9%, colorless prisms, mp: >300° C. (methanol-ethanol).

$^1$H-NMR(CD$_3$OD) δ: 1.02(3H, t, J=7.3 Hz), 1.43(3H, s), 1.45 (3H, s), 1.61(2H, q, J=7.3 Hz), 2.28(3H, s), 3.22–3.48(3H, m), 3.43(1H, dd, J=2.4, 13.2 Hz), 5.10 (1H, m), 6.96(1H, s).

IR(KBr): 1641, 1482, 1451, 1270, 1089, 1039.

Example 44

(2R*,3S*)-2-(t-butoxycarbonylamino)methyl-7-methylthio-2,3,5,8,8-pentamethyl-8 H-furo[2,3-e]indole 180 mg (0.46 mmol) of (2R*,3S*)-2-(t-butoxycarbonylamino)methyl-2,3,5,8,8-pentamethyl- 2,3,7,8-tetrahydro-6H-furo[2,3-e]indol-7-thione and 2.05 g (14.4 mmol) of methyl iodide were added to 9 ml of anhydrous tetrahydrofuran, and the mixture was stirred for 70 minutes at room temperature under a stream of argon. The reaction mixture was concentrated and the residue was purified by column chromatography (silica gel, chloroform) to obtain 128 mg (yield 65.6%) of a syrup of the title compound.

IR(CHCl$_3$): 2959, 1705, 1501, 1451, 1365, 1161 cm$^{-1}$.

$^1$H-NMR(CDCl$_3$) δ: 1,27(3H, d, J=7.1 Hz). 1.39(3H, s), 1.40(3H, s), 1.45(9H, S), 1.56(3H, s), 2.46(3H, s), 2.64(3H, s), 3.10–3.50 (3H, m), 4.65(1H, m), 6.79(1H, s).

Example 45

(2R*,3S*)-2-(t-butoxycarbonylamino)methyl-7-imino-2,3, 5,8,8-pentamethyl-2,3,7,8 -tetrahydro-6H-furo[2,3-e]indole 120 mg (0.30 mmol) of (2R*,3S*)-2-(t-butoxycarbonylmino)methyl-7-methylthio-2,3,5,8,8 -pentamethyl-8H-furo[2,3-e]indole was dissolved in saturated ammonia solution in methanol, and the mixture was heated for 3 hours in a sealed tube at 90°–100° C. The solvent was evaporated to obtain a crude product, which was again dissolved in 2 ml of saturated ammonia solution in methanol to repeat the same reaction. This procedure was repeated 8 times, whereupon the solvent was evaporated and the crude product was purified by separation thin layer chromatography (silica gel, 10:1 mixture of chloroform and saturated ammonia in methanol) to obtain 53 mg (yield 47.3%) of a solid of the title compound.

IR(CHCl$_3$): 2955, 1705, 1623, 1451, 1363, 1161, 905 cm$^{-1}$ $^1$H-NMR(CDCl$_3$) δ: 1.26(3H, d, J=7.1 Hz), 1.42(3H, s), 1.43(3H, s),1.45(12H, s), 2.34(3H, s), 3.10–3.50(3H, m), 4.70(1H, m), 6.76(1H, s).

Example 46

(2R*,3S*)-2-aminomethyl-7-imino-2,3,5,8,8-pentamethyl-2,3,7,8-tetrahydro-6 H-furo[2,3-e]indole-dihydrochloride 53 mg (0.14 mmol) of (2R*,3S*)-2-(t-butoxycarbonylamino)methyl-7-imino-2,3,5,8,8 -pentamethyl-2,3,7,8-tetrahydro-6H-furo[2,3-e]indole was added to a mixture of 1 ml of 4N hydrogen chloride solution in dioxane and 0.3 ml of methanol, and the mixture was stirred for 50 minutes at room temperature. After the reaction, the solvent was evaporated and the residue was recrystallized from ethyl acetate-methanol to obtain 29 mg (yield: 52.3%) of a pale yellow powder of the title compound. This compound contained ½ mol of ethyl acetate as crystal solvent.

mp: 294°–300° C. (Decomposed).

IR(KBr): 3375, 2903, 1677, 1646, 1457, 1265, 1100 cm$^{-1}$.

$^1$H-NMR(CD$_3$OD) δ: 1.28(3H, d, J=7.3 Hz), 1.57(3H, s), 1.63(3H, s), 1.67(3H, s), 2.32(3H, s), 3.20–3.55(3H, m), 7.01(1H, s), 1.24(3/2H, t, J=7.0 Hz), 2.01(3/2H, s), 4.10(2/2H, q, J=7.0 Hz).

Example 47

(1) Ethyl 4-allyloxyindole-2-carboxylate 50 mg (0.24 mmol) of ethyl 4-hydroxyindole-2-carboxylate (U.S. Pat. No. 3,705,907), 48 mg (0.29 mmol) of allyl iodide, and 33 mg (0.24 mmol) of potassium carbonate were added to 0.5 ml of N,N-dimethylformamide, and the mixture was stirred for 1 hour and 45 minutes at 50° C. After the reaction, the solvent was evaporated. The residue was dissolved in chloroform, washed with saturated aqueous solution of sodium hydrogen carbonate and brine, and dried over anhydrous sodium sulfate. The solvent was evaporated to obtain 63 mg of a crude product, which was purified by separation thin layer chromatography (silica gel, chloroform: methanol=30:1) to obtain 42 mg (yield: 70.2%) of the target compound. This compound was recrystallized from a mixture of chloroform and n-hexane to obtain light brown needles of the title compound.

mp: 154°–155° C.

IR(KBr): 3308, 1688, 1584, 1517, 1259, 1197, 757 cm$^{-1}$.

$^1$H-NMR(CDCl$_3$) δ: 1.41(3H, t, J=7.3 Hz), 4.38(2H, q, J=7.3 Hz) 4.69(2H, d, J=5.4 Hz), 5.31(1H, d, J=10.3 Hz), 5.49(1H, d, J=17.1 Hz), 6.15(1H, m), 6.51(1H, d, J=8.3 Hz), 7.01(1H, d, J=8.3 Hz), 7.26(1H, t, J=8.3 Hz), 7.38(1H, d, J=2.0 Hz), 8.90(1H, br. s).

(2) Ethyl 5-allyl-4-hydroxyindole-2-carboxylate 2.79 g (11.4 mmol) of ethyl 4-allyloxyindole-2-carboxylate was added to 8.8 g of N,N-dimethylaniline, and the mixture was stirred for 15 minutes at 200° C. under a nitrogen atmosphere. 2.7 g of a crude product was obtained by adding n-hexane to the reaction mixture and collecting deposited crystals by filtration. This crude product was purified by column chromatography (silica gel, chloroform) to obtain 1.4 g (yield: 50.2%) of the target compound. This compound was recrystallized from a mixture of ethyl acetate and n-hexane to obtain colorless needles of the title compound.

mp: 139°–140° C.

IR(KBr): 3310, 1700, 1531, 1351, 1302, 1220, 1215, 765 cm$^{-1}$.

$^1$H-NMR(CDCl$_3$) δ: 1.40(3H, t, J=7.3 Hz). 3.50(2H, d, J=6.5 Hz), 4.40(2H, q, J=7.3 Hz), 5.10–5.20(2H, m), 5.40(1H, br. s), 6.06(1H, m), 6.95(1H, d, J=8.3 Hz), 7.06(1H, d, J=8.3 Hz), 7.29(1H, d, J=2.0 Hz), 8.80(1H, br. s).

(3) 2-Bromomethyl-5,8-dibromo-2,3-dihydro-7-ethoxycarbonyl-6H-furo[2,3-e]indole 50 mg (0.2 mmol) of ethyl 5-allyl-4-hydroxyindole-2-carboxylate and 110 mg (0.62 mmol) of N-bromosuccinimide were added to 4 ml of chloroform, and the mixture was stirred for 35 minutes at room temperature under a nitrogen atmosphere. After the reaction, the solvent was evaporated and the residue was purified by column chromatography (silica gel, 1:1 mixture of chloroform and carbontetrachloride) to obtain 96 mg (yield: 97.7%) of a crude product. This crude product was recrystallized from a mixture of chloroform and n-hexane to obtain a pale yellow powder of the title compound.

mp: 182°–183° C.

IR(KBr): 3279, 1691, 1517, 1314, 1265, 1236 cm$^{-1}$.

$^1$H-NMR(CDCl$_3$) δ: 1.49(3H, t, J=7.0 Hz). 3.19(1H, dd, J=6.5, 15.3 Hz), 3.40–3.80(3H, m), 4.46(2H, q, J=7.0 Hz), 5.25(1H, m), 7.26(1H, s), 8.95(1H, br. s).

(4) 2-Azidomethyl-5,8-dibromo-2,3-dihydro-7-ethoxycarbonyl-6H-furo[2,3-e]indole 2.1 g (4.36 mmol) of 2-bromomethyl-5,8-dibromo-2,3-dihydro-7-ethoxycarbonyl-6H-furo[ 2,3-e]indole and 2.9 g (43.6 mmol) of sodium azide were added to 2 ml of N,N-dimethylformamide, and the mixture was stirred for 3 hours at 60° C. under a nitrogen atmosphere. After the reaction, the solvent was evaporated under reduced pressure. The residue was dissolved in chloroform, washed with water, and dried over anhydrous sodium sulfate. 2.3 g of a crude product was obtained by evaporating the solvent. This crude product was purified by column chromatography (silica gel, chloroform) to obtain 1.9 g (yield: 100%) of a crude product, which was recrystallized from a mixture of ethyl acetate and n-hexane to obtain a pale yellow powder of the title compound.

mp: 140°–142° C.

IR(KBr): 3265, 2087, 1689, 1515, 1494, 1377, 1260 cm$^{-1}$.

$^1$H-NMR(CDCl$_3$) δ: 1.45(3H, t, J=7.3 Hz). 3.07(1H, dd, J=7.3, 15.4 Hz), 3.40(1H, dd, J=9.7, 15.4 Hz), 3.54(2H, d, J=4.9 Hz), 4.46(2H, q, J=7.3 Hz), 5.20(1H, m), 7.30(1H, s), 8.90(1H, br. s).

(5) 2-Aminomethyl-2,3-dihydro-7-ethoxycarbonyl-6H-furo [2,3-e]indole•hydrochloride 1.9 g (4.32 mmol) of 2-azidomethyl-5,8-dibromo-2,3-dihydro-7-ethoxycarbonyl-6H-furo[ 2,3-e]indole was added to 40 ml of N,N-dimethylformamide. After the addition of 2.0 g of 10% palladium-carbon catalyst, the mixture was catalytically hydrogenated for 2 hours at 50° C. 2.0 g of 10% palladium-carbon catalyst was further added to continue the catalytic hydrogenation for a further 4 hours, whereupon the catalyst was removed by filtration. The crude product obtained was purified by column chromatography (silica gel, 50:1 mixture of chloroform and saturated ammonia in methanol) to obtain 792 mg (yield: 70.7%) of a free base. This free base, converted into hydrochloride, was recrystallized from ethanol to obtain 510 mg of a colorless powder of the title compound.

mp: 226°–229° C.

IR(KBr): 3310, 2947, 1690, 1261, 1206, 1021, 764 cm$^{-1}$.

$^1$H-NMR(CD$_3$OD) δ: 1.40(3H, t, J=6.8 Hz), 2.95–3.70(4H, m), 4.38(2H, q, J=6.8 Hz), 5.20(1H, m), 7.03(1H, d, J=8.3 Hz), 7.12(1H, s), 7.14(1H, d, J=8.3 Hz).

(6) 2,3-Dihydro-7-ethoxycarbonyl-2-trifluoroacetyl-aminomethyl-6H-furo[2,3-e]indole 1.6 g (6.15 mmol) of 2-aminomethyl-2,3-dihydro-7-ethoxycarbonyl-6H-furo[2,3-e]indole, 2.62 g (18.4 mmol) of ethyl trifluoroacetate, and 0.75 g (7.41 mmol) of triethylamine were added to 40 ml of ethanol, and the mixture was stirred for 1.5 hours at 60° C. After the reaction, the solvent was evaporated. The residue was dissolved in ethyl acetate, washed with diluted hydrochloric acid, saturated aqueous solution of sodium hydrogen carbonate, and brine, and dried over anhydrous sodium sulfate. 1.9 g (yield: 86.9%) of a crude product was obtained by evaporating the solvent. This crude product was recrystallized from a mixed solvent of ethyl acetate and n-hexane to obtain a colorless powder of the title compound.

mp: 220°–222° C.

IR(KBr): 3307, 1691, 1526, 1261, 1207, 1101, 763 $cm^{-1}$.

$^1$H-NMR(CDCl$_3$) δ: 1.41(3H, t, J=7.0 Hz), 2.99(1H, dd, J=6.8, 14.7 Hz), 3.40–3.60(2H, m), 3.90(1H, m), 4.40(2H, q, J=7.0 Hz), 5.10(1H, m), 6.80(1H, m), 6.97(1H, d, J=8.3 Hz), 7.13(1H, d, J=8.3 Hz), 7.19(1H, d, J=2.2 Hz), 8.91(1H, br. s).

(7) 5-Acetyl-2,3-dihydro-7-ethoxycarbonyl-2-trifluoroacetylaminomethyl-6 H-furo[2,3-e]indole 500 mg (1.40 mmol) of 2,3-dihydro-7-ethoxycarbonyl-2-trifluoroacetyl-aminomethyl-6H-furo[2,3-e]indole and 1.475 g (7.02 mmol) of trifluoroacetic anhydride were added to 2.5 ml of acetic acid, and the mixture was stirred for one hour at room temperature and overnight at 50° C. After the reaction, the reaction mixture was concentrated. The residue was dissolved in a 10:1 mixture of chloroform and methanol, washed with saturated aqueous solution of sodium hydrogen carbonate and brine, and dried over anhydrous sodium sulfate. 575 mg of a crude product was obtained by evaporating the solvent. This crude product was purified by column chromatography (silica gel, 50:1 mixture of chloroform and ethyl acetate) to obtain 370 mg (yield: 9.0%) of the title compound. Colorless needles were obtained by recrystallization from a mixed solvent of ethyl acetate and n-hexane mp: 219°–221° C.

IR(KBr): 3417, 3278, 1700, 1636, 1576, 1304, 1252, 1204, 749 $cm^{-1}$.

$^1$H-NMR(CDCl$_3$) δ: 1.42(3H, t, J=7.3 Hz), 2.62(3H, s), 3.06(1H, dd, J=6.4, 15.4 Hz), 3.40–3.65(2H, m), 3.95(1H, m), 4.42(2H, q, J=7.3 Hz), 5.20(1H, m), 6.90(1H, m), 7.19(1H, d, J=2.0 Hz), 7.72(1H, s).

(8) 5-Acetyl-2-aminomethyl-2,3-dihydro-7-methoxycarbonyl-6H-furo[2,3 -e]indole•hydrochloride 430 mg (1.08 mmol) of 5-acetyl-2,3-dihydro-7 -ethoxycarbonyl-2-trifluoroacetylaminomethyl-6H-furo[2,3-e]indole was dissolved in 40 ml of saturated ammonia solution in methanol, and the solution was stirred overnight at room temperature. The reaction mixture was concentrated under reduced pressure to dryness to obtain a crude product. This crude product was purified by column chromatography (silica gel, 70:1 mixture of chloroform and saturated ammonia methanol) to obtain 200 mg (yield: 64.3%) of a free base. A pale yellow solid of the title compound were obtained by converting this free base into hydrochloride and by recrystallizing from a mixed solvent of methanol and ether.

mp: >300° C.

IR(KBr): 3419, 2859, 1697, 1640, 1581, 1306, 1259, 1209, 751 $cm^{-1}$.

$^1$H-NMR(CD$_3$OD) δ: 2.63(3H, s), 3.30–3.40(3H, m), 3.65(1H, m), 3.95(3H, s), 5.30(1H, m), 7.22(1H, s), 7.98(1H, s).

(9) 2-Aminomethyl-2,3-dihydro-5-ethyl-7-methoxycarbonyl-6H-furo[2,3 -e]indole•hydrochloride 290 mg (1.0 mmol) of 5-acetyl-2-aminomethyl-2,3-dihydro-7-methoxycarbonyl- 6H-furo[2,3-e]indole was dissolved in a mixed solvent of 15 ml of methanol and 15 ml of 4N hydrochloric acid-dioxane. 2.9 g of zinc powder was added to the solution in portions under cooling below 0° C. The mixture was stirred for one hour under cooling at 0° C. The reaction mixture was concentrated and saturated ammonia methanol was added to the residue to remove zinc powder by filtration. The filtrate was concentrated and the residue was purified by column chromatography (silica gel, 70:1 mixture of chloroform and saturated ammonia methanol) to obtain 22 mg (yield: 7.04%) of a free base. A brown solid of the title compound were obtained by converting this free base into hydrochloride and by recrystallizing the hydrochloride from a mixed solvent of methanol and ether.

mp: >250° C.

IR(KBr): 3410, 2928, 1699, 1527, 1505, 1437, 1257, 1206, 771, 744 $cm^{-1}$.

$^1$H-NMR(CD$_3$OD) δ: 1.28(3H, t, J=7.3 Hz), 2.87(2H, q, J=7.3 Hz), 3.03(1H, dd, J=6.5, 15.0 Hz), 3.10–3.60(3H, m), 3.92(3H, s), 5.15(1H, m), 6.98(1H, s), 7.14(1H, s).

Example 48

(1) 4'-Dimethylaminomethyl-5'-hydroxy-2'-methylacetanilide 14.86 g (90.1 mmol) of 5'-hydroxy-2'-methylacetanilide was dissolved in 50 ml of N,N-dimethylformamide. 32.9 g of 40% (w/w) aqueous solution of dimethylamine and 14.6 g of 37% (w/w) aqueous solution of formalin were added to the solution, and the mixture was stirred for 24 hours at room temperature. After the reaction, the solvent was evaporated under reduced pressure to obtain a crude product. 17.1 mg (yield: 91.2%) of the title compound was obtained by washing this crude product with n-hexane and collecting crystals by filtration.

mp: 152°–156° C. (colorless needles).

IR(KBr): 3253, 2953, 1665, 1645, 1603, 1541, 1394, 1316, 885, 765 $cm^{-1}$.

$^1$H-NMR(CDCl$_3$) δ: 2.013(3H, s), 2.17.(3H, s), 2.30(6H, s), 3.56(2H, s), 6.74(1H, s), 6.90(1H, br. s), 7.24(1H, s).

(2) Ethyl 6-acetylamino-5-methyl-2,3-dihydrobenzo[b]-furan-2-carboxylate 11.11 g (50.0 mmol) of 4-dimethylaminomethyl-5-hydroxy-2-methylacetanilide was dissolved in 100 ml of N,N-dimethylformamide. After the addition of 20.73 g (150 mmol) of potassium carbonate and 34.27 g (150 mmol) of dimethylethoxycarbonylmethylsulfonium bromide, the mixture was stirred for 5 hours at 80° C. After the reaction, the reaction mixture was diluted with water and extracted with ether. The ether layer was washed with water and brine, and dried over anhydrous sodium sulfate. The solvent was evaporated and the residue was purified by column chromatography (silica gel, n-hexane-acetone mixture, 5:1→10:3) to obtain 8.8 g (yield: 67%) of the title compound. Colorless needles were obtained by recrystallization from ether.

mp: 84°–86° C.

IR(KBr): 3232, 3032, 2985, 1758, 1744, 1670, 1644, 1541, 1460, 1373, 1332, 1298, 1211, 1160, 1040, 844 $cm^{-1}$.

$^1$H-NMR(CDCl$_3$) δ: 1.30(3H, t, J=7.3 Hz), 2.17(3H, s), 2.18(3H, s), 3.30(1H, dd, J=6.8, 16.1 Hz), 3.48(1H, dd, J=10.3, 16.1 Hz), 4.25(2H, q, J=7.3 Hz), 5.17(1H, dd, J=6.8, 10.3 Hz), 6.89(1H, br. s), 6.97(1H, s), 7.37(1H, s).

(3) 6-Acetylamino-2-hydroxymethyl-5-methyl-2,3dihydrobenzo[b]-furan 10 g (38.0 mmol) of ethyl 6-acetylamino-5-methyl-2,3-dihydrobenzo[b]-furan-2-carboxylate was dissolved in 100 ml of methanol. After the addition of 3.21 g (8.50 mmol) of sodium borohydride, the solution was stirred for one hour at 0° C. After the reaction, the reaction mixture was concentrated under reduced pressure. The residue was diluted with ethyl acetate, extracted, washed, and dried. The solvent was evaporated to obtain 4.8 g (yield: 77.5%) of the title compound.

mp: 125°–127° C. (colorless needles).

IR(CHCl$_3$): 3405, 2948, 1676, 1488, 1440, 1366, 1233, 1161, 1079, 991 cm$^{-1}$.

$^1$H-NMR(CD$_3$OD) δ: 2.07(3H, s), 2.08(3H, s), 2.88(1H, dd, J=7.3, 15.6 Hz), 3.13(1H, dd, J9.3, 15.6 Hz), 3.63(2H, m), 4.76(1H, m), 6.68(1H, s), 6.95(1H, s).

(4) 6-Amino-2-hydroxymethyl-5-methyl-2,3-dihydrobenzo[b]-furan•hydrochloride 6.63 g (30 mmol) of 6-acetylamino-2-hydroxymethyl-5-methyl-2,3-dihydrobenzo[b]-furan was dissolved in 60 ml of ethanol. After the addition of 15 ml of aqueous hydrochloric acid, the solution was stirred for 10 hours at 100° C. After the reaction, the solvent was evaporated under reduced pressure to obtain a light yellow solid. This solid was recrystallized from an ethanol-ether mixture to obtain 4.57 g (yield: 70.6%) of the title compound.

IR(KBr): 3303, 2851, 1491, 1223, 1051, 941, 846, 751 cm$^{-1}$.

$^1$H-NMR(CD$_3$OD) δ: 2.28(3H, s), 3.03(1H, dd, J=6.8, 16.1 Hz), 3.25(1H, dd, J=8.8, 16.1 Hz), 3.66(1H, dd, J=5.4, 11.7 Hz), 3.75(1H, dd, J=3.4, 11.7 Hz), 4.88(1H, m), 6.73(1H, s), 7.16(1H, s).

(5) 5-Methyl-6-methoxalylamino-2-methoxalyloxymethyl-2,3-dihydrobenzo[b-]furan 7.33 g (3.4 mmol) of 6-Amino-2-hydroxymethyl-5-methyl-2,3-dihydrobenzo[b]furan•hydrochloride was suspended in 120 ml of methylene chloride. 3.54 g (3.50 mmol) of triethylamine and 7.91 g (100 mmol) of pyridine were added to the suspension. Then, 10.41 g (9.42 mmol) of methyloxalyl chloride was added dropwise while cooling the mixture at 0° C. After the addition, the mixture was stirred for 2 hours at room temperature (25° C.). After the reaction, water was added. The methylene chloride layer was washed with water, 5% aqueous solution of potassium hydrogen sulfate, aqueous solution of sodium hydrogen carbonate, and brine, and dried over anhydrous sodium sulfate. The mixture was concentrated under reduced pressure to obtain a crude product. This crude product was recrystallized from an acetone-n-hexane mixture to obtain 11.4 g (yield: 95%) of the title compound.

mp: 120°–123° C. (colorless needles).

IR(KBr): 3425, 3391, 2962, 1771, 1742, 1731, 1709, 1604, 1533, 1437, 1330, 1293, 1210, 1164, 962, 852, 620 cm$^{-1}$.

$^1$H-NMR(CDCl$_3$) δ: 2.24(3H, s), 2.96(1H, dd, J=7.3, 16.1 Hz), 3.31(1H, dd, J=9.3, 16.1 Hz), 3.90(3H,s), 3.97(3H, s), 4.45(2H, d, J=15.4 Hz), 5.09(1H, m), 7.01(1H, s), 7.57(1H, s), 8.76(1H, br. s).

(6) 6-(N-benzyl-N-methoxalyl)amino-2-hydroxymethyl-5-methyl-2,3-dihydrobenzo[ b]-furan 5.48 g (15.6 mmol) of 5-methyl-6-methoxalylamino-2-methoxalyloxymethyl-2,3-dihydrobenzo[b]-furan was dissolved in 30 ml of dimethylsulfoxide. 1.5 g (31.25 mmol) of sodium hydride (50% purity in mineral oil) was added to the solution at 0° C., followed by stirring for 10 minutes. After the addition of 3.83 g (22.4 mmol) of benzyl bromide and stirring for 10 minutes at the same temperature, the mixture was stirred for a further 60 minutes at room temperature. 2 ml of methanol was added at 0° C. and the mixture was stirred at room temperature. After the reaction, the reaction mixture was diluted with 60 ml of saturate ammonia water and 60 ml of cold water, and extracted with ether. The ether layer was washed with water and brine, and dried over anhydrous sodium sulfate. The solvent was evaporated under reduced pressure and the residue was purified by column chromatography (silica gel, n-hexane-acetone mixture, 3:2→ 1:1) to obtain 4.23 g (yield: 83.8%) of the title compound as an oil.

IR(Cap.): 3604, 3465, 3019, 2956, 1745, 1663, 1490, 1216, 758, 669 cm$^{-1}$.

$^1$H-NMR(CDCl$_3$) δ: 2.30(3H, s), 3.25(1H, m), 3.45(1H, dd, J=9.3, 16.1 Hz), 3.82(s) 3.83(s) (3H, altogether), 3.97(1H, m), 4.08(1H, m), 4.62(d, J=13.7 Hz) 4.65(d, J=13.7 Hz) (1H, altogether), 5.16(1H, m), 5.48(d, J=13.7 Hz), 5.50(d, J=13.7 Hz) (1H, altogether), 6.52(s) 6.54(s)(1H, altogether), 7.42–7.60(6H, m).

(7) 6-(N-benzyl-N-methoxalyl)amino-2-methanesulfonyloxy-5-methyl-2,3 -dihydrobenzo[b]-furan 14.2 g (40 mmol) of 6-(N-benzyl-N-methoxalyl)amino-2-hydroxymethyl-5-methyl-2,3 -dihydrobenzo[b]-furan was dissolved in 150 ml of pyridine. 6.87 g (60 mmol) of methanesulfonyl chloride was added dropwise to the solution at 0° C., followed by stirring for 14 hours at 0° C. After the reaction, the reaction mixture was diluted with ether. The ether layer was washed with water, 10% aqueous solution of potassium hydrogen sulfate, and brine, and dried over anhydrous sodium sulfate. The solvent was evaporated under reduced pressure. The residue was purified by column chromatography (silica gel, n-hexane-acetone mixture, 5:2→ 5:3) and recrystallized from a mixture of ethyl acetate, ether, and n-hexane to obtain 16.98 g (yield: 92.5%) of the title compound.

mp: 115°–117° C. (colorless crystals).

IR(KBr): 2963, 2926, 1748, 1669, 1492, 1330, 1261, 1224, 1170, 1021,964, 820, 801, 700 cm$^{-1}$.

$^1$H-NMR(CDCl$_3$) δ: 2.05(s) 2.07(s) (3H, altogether), 2.92(s) 2.99(s) (3H, altogether), 3.00(1H, m), 3.27(dd, J=3.4, 9.5 Hz) 3.33(dd, J=3.4, 9.5 Hz) (1H, altogether), 3.55(s) 3.56(s)(3H, altogether), 4.30(d, J=13.9 Hz) 4.31(d, J=13.9 Hz)(1H, altogether), 4.32(1H, m), 4.40(1H, dd, J=3.4, 11.5 Hz), 5.00(1H, m), 5.02(d, J=13.9 Hz) 5.03(d, J=13.9 Hz)(1H, altogether), 6.23(s)6.25(s), (1H, altogether), 7.01(1H, s) 7.18–7.35(5H, m).

(8) 6-Benzyl-2-methanesulfonyloxy-5-methyl-2,3-7,8-tetrahydro-6H-furo[2,3-e] indol-7,8-dione 10 g (23.1 mmol) of 6-(N-benzyl-N-methoxalyl)amino-2-methanesulfonyloxy-5-methyl-2,3-dihydrobenzo[b] -furan was dissolved in 100 ml of ethanol. 10 ml of aqueous solution of potassium hydroxide (85%, 1.78 g (27.0 mmol)) was added and the mixture was stirred for 2 hours at room temperature. After the reaction, the solvent was removed by distillation under reduced pressure (water was evaporated while azeotropically distilling with the addition of toluene) to obtain 11 g of potassium carboxylate. The potassium carboxylate was suspended in 70 ml of benzene, and 8.88 g (70.0 mmol, of oxalyl chloride was added to it, followed by stirring for one hour at room temperature. After the reaction, the solvent was evaporated under reduced pressure to obtain carboxylic acid chloride, which was used without further purification for the next reaction.

8.8 g (65.9 mmol) of aluminum chloride powder was suspended in 80 ml of 1,2-dichloroethane, and to this suspension was added dropwise a solution of said carboxylic acid chloride in 1,2-dichloroethane. The mixture was stirred at room temperature for 1.5 hours. After the reaction, the reaction mixture was poured into 200 ml of ice water. 2N hydrochloric acid and chloroform was added to dissolve insoluble components, followed by extraction with chloroform. The chloroform layer was washed with brine and dried over anhydrous magnesium sulfate. The solvent was evaporated under reduced pressure to obtain 9 g of a crude product, which was recrystallized from a mixture of methylene chloride and ether to obtain 2.74 g (yield: 31%) of the title compound as a dark red powder.

mp: 211°–214° C.

IR(KBr): 3420, 2961, 2935, 1719, 1621, 1484, 1340, 1329, 1249, 1175, 1061, 933,910, 826, 798, 726 cm$^{-1}$.

$^1$H-NMR(CDCl$_3$) δ: 2.16(3H, s), 3.01(1H, ddd, J=1.2, 7.8, 16.1 Hz), 3.13(3H, s), 3.27(1H, ddd, J=1.2, 9.8, 16.1 Hz), 4.47(1H, d, J=1.2 Hz), 4.48(1H, d, J=0.8 Hz), 5.18(2H, s), 5.29(1H, m), 7.02(1H, s), 7.15–7.40(5H, m).

(9) 2-Methanesulfonyloxymethyl-5-methyl-2,3,7,8-tetrahydro-6H-furo[2,3-e] indol-7,8-dione (1) and 8-hydroxy-2-methanesulfonyloxymethyl-5 -methyl-2,3,7,8-tetrahydro-6H-furo[2,3-e]indol-7-one (2)

0.45 g (1.12 mmol) of 6-benzyl-2-methanesulfonyloxymethyl-5-methyl-2,3,7,8-tetrahydro-6 H-furo[2,3-e]indol-7,8-dione was dissolved in 20 ml of acetic acid. 0.9 g of 10% palladium-carbon catalyst was added to the solution. After the addition of 0.2 ml of concentrated hydrochloric acid, the mixture was catalytically hydrogenated at 80° C. and normal pressure under a hydrogen atmosphere. After one hour, the catalyst was removed by filtration and the solvent was evaporated to obtain a crude product. This crude product was purified and separated by column chromatography (silica gel, n-hexane:acetone mixture=5:3→ chloroform:methanol=9:1) to obtain 80 mg (yield: 23%) of the title compound (1) and 74 mg (yield: 21%) of the title compound (2).

Title compound (1)

Light orange crystals mp: 223°–225° C. (Decomposed).

IR(KBr): 3689, 3442, 2930, 2864, 2360, 2342, 1732, 1652, 1483, 1362, 1224, 1175, 1091, 821, 721 cm$^{-1}$.

$^1$H-NMR(CDCl$_3$) δ: 2.19(3H, s), 2.95–3.01(1H, m), 3.05(3H, s), 3.20–3.36(1H), 4.30–4.50(2H, m), 5.10(1H, m), 6.92(1H, s), 8.23(1H, br. s).

Title compound (2).

Light orange crystals mp: 204°–206° C. (Decomposed).

IR(KBr): 3471, 3438, 3181, 3033, 2938, 2864, 2546, 2360, 2342, 1713, 1644, 1478, 1342, 1181, 1000, 974, 940, 839 cm$^{-1}$.

$^1$H-NMR(CDCl$_3$–CD$_3$OD) δ: 2.16(3H, s), 3.00(1H, m), 3.11(s) 3.12(s)(3H, altogether), 3.28(1H, m), 5.01(1H, d, J=1.7 Hz), 5.12(1H, m), 6.90(1H, s).

(10) 2-Methanesulfonyloxymethyl-5-methyl-2,3,7,8-tetrahydro-6H-furo[2,3 -e]indol-7-one 0.18 g (yield, 7.4%) of the title compound was obtained by reacting 3.3 g (8.2 mmol) of 6-benzyl-2-methanesulfonyloxymethyl-5-methyl-2,3,7,8 -tetrahydro-6H-furo[2,3-e]indol-7,8-dione under the same conditions as (9) and heating for two hours under refluxing. Pale brown crystals (mp: 233°– 236° C.) was obtained by recrystallization from a mixed solvent of methylene chloride-methanol-ether.

IR(KBr): 3189, 3072, 2928, 2866, 1679, 1643, 1483, 1462, 1348, 1310, 1251, 1178, 1098, 985, 954, 850, 824 cm$^{-1}$.

$^1$H-NMR(CDCl$_3$–CD$_3$OD) δ: 2.18(3H, s), 3.00(1H, dd, J=7.3, 15.6 Hz), 3.09(3H, s), 3.30(1H, dd, J=9.5, 15.6 Hz), 3.44(2H, s), 4.38(2H, m), 5.08(1H. m), 6.86(1H, s).

(11) 6-Benzyl-2-methanesulfonyloxymethyl-5-methyl-2,3, 7,8-tetrahydro-6H-furo[ 2,3-e]indol-7-one 802 mg (2.00 mmol) of 6-benzyl-2-methanesulfonyloxymethyl- 5-methyl-2,3,7,8-tetrahydro-6H-furo[2,3-e]indol-7,8-dione was dissolved in 40 ml of chloroform. After the addition of 1.2 g (6.00 mmol) of iodo trimethylsilane, the solution was stirred for 2 hours at room temperature. After the reaction, the reaction mixture was poured into ice water to separate the chloroform layer. The chloroform layer was washed with an aqueous solution of 10% sodium sulfate and saturated brine, and dried over anhydrous magnesium sulfate. The solvent was evaporated under reduced pressure and the residue was purified by column chromatography (silica gel, 5:3 mixture of n-hexane and acetone) to obtain 354 mg (yield: 45.7%) of the title compound as a reddish brown solid.

mp: 152°–155° C.

IR(KBr): 3449, 2933, 1614, 1359, 1337, 1180, 994, 969, 815, 707 cm$^{-1}$.

$^1$H-NMR(CDCl$_3$) δ: 2.19(3H, s), 2.98(1H, dd, J=6.8, 15.6 Hz), 3.08(3H, s), 3.29(1H, dd, J=9.5, 15.6 Hz), 3.55(2H, s), 4.38(1H, d, J=1.9 Hz), 4.40(1H, m), 5.09(1H, m), 5.18(2H, s), 6.76(1H, s), 7.12–7.35(5H, m).

(12) 6-Benzyl-2-aminomethyl-5-methyl-2,3,7,8-tetrahydro-6H-furo[2,3-e] indol-7-one•hydrochloride 155 mg (0.401 mmol) of 6-benzyl-2-methanesulfonyloxymethyl-5-methyl-2,3,7,8 -tetrahydro-6H-furo[2,3-e]indol-1-one was dissolved in 2 ml of N,N-dimethylformamide. After the addition of 130 mg (2.00 mmol) of sodium azide, the solution was stirred for 30 minutes at 110° C. After the reaction, the reaction mixture was diluted with water and extracted with ethyl acetate. The organic layer was washed with water, saturated brine, and dried over anhydrous magnesium sulfate. The solvent was evaporated under reduced pressure and the residue obtained was submitted to the next reaction without purification. Of the crude azide compound (133 mg, quantitative), 130 mg (0.389 mmol) was dissolved in 2 ml of acetic acid, and 67 μl of concentrated hydrochloric acid was added to it. After the addition of 70 mg of 10% palladium-carbon catalyst, the mixture was catalytically hydrogenated at 80° C. under a hydrogen atmosphere. After the reaction, the catalyst was removed by filtration and the solvent was evaporated to obtain a light brown solid. This solid was recrystallized from a mixed solvent of methanol and ether to obtain 72 mg (yield: 83%) of the title compound as pale brown crystals.

mp: 246°–249° C.

IR(KBr): 3421, 2926, 2894, 1674, 1644, 1615, 1481, 1353, 1253, 1132, 965, 714 cm$^{-1}$.

$^1$H-NMR(CD$_3$OD) δ: 2.18(3H, s), 2.92(1H, dd, J=5.6, 16.3 Hz), 3.14(1H, dd, J=9.3, 13.4 Hz), 3.30(1H, m), 3.38(1H, dd, J=9.3, 16.3 Hz), 3.61(2H, s), 5.04(1H, m), 5.21(2H, s), 6.84(1H, s), 7.19–7.37(5H, m).

(13) 2-Methanesulfonyloxymethyl-5-methyl-2,3,7,8-tetrahydro-6H-furo[2,3 -e]indol-7-one 193 mg (0.499 mmol) of 6-benzyl-2-methanesulfonyloxymethyl- 5-methyl-2,3,7,8-tetrahydro-6H-furo[2,3-e]indol-7-one was dissolved in 3 ml of acetic acid. After the addition of 100 mg of 10% palladium-carbon catalyst, 50 μl of concentrated hydrochloric acid was added, and the mixture was catalytically hydrogenated at 80° C. under a hydrogen atmosphere. After one hour, the catalyst was removed by filtration and the solvent was evaporated to obtain 142 mg (yield: 95%) of a colorless solid of the title compound.

mp: 233°–236° C.

(14) 2-Azidomethyl-5-methyl-2,3,7,8-tetrahydro-6H-furo [2,3-e]indol-7-one 140 mg (0.471 mmol) of 2-methanesulfonyloxymethyl-5 -methyl-2,3,7,8-tetrahydro-6H-furo[2,3-e]indol-7-one was dissolved in 2 ml of N,N-dimethylformamide. After the addition of 65 mg (1.00 mmol) of sodium azide, the solution was stirred for 30 minutes at 110° C. After the reaction, the reaction mixture was diluted with water and extracted with ethyl acetate. The organic layer was washed with water, saturated brine, and dried over anhydrous magnesium sulfate. The solvent was evaporated under reduced pressure and the residue obtained was purified by column chromatography (silica gel, 5:2 mixture of n-hexane and acetone) to obtain 92 mg (yield: 80%) of the title compound as a brown solid.

IR(KBr): 3174, 3069, 2942, 2926, 2868, 2122, 1726, 1698, 1644, 1481, 1305, 1253, 1097, 975, 794, 723 cm$^{-1}$.

$^1$H-NMR(CDCl$_3$) δ: 2.20(3H, s), 2.96(1H, dd, J=6.4, 15.6 Hz), 3.27(1H, dd, J=8.8, 15.6 Hz), 3.42(1H, dd,J=5.9, 12.9 Hz), 3.49(2H, s), 3.54(1H, dd, J=3.9, 12.9 Hz), 5.01(1H, m), 6.85(1H, s), 8.73(1H, br. s).

(15) 2-Aminomethyl-5-methyl-2,3,7,8-tetrahydro-6H-furo [2,3-e]indol-7-one•hydrochloride 90 mg (0.369 mmol) of 2-azidomethyl-5-methyl-2,3,7,8-tetrahydro-6H-furo[2,3-e]indol-7 -one was dissolved in 4 ml of tetrahydrofuran and 2 ml of ethanol. After the addition of 40 mg of 10% palladium-carbon catalyst, the mixture was catalytically hydrogenated at normal temperature and pressure under a hydrogen atmosphere. After 3 hours, the catalyst was removed by filtration and the solvent was evaporated. The residue obtained was partitioned by an aqueous solution of potassium carbonate and chloroform. After the extraction with chloroform, the organic layer was washed with saturated brine and dried over anhydrous magnesium sulfate. The solvent was evaporated and the residue obtained was purified by column chromatography (silica gel, 95:5 mixture of chloroform and methanol) to obtain 56 mg (yield: 70%) of a free base. The free base was made into hydrochloride and recrystallized from a methanol-ether mixed solvent to obtain 38 mg (yield: 58.1%) of the title compound as brown crystals.

mp: >300° C.

IR(KBr): 3432, 3170, 3019, 2936, 1698, 1645, 1480, 1440, 1305, 1251, 1095, 968, 717 cm$^{-1}$.

$^1$H-NMR(CD$_3$OD) δ: 2.16(3H, s), 2.91(1H, dd, J=5.9, 15.6 Hz), 3.12(1H, dd, J=9.3, 13.4 Hz), 3.26(1H, dd, J=3.2, 13.4 Hz), 3.38(1H, dd, J=6.6, 15.6 Hz), 3.43(2H, s), 5.03(1H, m), 6.89(1H, s),

(16) 2-Azidomethyl-8-hydroxy-2,3,7,8-tetrahydro-6H-furo[ 2,3-e]indol-7-one

This compound was prepared in the same manner as in (14) above.

IR(KBr): 3424, 3189, 3058, 2926, 2102, 1732, 1641, 1477, 1278, 1227, 992, 808, 731 cm$^{-1}$.

$^1$H-NMR (CDCl$_3$) δ: 2.17(3H,s), 3.02(1H, dd, J=6.4, 15.6 Hz), 3.22(1H, dd, J=9.0, 15.6 Hz), 3.51(1H, dd, J=4.2, 13.2 Hz), 3.76(1H,dd, J=4.2, 13.2 Hz), 5.15(1H, m), 7.12(1H, s), 8.93(1H, br. s).

(17) 2-Aminomethyl-8-hydroxy-2,3,7,8-tetrahydro-6H-furo [2,3-e]indol-7-one•hydrochloride 40 mg (0.154 mmol) of 2-azidomethyl-8-hydroxy-2,3,7, 8-tetrahydro-6H-furo[2,3 -e]indol-7-one was dissolved in 4 ml of tetrahydrofuran and 1 ml of methanol. After the addition of 15 mg of 10% palladium-carbon catalyst, the mixture was catalytically hydrogenated at normal temperature and pressure under a hydrogen atmosphere. After 4 hours, the catalyst was removed by filtration and the solvent was evaporated. The free base obtained was made into hydrochloride, and recrystallized from a methanol-ether mixed solvent to obtain 18 mg (yield: 50.0%) of the title compound as brown crystals.

mp: >300° C.

IR(KBr): 3412, 3201, 2925, 2855, 2105, 1724, 1640, 1479, 1231, 1099, 961,734,699 cm$^{-1}$.

$^1$H-NMR(CD$_3$OD) δ: 2.12(3H, s), 2.87–3.05(1H, m), 3.15–3.36(1H, m), 3.40–3.79(2H, m), 4.90(1H, m), 5.19(1H, m), 7.19(1H, br.s).

Example 49

(1) 2-Benzylamino-4-benzyloxy-1-methylbenzene 100.0 g (2.56 mol) of sodium amide was added to 700 g (6.53 mol) of benzylamine under an argon atmosphere, and the mixture was stirred for 10 minutes at 60° C. A solution of 222.20 g (0.801 mol) of 1-benzyloxy-2-bromo-4-methylbenzene was dissolved in 400 ml of tetrahydrofuran was added dropwise to the above mixture over 50 minutes. The mixture was stirred for 50 minutes while maintaining the temperature at 60° C. Methanol was added under cooling with ice, and the mixture was poured into ice water. The reaction mixture was extracted with ethyl acetate-water, and the organic layer was washed with saturated brine and dried over anhydrous sodium sulfate. The residue obtained by evaporating the solvent was purified by column chromatography (silica gel, 10:1 mixture of n-hexane and ethyl acetate). The crude product thus obtained was recrystallized from n-hexane to obtain 175.80 g (yield: 72.3%) of the title compound as colorless needles.

mp: 66°–67° C.

IR(KBr): 3435, 3061, 3030, 2958, 2930, 2897, 1617, 1584, 1518, 1496, 1451, 1377, 1354, 1331, 1292, 1252, 1213, 1191, 1181, 1138, 1040, 1029, 992, 918, 831, 781, 734, 723, 694, 457 cm$^{-1}$.

$^1$H-NMR(CDCl$_3$) δ: 2.09(3H, s), 3.87(1H, br.), 4.32(3H, s), 4.98(3H, s), 6.27–6.30(2H, m), 6.95(1H, d, J=9.0 Hz), 7.24–7.42(10H, m).

(2) N-Benzyl-5'-benzyloxy-2'-methyl-methyloxalanilide 101.00 g (0.333 mol ) of 2-benzylamino-4-benzyloxy-1-methylbenzene was dissolve in 400 ml of chloroform, and 40 g (0.424 mol) of pyridine was added to the solution. After the addition of 52.0 g (0.424 mol) of methyloxalyl chloride under cooling with ice while stirring, the mixture was stirred for 25 minutes. Methanol was added to the reaction mixture to decompose excessive methyloxalyl chloride, and the mixture was extracted with chloroform-1N hydrochloric acid. The organic layer was dried over anhydrous sodium sulfate. The residue obtained by evaporating the solvent was purified by column chromatography (silica gel, 15:1 mixture of n-hexane and ethyl acetate) to obtain 123.68 mg (yield: 97.6%) of the title compound as a colorless oil.

IR(Cap.): 3464, 3065, 3033, 2954, 2929, 2870, 1747, 1671, 1613, 1581, 1502, 1455, 1404, 1384, 1213, 1176, 1080, 1027, 739, 699, 517 cm$^{-1}$.

$^1$H-NMR(CDCl$_3$) δ: 2.07(3H, s), 3.47(3H, s), 4.33(1H, d, J=13.9 Hz), 4.79(1H, d, J=12.0 Hz), 4.85(1H,d, J=12.0 Hz), 5.28(1H, d, J=13.9 Hz), 6.38(1H, d, J=2.7 Hz), 6.86(1H, dd, J=2.7, 8.6 Hz), 7.10(1H, d, J=8.6 Hz), 7.17–7.42(10H, m).

(3) 4-Allyloxy-1-benzyl-2,3-dihydro-7-methyl-1H-indol-2, 3-dione 149.98 g (0.386 mol) of N-benzyl-5'-benzyloxy-2'-methylmethyloxalanilide was dissolve in 900 ml of 90% ethanol aqueous solution. After the addition of 44.0 g (0.786 mol) of potassium hydroxide, the mixture was stirred for 2 hours at 50° C. The reaction mixture was concentrated under reduced pressure, and to the residue were slowly added 400 ml of trifluoroacetic acid and then 400 ml of trifluoroacetic anhydride under cooling with ice. The temperature was raised to 50° C and the mixture was stirred for 1 hour, and for a further 35 hours at 60° C. The reaction mixture was concentrated under reduced pressure and the residue was extracted with chloroform. The organic layer was partitioned by 1N aqueous solution of sodium hydroxide. Hydrochloric acid was added to the basic water layer to adjust pH to about 4, and this layer was extracted with chloroform. The organic layer was dried over anhydrous sodium sulfate. The residue obtained by evaporating the solvent under reduced pressure was dissolved in 200 ml of N,N-dimethylformamide, and 100 g (0.725 mol) of potassium carbonate and 50.0 g (0.298 mol) of allyl iodide were added to the solution, followed by stirring for 90 minutes at 60° C. The reaction mixture was concentrated under reduced pressure and the residue was extracted with chloroform. The organic layer was dried over anhydrous sodium sulfate. The residue obtained by evaporating the solvent under reduced pressure was recrystallized from benzene to obtain reddish brown crude crystals. The crystals were recrystallized from ethyl acetate-ether-n-hexane to obtain 17.3 g (three steps, 14.2%) of a reddish brown powder of the title compound.

mp: 202°–203° C. IR(KBr): 3450, 2962, 2923, 2852, 1735, 1725, 1615, 1595, 1504, 1463, 1442, 1411, 1296, 1288, 1276, 1263, 1225, 1133, 1082, 1056, 1022, 1009, 997, 970, 822, 806, 729 cm$^{-1}$.

$^1$H-NMR(CDCl$_3$) δ: 2.17(3H, s), 4.73(2H, ddd, J=1.5, 1.7, 4.9 Hz), 5.35(1H, ddd, J=1.5, 2.9, 10.5 Hz), 5.51(1H, ddd, J=1.7, 2.9, 17.3 Hz), 6.04(1H, ddt, J=4.9, 10.5, 17.3 Hz), 6.52(1H, d, J=8.5 Hz), 7.14(1H,d, J=8.5 Hz), 7.16–7.65(5H,m).

(4) 6-Benzyl-2-iodomethyl-5-methyl-2,3,7,8-tetrahydro-6H-furo[2,3-e]indol-7,8-dione 13.4 g (42.4 mmol) of 4-allyloxy-1-benzyl-2,3-dihydro-7-methyl-1H-indol-2,3-dione was melted at 222° C. and heated for 50 minutes while stirring. The reaction residue was allowed to cool to the room temperature, whereupon it was dissolve in 360 ml of a 4:1 mixed solvent of chloroform and methanol. After successively adding 10.0 g (72.4 mmol) of potassium carbonate, 10.0 g (60.2 mmol) of potassium iodide, and 12.0 g (47.2 mmol) of iodine, the mixture was stirred for 3 hours at room temperature. Sodium sulfite was added to the reaction mixture to decompose excessive iodine. After extraction with chloroform, the organic layer was washed with brine, dried over anhydrous sodium sulfate, and concentrated under reduced pressure. The residue obtained was recrystallized from a mixed solvent of chloroform-benzene-n-hexane to obtain 11.8 g (two steps, 63.0%) of a reddish brown powder of the title compound.

mp: 203°–205° C.

IR(KBr): 3420, 1720, 1623, 1593, 1497, 1483, 1454, 1440, 1411, 1393, 1347, 1253, 1236, 1214, 1202, 1138, 1089, 987, 950, 729, 699 cm$^{-1}$.

$^1$H-NMR(CDCl$_3$) δ: 2.15(3H, s), 2.97(1H, ddd, J=1.2, 6.4, 16.1 Hz), 3.31(1H, ddd, J=1.2, 9.0, 16.1 Hz), 3.40(1H, dd, J=8.1, 10.3 Hz), 3.57(1H, dd, J=3.7, 10.3 Hz), 5.09(1H, dddd, J=3.7, 6.3, 8.1, 9.0 Hz), 5.18(2H,s), 6.99(1H, d, J=0.8 Hz), 7.17–7.37(5H, m).

(5) 6-Benzyl-2-dimethylaminomethyl-5-methyl-2,3,7,8-tetrahydro-6H-furo[2,3-e]indol-7,8-dione 11.7 g (26.5 mmol) of 6-benzyl-2-iodomethyl-5-methyl-2,3,7,8-tetrahydro-6H-furo[e]indol-7,8-dione was dissolved in 140 ml of N,N-dimethylformamide. 70 ml of 10% aqueous solution of dimethyl amine was added and the mixture was heated under refluxing for 30 minutes at 150° C. The residue obtained by concentrating the reaction mixture under reduced pressure was purified by column chromatography (silica gel, n-hexane-chloroform=1:4→chloroform-ammonia methanol=10:1) to obtain 7.0 g (yield: 73.7%) of a dark brown foam of the title compounds.

IR(Cap.): 3427, 2972, 1722, 1632, 1482, 1455, 1411, 1393, 1360, 1336, 1286, 1264, 1235, 1208, 1137, 1089, 1032, 1014, 998, 912, 899, 840, 777, 731, 696 cm$^{-1}$.

$^1$H-NMR(CDCl$_3$) δ: 1.21(3H, t, J=7.6 Hz), 2.13(3H, s), 2.34(6H, s), 2.61(1H, dd, J=6.3, 12.9 Hz), 2.75(1H, dd, J=5.8, 12.9 Hz), 2.93(1H, dd, J=6.4, 16.1 Hz), 3.19(1H, dd, J=8.0, 16.1 Hz), 5.11(1H, m), 5.16(2H, s), 6.97(1H, s), 7.15–7.37(5H, m).

(6) 6-Benzyl-2-dimethylaminomethyl-5-methyl-2,3,7,8-tetrohydro-6H-furo[2,3-e] indol-7-one 2.00 g (5.95 mmol) of 6-benzyl-2-dimethylamino-methyl-5-methyl-2,3,7,8 -tetrahydro-6H-furo[2,3-e]indol-7,8-dione was dissolved in 70 ml of acetic acid. After the addition of 4.00 g of 10% palladium-carbon catalyst and 6 ml of 2N hydrochloric acid solution in acetic acid, the mixture was stirred for 3 hours at 80° C. under a hydrogen atmosphere. The reaction mixture was filtered, the filtrate was concentrated under reduced pressure and purified by separation thin layer chromatography (silica gel, 10:1 mixture of chloroform and ammonia methanol) to obtain 276.8 mg (yield: 14.4%) of the title compound as a yellowish brown foam.

IR(Cap.): 3410, 3011, 2927, 2855, 1709, 1648, 1616, 1497, 1483, 1470, 1455, 1442, 1414, 1394, 1360, 1339, 1312, 1251, 1218, 1190, 1131, 1081, 1036, 997, 965, 926, 755, 711, 666 cm$^{-1}$.

$^1$H-NMR(CD$_3$OD) δ: 2.18(3H, s), 2.44(6H, s), 2.63(1H, dd, J=4.2, 13.2 Hz), 2.80(1H, dd, J=8.1, 13.2 Hz), 2.85(1H, dd, J=7.1, 15.6 Hz), 3.25(1H, dd, J=9.0, 15.6 Hz), 3.57(2H, s), 5.01(1H, m), 5.18(2H, s), 6.73(1H, s), 7.10–7.33(5H, m).

(7) 8,8-Bis(cyanomethyl)-6-benzyl-2-dimethylaminomethyl-5-methyl-2,3,7,8-tetrahydro- 6H-furo[2,3-e]indol-7-one 258.0 mg (0.801 mmol) of 6-benzyl-2-dimethylaminomethyl- 5-methyl-2,3,7,8-tetrahydro-6H-furo[2,3-e]indol-7-one was dissolved in 5 ml of ethanol. 250 mg (2.23 mmol) of potassium butoxide and 0.3 mg (3.97 mmol) of chloroacetonitrile were successively added to the solution, followed by stirring for 30 minutes at room temperature. The reaction mixture was extracted from chloroform-water. The organic layer was washed with saturated brine, dried over anhydrous sodium sulfate, and concentrated under reduced pressure. The residue obtained was purified by separation thin layer chromatography (silica gel, 20:1 mixture of chloroform and ammonia methanol) to obtain 9.3 mg (yield, 2.9%) of a dark brown solid of the title compound.

IR (Cap.): 3852, 3440, 2923, 2853, 2359, 1683, 1633, 1496, 1468, 1455, 1408, 1385, 1332, 1305, 1253, 1206, 1133, 1093, 1038, 1014, 1001, 949, 908, 887, 789, 724, 694 cm$^{-1}$.

$^1$H-NMR(CD$_3$OD) δ: 2.15(3H, s), 2.16–2.44(4H, m), 2.45(6H, s), 2.76(1H, dd, J=5.6, 13.2 Hz), 2.84(1H, dd, J=7.4, 13.2 Hz), 2.89(1H, dd, J=6.6, 15.6 Hz), 3.21(1H, dd, J=8.8, 15.6 Hz), 5.17(1H, m), 5.21(2H, s), 6.70(1H, s), 7.15–7.33(5H, m).

Example 50

Optical resolution of 2-aminomethyl-2,5,8,8-tetramethyl-2, 3,7,8-tetrahydro-6H-furo[ 2,3-e]indol-7-one• hydrochloride Optical resolution was carried out on a methanol solution of 580 mg of (±)-2-aminomethyl-2,5,8,8-tetramethyl-2,3,7, 8-tetrahydro-6H-furo[2,3-e] indol-7-one•hydrochloride using HPLC (CHIRALPAK-AD, n-hexane: 2-propanol:diethylamine=19:1:0.02).

The solvent was evaporated under reduced pressure from the first eluant to obtain 260 mg of an optically active free base. This base was made into hydrochloride and recrystallized from a mixed solvent of methanol and ether, to obtain 106 mg of optically active 2-aminomethyl-2,5,8,8-tetramethyl-2,3,7,8-tetrahydro-6H-furo[2,3-e]indol-7-one•hydrochloride as a pale yellow powder.

mp: >300° C.

Optical purity: 70.8% ee (calculated from HPLC area ratios)

IR(KBr): 2907, 1699, 1642, 1475, 1380, 1269, 1089, 1043, 771 cm$^{-1}$.

$^1$H-NMR(CDCl$_3$–CD$_3$OD) δ: 1.37(3H, s), 1.40(3H, s), 1.51(3H, 2.17(3H, s), 2.99(1H, d, J=15.6 Hz), 3.14(1H, d, J=15.6 Hz), 3.21–3.40(2H, m, overlapped with solvent), 6.85(1H, s).

The solvent was evaporated under reduced pressure from the second eluant to obtain 140 mg of an optically active free base. This base was treated in the same manner to obtain 140 mg of another optically active hydrochloride as pale yellow powder.

mp: >300° C.

Optical purity: 97.7% ee (calculated from HPLC area ratios)

IR(KBr): 2857, 1681, 1643, 1475, 1268, 1088, 1043, 770 cm$^{-1}$.

$^1$H-NMR(CDCl$_3$–CD$_3$OD) δ: 1.37(3H, s), 1.40(3H, s), 1.51(3H, s), 2.17(3H, s), 2.99(1H, d, J=15.6 Hz), 3.14(1H, d, J=15.6 Hz), 3.21–3.40 (2H, m, overlapped with solvent), 6.85(1H, s).

Example 51

Optical resolution of (2R*,3R*)-2-aminomethyl-3,5,8,8-tetramethyl-2,3,7,8 -tetrahydro-6H-furo[2,3-e]-indol-7-one•hydrochloride Optical resolution was carried out on a methanol solution of 685 mg of (±)-(2R*,3R*)-2-aminomethyl-3,5,8,8-tetramethyl-2,3,7,8 -tetrahydro-6H-furo[2,3-e]-indol-7-one•hydrochloride using HPLC (CHIRALPAK-AD, n-hexane:2-propanol:diethylamine=19:1:0.02).

The solvent was evaporated under reduced pressure from the first eluant to obtain 180 mg of an optically active free base. This base was made into hydrochloride and recrystallized from a mixed solvent of methanol and ether, to obtain 74 3 mg of optically active (2R*,3R*)-2-aminomethyl-3,5,8,8-tetramethyl-2,3,7,8-tetrahydro-6H-furo[2,3-e]indol-7-one•hydrochloride as a pale yellow powder.

mp: >300° C.

Optical purity: 70.8% ee (calculated from HPLC area ratios)

IR (KBr): 3406, 2955, 1690, 1642, 1506, 1480, 1451, 1247, 1089, 752 cm$^{-1}$.

$^1$H-NMR(CDCl$_3$–CD$_3$OD) δ: 1.38(3H, d, J=6.8 Hz), 1.42(3H, s), 1.44(3H, s), 2.21(3H, s), 3.10–3.35(3H, m), 4.54(1H, m), 6.80(1H, s).

The solvent was evaporated under reduced pressure from the second eluant to obtain 101 mg of an optically active free base. This base was treated in the same manner to obtain 140 mg of another optically active hydrochloride as a pale yellow powder.

mp: >300° C.

Optical purity: 97.7% ee (calculated from HPLC area ratios)

IR(KBr): 3391, 2955, 1692, 1642, 1505, 1477, 1451, 1244, 1088, 752 cm$^{-1}$.

$^1$H-NMR(CDCl$_3$–CD$_3$OD) δ: 1.38(3H, d, J=6.8 Hz), 1.42(3H, s), 1.43(3H, s), 2.21(3H, s), 3.10–3.35(3H, m), 4.54(1H, m), 6.79(1H, s).

Example 52

Optical resolution of (2R*,3S*)-2-aminomethyl-2,3,5,8,8-pentamethyl-2,3,7,8-tetrahydro-6 H-furo[2,3-e]indol-7-one•hydrochloride Optical resolution was carried out on a methanol solution of 680 mg of (±)-(2R*,3S)-2-aminomethyl-2,3,5,8,8-pentamethyl-2,3,7,8-tetrahydro-6 H-furo[2,3-e]indol-7-one•hydrochloride using HPLC (CHIRALPAK-AD, n-hexane:2-propanol:diethylamine=9:1:0.01).

The solvent was evaporated under reduced pressure from the first eluant to obtain 200 mg of an optically active free base. This base was made into hydrochloride and recrystallized from a mixed solvent of chloroform, methanol and ether, to obtain 110 mg of optically active (±)-(2R*,3S*)-2-aminomethyl-2,3,5,8,8 -pentamethyl-2,3,7,8-tetrahydro-6H-furo[2,3-e]indol-7-one•hydrochloride as a pale green powder.

mp: >300° C.

Optical purity: 98.6% ee (calculated from HPLC area ratios)

IR(KBr): 3226, 2892, 1722, 1649, 1456, 1261, 1038, 883 cm$^{-1}$.

$^1$H-NMR(CDCl$_3$–CD$_3$OD) δ: 1.26(3H, d, J=7.1 Hz), 1.39(3H, s), 1.42(3H, s), 1.55(3H, s), 2.19(3H, s), 3.13(2H, s), 3.27–3.36(1H, m, overlapped with solvent), 6.83(1H, s).

The solvent was evaporated under reduced pressure from the second eluant to obtain 253 mg of an optically active free base. This base was treated in the same manner to obtain 131 mg of (–)-hydrochloride as a pale green powder.

mp: >300° C.

Optical purity: 98.9% ee (calculated from HPLC area ratios).

IR(KBr): 3228, 2895, 1722, 1649, 1456, 1261, 1038, 883 cm$^{-1}$.

$^1$H-NMR(CDCl$_3$–CD$_3$OD) δ: 1.26(3H, d, J=7.1 Hz), 1.41(3H, s), 1.43(3H, s), 1.59(3H, s),2.21(3H, s), 3.10(2H, s), 3.31(1H, q, J=7.1 Hz), 6.77(1H, s).

Example 53

Optical resolution of 2-aminomethyl-2,3,7,8-tetrahydro-5,8,8 -trimethyl-6H-furo[2,3

Optical resolution was carried out on a 2-propanol solution of 1.01 g of (±)-2-aminomethyl-2,3,7,8-tetrahydro-5,8,8-trimethyl-6H-furo[2,3 -e]indol-7- one•hydrochloride using HPLC (CHIRALPAK-AD, n-hexane:2-propanol:diethylamine= 14:1:0.015).

The solvent was evaporated under reduced pressure from the first eluant to obtain 276 mg of an optically active free base. This base was made into hydrochloride and recrystallized from a mixed solvent of chloroform, methanol and ether, to obtain 274 mg of optically active (–)-2-aminomethyl-2,3,7,8-tetrahydro-5,8,8 -trimethyl-6H-furo[2,3-e]indol-7-one•hydrochloride as pale yellow powder.

mp: >300° C.

Optical rotation: $[α]_D^{22}$=–4.1 (C=1.0, MeOH)

Optical purity: 89.49% ee (calculated from HPLC area ratios)

IR (KBr): 3439, 2966, 1707, 1649, 1483, 1247, 1092, 976, 645 cm$^{-1}$.

$^1$H-NMR(CDCl$_3$–CD$_3$OD) δ: 1.41(3H, s), 1.44(3H, s), 2.20(3H, s), 2.91(1H, dd, J=7.3, 15.6 Hz), 3.11–3.42(3H, m, overlapped with solvent), 5.07(1H, m), 6.86(1H, s).

The solvent was evaporated under reduced pressure from the second eluant to obtain 303 mg of an optically active free base. This base was treated in the same manner to obtain 154 mg of (+)-hydrochloride as a pale yellow powder.

mp: >300° C.

Optical rotation: $[α]_D^{22}$=+4.8 (C=0.5, MeOH)

Optical purity: 85.6% ee (calculated from HPLC area ratios)

IR (KBr): 3440, 2968, 1678, 1645, 1482, 1247, 1085, 977, 636 cm$^{-1}$.

$^1$H-NMR(CDCl$_3$–CD$_3$OD) δ: 1.41(3H, s), 1.44(3H, s), 2.20(3H, d, J=0.7 Hz), 2.91(1H, dd, J=7.3, 15.6 Hz), 3.11–3.42(3H, m, overlapped with solvent), 5.07(1H, m), 6.86(1H, s).

Example 54

Optical resolution of (2R*,3S* )-2-aminomethyl-3,5,8,8-tetramethyl-2,3,7,8-tetrahydro- 6H-furo[2,3-e]indol-7-one•hydrochloride Optical resolution was carried out on a 2-propanol solution of 900 mg of (±)-(2R*,3S*)-2-aminomethyl-3,5,8,8-tetramethyl-2,3,7,8-tetrahydro-6H-furo[2,3-e]indol-7-one using HPLC (CHIRALPAK-AD, n-hexane: 2-propanol:diethylamine=19:1:0.02).

The solvent was evaporated under reduced pressure from the first eluant to obtain 293 mg of an optically active free base. This base was made into hydrochloride, decolorized by activated charcoal, and recrystallized from a mixed solvent of chloroform, methanol and ether, to obtain 163 mg of optically active (2R*,3S*)-2-aminomethyl-3,5,8,8-tetramethyl-2,3,7,8-tetrahydro- 6H-furo[2,3-e]indol-7-one•hydrochloride as a yellow powder.

mp: >300° C.
Optical purity: 76.0% ee (calculated from HPLC area ratios)
IR(KBr): 3222, 3112, 2968, 1696, 1482, 1457, 1248, 1105, 1066, 754 cm$^{-1}$.

$^1$H-NMR(CD$_3$OD) δ: 1.20(3H, d, J=7.3 Hz), 1.39(3H, s), 1.42(3H, s), 2.19(3H, s), 3.18–3.39(2H, overlapped with solvent), 3.57(1H, m), 4.80–4.96(1H, m), 6.87(1H, s).

The solvent was evaporated under reduced pressure from the second eluant to obtain 150 mg of an optically active free base. This base was treated in the same manner to obtain 126 mg of another optically active hydrochloride as a yellow powder.

mp: >300° C.
Optical purity: 88.3% ee (calculated from HPLC area ratios)
IR(KBr): 3224, 3111, 2969, 1695, 1482, 1457, 1250, 1106, 1066, 754 cm$^{-1}$.

$^1$H-NMR(CD$_3$OD) δ: 1.20(3H, d, J=7.1 Hz), 1.39(3H, s), 1.42(3H, s), 2.19(3H, s), 3.15–3.39(2H, m), 3.57(1H, m), 4.75–4.96(1H, m), 6.87(1H, s).

Example 55

Optical resolution of (2R*,3R*)-2 -aminomethyl-2,3,5,8,8-pentamethyl-2,3,7,8-tetrahydro-6 H-furo[2,3-e]-2,3,5,8,8-pentamethyl-2,3,7,8-tetrahydro-6 indol-7-one•hydrochloride Optical resolution was carried out on a n-hexane-2-propanol solution of 485 mg of (±)-(2R*,3R*)-2-aminomethyl-2,3,5,8,8-pentamethyl-2,3,7,8 -tetrahydro-6H-furo[2, 3-e]indol-7-one•free base using HPLC (CHIRALPAK-AD, n-hexane:2-propanol:diethylamine=9:1:0.01).

The solvent was evaporated under reduced pressure from the first eluant to obtain 163 mg of an optically active free base. This base was purified by column chromatography (silica gel, 10:1 mixture of chloroform and ammonia methanol), made into hydrochloride, and recrystallized from a mixed solvent of methanol and ether, to obtain 115 mg of optically active (2R*,3R*)-2-aminomethyl-2,3,5,8,8-pentamethyl-2,3,7,8-tetrahydro-6 H-furo[2,3-e]indol-7one•hydrochloride (A-isomer) as a colorless powder.

mp: >300° C.
Optical purity: 99.9% ee (calculated from HPLC area ratios)
IR(KBr): 3237, 3120, 2971, 2908, 1999, 1720, 1648, 1267, 1099 cm$^{-1}$.

$^1$H-NMR(CD$_3$OD) δ: 1.27(3H, d, J=7.1 Hz), 1.35(3H, s), 1.37(3H, s), 1.41(3H, s), 2.19(3H, s), 3.23(2H, s), 3.25–3.30(1H, overlapped with solvent), 6.84 (1H, s).

The solvent was evaporated under reduced pressure from the second eluant to obtain 195 mg of another optically active free base. This base was treated in the same manner to obtain 147 mg of another optically active hydrochloride (B isomer) as a pale yellow powder.

mp: >300° C.
Optical purity: 97.2% ee
IR(KBrneat): 3238, 3120, 2971, 2906, 1999, 1720, 1648, 1267, 1099 cm$^{-1}$.

$^1$H-NMR(CD$_3$OD) δ: 1.27(3H, d, J=7.1 Hz), 1.35(3H, s), 1.37(3H, s), 1.41(3H, s), 2.19(3H, s), 3.23(2H, s), 3.25–3.30(1H, overlapped with solvent), 6.84 (1H, s).

Example 56

Optical resolution of (2R*,3R*)-2-aminomethyl-3-ethyl-2, 5,8,8-tetramethyl-2,3,7,8 -tetrahydro-6H-furo[2,3-e]indol-7-one•hydrochloride Optical resolution was carried out on a n-hexane-2-propanol solution of 346 mg of (±)-(2R*,3R*)-2-aminomethyl-3-ethyl-2,5,8,8-tetramethyl- 2,3,7,8-tetrahydro-6H-furo[2,3-e]indol-7-one•free base using HPLC (CHIRALPAK-AS, n-hexane:2-propanol:diethylamine= 9:1:0.01).

The solvent was evaporated under reduced pressure from the first eluant to obtain 145 mg of an optically active free base. This base was made into hydrochloride and recrystallized from a mixed solvent of methanol and ether to obtain 111 mg of optically active (2R*,3R*)-2-aminomethyl-3-ethyl- 2,5,8,8-tetramethyl-2,3,7,8-tetrahydro-6H-furo[2,3-e] indol-7-one•hydrochloride as a yellow powder.

mp: 255° C.
Optical purity: 62.3% ee (calculated from HPLC area ratios)
IR(KBr): 3430, 3192, 2968, 1701, 1481, 1457, 1260, 1093 cm$^{-1}$.

$^1$H-NMR(CD$_3$OD) δ: 0.99(3H, t, J=7.4 Hz), 1.39(3H, s), 1.43(3H, s), 1.59–1.85(2H, m), 2.19(3H, s), 3.02–3.22(3H, cm), 4.65(1H, m), 6.88(1H, s).

The solvent was evaporated under reduced pressure from the second eluant to obtain 126 mg of another optically active free base. This base was treated in the same manner to obtain 76 mg of another optically active hydrochloride as a pale yellow powder.

mp: 256° C.
Optical purity: 98.6% ee
IR(KBr): 3429, 3192, 2968, 1701, 1481, 1457, 1260, 1093 cm$^{-1}$.

$^1$H-NMR(CD$_3$OD) δ: 0.99(3H, t, J=7.4 Hz), 1.39(3H, s), 1.43(3H, s), 1.59–1.85(2H, m), 2.19(3H, s), 3.02–3.22(3H, m), 4.65(1H, m), 6.88(1H, s).

Example 57

Optical resolution of (2R*,3S*)-2-aminomethyl-3-ethyl-2,5,8,8-tetramethyl-2,3,7,8-tetrahydro- 6H-furo[2,3-e]indol-7-one•hydrochloride Optical resolution was carried out on a n-hexane-2-propanol solution of 30 mg of (±)-(2R*,3S*)-2-aminomethyl-3-ethyl-2,5,8,8-tetramethyl-2,3,7,8 -tetrahydro-6H- furo[2,3-e]indol-7-one•free base using HPLC (CHIRALPAK-AS, n-hexane:2-propanol:diethylamine= 9:1:0.01).

The solvent was evaporated under reduced pressure from the first eluant to obtain 192 mg of an optically active free base. This base was made into hydrochloride and recrystallized from a mixed solvent of methanol and ether to obtain 157 mg of optically active (2R*,3S*)-2-aminomethyl-3-ethyl-2,5,8,8-tetramethyl-2,3,7,8-tetrahydro-6H-furo[2,3-e]indol-7-one•hydrochloride as a pale brown powder.

mp: >300° C.

Optical rotation: $[\alpha]_D^{22}$=+8.0 (C=0.44, MeOH)

IR(KBr): 3421, 2926, 1710, 1648, 1458, 1310, 1260, 991 cm$^{-1}$.

$^1$H-NMR(CD$_3$OD) δ: 1.02(3H, d, J=7.3 Hz), 1.39(3H, s), 1.42(3H, s), 1.45–1.69(2H, m), 2.20(3H, s), 3.21–3.51(3H, overlapped with solvent), 4.72–4.95(1H, m), 6.91(1H, s).

The solvent was evaporated under reduced pressure from the second eluant to obtain 189 mg of another optically active free base. This base was treated in the same manner to obtain 141 mg of another optically active hydrochloride as a pale brown powder.

mp: >300° C.

Optical rotation: $[\alpha]_D^{22}$=−13.9 (C=0.40, MeOH)

IR(KBr): 3441, 2930, 1710, 1647, 1458, 1310, 1260, 992 cm$^{-1}$.

$^1$H-NMR(CD$_3$OD) δ: 1.02(3H, t, J=7.4 Hz), 1.39(3H, s), 1.42(3H, s), 1.45–1.69(2H, m), 2.20(3H, s), 3.21–3.51(3H, overlapped with solvent), 4.72–4.95(1H, m), 6.91(1H, s).

Example 58

Optical resolution of (2R*,3S*)-2-aminomethyl-2,3,7,8-tetrahydro-2,3,5,8,8-pantamethyl-6 H-furo[2,3-e]indol-7-thione Optical resolution was carried out on a n-hexane-2-propanol solution of 660 mg of (+)-(2R*,3S*)-2-aminomethyl-2,3,7,8-tetrahydro-2,3,5,8,8-pantamethyl-6H-furo[2,3-e]indol-7-thione•free base using HPLC (CHIRALPAK-AS, n-hexane:2-propanol:diethylamine= 9:1:0.1).

The solvent was evaporated under reduced pressure from the first eluant to obtain 290 mg of an optically active free base. This base was purified by column chromatography (silica gel, 10:1 mixture of chloroform-chloroform/methanol (saturated ammonia)), made into hydrochloride, and recrystallized from a mixed solvent of methanol and ether to obtain 192 mg (25.7%) of (−)-(2R*, 3S*)-2-aminomethyl-2,3,7,8-tetrahydro-2,3,5,8,8-pantamethyl-6H-furo[2,3 -e]-indol-7-thione•hydrochloride as a pale yellow powder.

mp: >300° C.

Optical rotation: $[\alpha]_D^{22}$−9.55 (C=0.67, MeOH)

Optical purity: 99.9% ee (calculated from HPLC area ratios)

IR(KBr): 3431, 3105, 2966, 2857, 1644, 1479, 1449, 1265, 1089, 1054, 1037, 882 cm$^{-1}$.

$^1$H-NMR(CD$_3$OD) δ: 1.27(3H, d, J=7.3 Hz), 1.42(3H, s,), 1.45(3H, s), 1.57(3H, s), 2.27(3H, s), 3.15(2H, s), 4.85–4.93(1H, m), 6.89(1H, s).

The solvent was evaporated under reduced pressure from the second eluant to obtain 297 mg of an optically active free base. This base was purified by column chromatography (silica gel, 10:1 mixture of chloroform-chloroform/methanol (saturated ammonia)), made into hydrochloride, and recrystallized from a mixed solvent of methanol and ether to obtain 206 mg (27.8%) of (+)-(2R*,3S*)-2-aminomethyl-2,3,7,8-tetrahydro- 2,3,5,8,8-pantamethyl-6H-furo[2,3-e]indol-7-thione•hydrochloride as a pale yellow powder.

mp: >300° C.

Optical rotation: $[\alpha]_D^{22}$=+8.99 (C=0.89, MeOH)

Optical purity: 99.2% ee (calculated from HPLC area ratios)

IR (KBr): 3412, 3107, 2966, 2857, 1643, 1479, 1449, 1265, 1090, 1054, 1037, 882 cm$^{-1}$.

$^1$H-NMR(CD$_3$OD) δ: 1.27(3H, d, J=7.1 Hz), 1.42(3H, s), 1.45(3H, s), 1.57(3H, s), 2.27(3H, s), 3.15(2H, s), 4.85–4.93(1H, m), 6.89 (1H, s).

Example 59

Optical resolution of 2R*,3R*)-2-aminomethyl-2,3,7,8-tetrahydro-3,5,8,8-tetramethyl-6 H-furo[2,3-e]indol-7-thione Optical resolution was carried out on a n-hexane-2-propanol solution of 584 mg of (±)-(2R*,3R*)-2-aminomethyl-2,3,7,8-tetrahydro-3,5,8,8 -tetramethyl-6H-furo[2,3-e]indol-7-thione•free base using HPLC (CHIRALPAK-AS, n-hexane:2-propanol:diethylamine=9:1:0.1).

The solvent was evaporated under reduced pressure from the first eluant to obtain 185 mg of an optically active free base. This base was made into hydrochloride and recrystallized from a mixed solvent of methanol and ether to obtain 151 mg (22.8%) of (+)-(2R*,3R*)-2-aminomethyl-2,3,7,8-tetrahydro-3,5,8,8 -tetramethyl-6H-furo[2,3-e]indol-7-thione•hydrochloride as a yellow powder.

mp: >300° C.

Optical rotation: $[\alpha]_D^{22}$=+27.9 (C=0.33, MeOH)

Optical purity: 97.2% ee (calculated from HPLC area ratios)

IR(KBr): 3171, 2968, 2901, 1647, 1590, 1479, 1447, 1247, 1087, 1034, 968 cm$^{-1}$.

$^1$H-NMR(CD$_3$OD) δ: 1.37(3H, d, J=6.8 Hz), 1.43(3H, s), 1.45(3H, s), 2.27(3H, s), 3.22(1H, dd, J=13.7, 9.0 Hz), 3.38(1H, dd, J=13.7, 3.2 Hz), 4.51(1H, s), 4.75–4.93(1H, m), 6.90(1H, s).

The solvent was evaporated under reduced pressure from the second eluant to obtain 147 mg of an optically active free base. This base was made into hydrochloride and recrystallized from a mixed solvent of methanol and ether to obtain 134 mg (20.2%) of (−)-(2R* 3R*)-2-aminomethyl-2,3,7,8-tetrahydro- 3,5,8,8-tetramethyl-6H-furo[2,3-e]indol-7-thione•hydrochloride as a yellow powder.

mp: >300° C.

Optical rotation: $[\alpha]_D^{22}$=−41.5 (C=0.26, MeOH)

Optical purity: 99.9% ee (calculated from HPLC area ratios)

IR(KBr): 3172, 2969, 2917, 1648, 1589, 1479, 1453, 1247, 1097, 1034, 969 cm$^{-1}$.

$^1$H-NMR(CD$_3$OD) δ: 1.37(3H, d, J=6.8 Hz), 1.43(3H, s), 1.45(3H, s), 2.27(3H, s), 3.22(1H, dd, J=13.7, 8.8 Hz), 3.30–3.42(4H, m), 4.51(1H, s), 4.75– 4.93(1H, m), 6.90(1H, s).

Example 60

(1) 6-Benzyl-2-methanesulfonyloxy-8-methoxycarbonylmethylidene-5-methyl-2,3-7,8 -tetrahydro-6H-furo[2,3-e]indol-7-one 4.0 mg (9.97 μmol) of 6-benzyl-2-methanesulfonyloxy-5-methyl-2,3,7,8-tetrahydro- 6H-furo[2,3-e]indol-7-one was dissolved in 0.21 ml of methylene chloride. To the solution 6.7 mg (20.0 μmol) of methyl triphenylphosphoranilidene acetate was added and the mixture was stirred for 12 hours at room temperature. The residue obtained by concentrating the reaction mixture under reduced pressure was purified by separation thin layer chromatography (silica gel, 10:1 mixture of chloroform and methanol) to obtain 2.3 mg of the title compound (2:1 mixture of geometrical isomers, 50.5%) as a yellow foam.

IR(Cap.): 3442, 3027, 2927, 2855, 1709, 1639, 1617, 1483, 1439, 1408, 1394, 1359, 1260, 1216, 1175, 1130, 1021, 997, 965, 913, 818, 759, 698, 667 cm$^{-1}$.

$^1$H-NMR(CDCl$_3$) δ: 2.16(s) 2.17(s) (3H, altogether), 2.95(1H, dd, J=5.4, 15.6 Hz), 3.06(s), 3.10(s) (3H, altogether), 3.28(1H, dd, J=9.5, 15.6 Hz), 3.90(s), 3.91(s) (3H, altogether), 4.24(dd, J=6.3, 11.0 Hz), 4.39(dd, J=6.1, 11.0 Hz) (1H, altogether), 4.40(dd, J=3.4, 11.2 Hz), 4.46(dd, J=4.4, 11.2 Hz) (1H, altogether), 5.15(1H, m), 5.16(s) 5.21(s) (1H, altogether), 6.80(s) 6.81(s) (1H, altogether), 6.92(s) 7.03(s) (1H, altogether), 7.13(2H, d, J=6.6 Hz), 7.22–7.34(3H, m).

(2) 6-Benzyl-2-methanesulfonyloxymethyl-8-methoxycarbonylmethyl-5-methyl-2,3-7,8 -tetrahydro-6H-furo[2,3-e]indol-7-one 2.1 mg (4.66 μmol) of 6-benzyl-2-methanesulfonyloxymethyl-8-methoxycarbonyl-methylidene- 5-methyl-2,3-7,8-tetrahydro-6H-furo[2,3-e]indol-7-one was dissolved in 2 ml of acetic acid. 8.0 mg of 10% palladium-carbon catalyst was added to the solution and the mixture was stirred for one hour at 60° C. under a hydrogen atmosphere. The reaction mixture was filtered and the filtrate was concentrated under reduced pressure. The residue was purified by separation thin layer chromatography (silica gel, 20:1 mixture of chloroform and methanol) to obtain 1.4 mg of title compound (diastereomer, about 1:1 mixture, 66.4%) as a colorless foam.

IR(Cap.): 3452, 3023, 2955, 2927, 2855, 1735, 1709, 1651, 1617, 1497, 1483, 1469, 1455, 1441, 1412, 1393, 1360, 1261, 1215, 1175, 1138, 993, 965, 821, 759, 698, 667 cm$^{-1}$.

$^1$H-NMR(CDCl$_3$) δ: 2.18(3H, s), 2.96(1H, dd, J=6.6, 15.6 Hz), 3.06(s) 3.10(s) (3H, altogether), 3.10(t, J=6.6 Hz), 3.12(t, J=7.1 Hz) (2H, altogether), 3.27(1H, dd, J=9.5, 15.6 Hz), 3.66(s) 3,68(s) (3H, altogether), 3.86(1H, m), 4.27–4.39(2H, m), 5.06(1H, m), 5.15(1H, d, J=6.4 Hz), 5.22(1H, d, J=6.4 Hz), 6.87(1H, s), 7.19–7.65(5H, m).

Example 61

(1) 6-Benzyl-8-ethyl-8-hydroxy-2-methanesulfonyloxymethyl-5-methyl-2,3-7,8 -tetrahydro-6H-furo[2,3-e]indol-7-one 1.7 mg (54.1 μmol) of 6-benzyl-2-methanesulfonyloxymethyl-5-methyl-2,3,7,8 -tetrahydro-6H-furo[2,3-e]indol-7,8-dione was suspended in 1 ml of tetrahydrofuran. 0.09 ml of ethyl magnesium bromide (0.99N tetrahydrofuran solution) was added at −78° C., and the mixture was stirred for 20 minutes at −78° C. Methanol was added to the reaction mixture, and after neutralizing an excess amount of ethyl magnesium bromide, the mixture was extracted with chloroform-1N hydrochloric acid. The organic layer was dried over anhydrous sodium sulfate. The residue obtained by concentration under reduced pressure was purified by separation thin layer chromatography (silica gel, 10:1 mixture of chloroform and methanol) to obtain 16.2 mg of the title compound (diastereomer, about 2:1 mixture, 69.5%) as a pale yellow foam.

(2) 8-Ethyl-2-methanesulfonyloxymethyl-5-methyl-2,3,7,8-tetrahydro-6H-furo[2,3-e]indol-7-one (a) and 2,5-dimethyl-8-ethyl-2,3,7,8-tetrahydro-6H-furo[2,3-e]-indol-7-one (b)

16.0 mg (37.1 μmol) of 6-benzyl-8-ethyl-8-hydroxy-2-methanesulfonyloxymethyl-5 -methyl-2,3–7,8-tetrahydro-6H-furo[2,3-e]indol-7-one was dissolved in 1.5 ml of acetic acid. 21.0 mg of 10% palladium-carbon catalyst was added to the solution and the mixture was stirred for 19 hours at 80° C. under a hydrogen atmosphere. The reaction mixture was filtered and the filtrate was concentrated under reduced pressure. The residue was purified by separation thin layer chromatography (silica gel, 10:1 mixture of chloroform and methanol) to obtain 2.9 mg (24.0%) of title compound (a) as a pale yellow foam and 2.1 mg (24.5%) of title compound (b) as a colorless solid.

Compound (a)

IR(Cap.): 3222, 2925, 2854, 1704, 1646, 1481, 1456, 1357, 1306, 1241, 1175, 1091, 1047, 992, 965, 821, 756 cm$^{-1}$.

$^1$H-NMR(CDCl$_3$) δ: 0.87(3H, t, J=7.5 Hz), 2.01–2.15(2H, m), 2.16 (3H, s), 2.98(1H, dd, J=6.9, 15.4 Hz), 3.27(1H, dd, J=9.3, 15.4 Hz), 3.72(1H, dd, J=6.8, 13.9 Hz), 4.36–4.38(2H, m), 5.05(1H, m), 6.85(1H, s).

Compound (b)

IR (Cap.): 3457, 3174, 2924, 2854, 1699, 1641, 1446, 1382, 1306, 1270, 1240, 1147, 1106, 1084, 1039, 923, 898, 864,823, 786,743 cm$^{-1}$.

$^1$H-NMR(CDCl$_3$) δ: 0.92(3H, t, J=7.5 Hz), 1.44(3H, d, J=6.4 Hz), 2.02–2.13(2H, m), 2.14(3H, s), 2.73(1H, dd, J=6.9, 15.9 Hz), 3.24(1H, dd, J=9.3, 15.9 Hz), 3.76(1H, dd, J=5.3, 10.5 Hz), 4.92(1H, m), 6.81(1H, s).

Example 62

(1) 6-Benzyl-8-hydroxy-8-isopropyl-2-methanesulfonyloxymethyl-5-methyl-2,3-7,8 -tetrahydro-6H-furo[2,3-e]indol-7-one 20.2 mg (50.4 μmol) of 6-benzyl-2-methanesulfonyloxymethyl-5-methyl-2,3,7,8-tetrahydro- 6H-furo[2,3-e]indol-7,8-dione was suspended in 1 ml of tetrahydrofuran. 0.15 ml (0.224 mmol) of isopropyl magnesium bromide (0.67N tetrahydrofuran solution) was added at −40° C., and the mixture was stirred for 5 minutes at −40° C. Methanol was added to the reaction mixture, and after neutralizing an excess amount of isopropyl magnesium bromide, the mixture was extracted with chloroform-1N hydrochloric acid. The organic layer was dried over anhydrous sodium sulfate. The residue obtained by concentration under reduced pressure was purified by separation thin layer chromatography (silica gel, 10:1 mixture of chloroform and methanol) to obtain 9.9 mg of the title compound (diastereomer, about 3:2 mixture, 44.2%) as a pale yellow foam.

IR (Cap.): 3416, 3029, 2964, 2932, 2875, 1714, 1640, 1618, 1497, 1480, 1454, 1441, 1412, 1393, 1355, 1295, 1259, 1214, 1174, 1121, 1078, 1046, 991,965, 911, 822, 755, 729 cm$^{-1}$.

$^1$H-NMR(CDCl$_3$) δ: 1.00(3H, d, J=6.8 Hz), 1.04(3H, d, J=6.8 Hz), 2.17(3H, s), 2.49(1H, septet, J=6.8 Hz), 2.93(dd, J=6.4, 16.4 Hz), 2.96(dd, J=6.4, 16.4 Hz) (1H, altogether), 3.05(s) 3.11(s) (3H, altogether), 3.26(dd, J=4.4, 16.4 Hz), 3.31(dd, J=4.4, 16.4 Hz) (1H, altogether), 4.37–4.42(2H, m), 5.11(1H, m), 5.12(2H, s), 6.79(1H, s), 7.15(2H, d, J=7.1 Hz), 7.21–7.34(3H, m).

(2) 8-Isopropyl-2-methanesulfonyloxymethyl-5-methyl-2,3, 7,8-tetrahydro-6 H-furo[2,3-e]indol-7-one (a) and 2,5-dimethyl-8-isopropyl-2,3,7,8-tetrahydro-6H-furo[ 2,3-e]indol-7-one (b)

9.8 mg (22.0 μmol) of 6-benzyl-8-hydroxy-8-isopropyl-2-methanesulfonyloxymethyl-5-methyl- 2,3–7,8-tetrahydro-6H-furo[2,3-e]indol-7-one was dissolved in 2 ml of acetic acid. 20.0 mg of 10% palladium-carbon catalyst was added to the solution and the mixture was stirred for 16 hours at 80° C. under a hydrogen atmosphere. The reaction mixture was filtered and the filtrate was concentrated under reduced pressure. The residue was purified by separation thin layer chromatography (silica gel, 10:1 mixture of chloroform and methanol) to obtain 2.1 mg (28.1%) of title compound (a) as a pale yellow foam and 2.1 mg (38.9%) of title compound (b) as a colorless solid.

Compound (a)

IR(Cap.): 3265, 2957, 2925, 2854, 2363, 1704, 1645, 1463, 1359, 1243, 1176, 1095, 992, 965, 822, 759, 700, 667 $cm^{-1}$.

$^1$H-NMR(CDCl$_3$) δ: 0.97(3H, d, J=6.8 Hz), 1.04(3H, d, J=6.8 Hz), 2.55(1H, m), 3.02(1H, dd, J=6.9, 15.4 Hz), 3.04(3H, s), 3.29(1H, dd, J=9.3, 15.4 Hz), 3.72(1H, d, J=7.1 Hz), 4.35–4.38(2H, m), 5.06(1H, m), 6.84(1H, s),

Compound (b)

IR(Cap.): 3175, 3018, 2926, 2855, 1695, 1635, 1455, 1383, 1307, 1244, 1216, 1176, 1090, 1042, 827, 758 $cm^{-1}$.

$^1$H-NMR(CDCl$_3$) δ: 1.00(3H, d, J=6.8 Hz), 1.06(3H, d, J=6.8 Hz), 1.44(3H, d, J=6.4 Hz), 2.13(3H, s), 2.57(1H, m), 2.73(1H, dd, J=7.1, 15.9 Hz), 3.25(1H, dd, J=9.3, 15.9 Hz), 3.67(1H, d, J=7.1 Hz), 4.91(1H, m), 6.81 (1H, s).

Test Example 1

<Antiarrhythmic action against chloroform in mice>

A test compound was administered to mice at a dose of 100 mg/kg. After 20 minutes, mice were placed in a pot filled with chloroform. Mice were taken out immediately after respiratory arrest. Electrocardiogram was recorded at the 11th induction, and ventricular tachycardia, ventricular fibrillation, and the time until cardiac arrest were measured. The results, as shown in Table 1, were indicated in terms of the rate of suppressing ventricular fibrillation.

TABLE 1

| Test compound | Rate of suppression (%) |
| --- | --- |
| Example 11 (9) | 90 |
| Example 15 | 100 |
| Example 16 | 90 |
| Example 17 | 100 |
| Example 25 (9) | 100 |
| Example 28 (9)HCl | 90 |
| Example 35 | 100 |
| Example 47 (5) | 90 |
| Example 55 (B isomer)* | 100 |

*Dose: 30 mg/kg

Test Example 2

<Inoropic action in atrium specimen and anti-chronotropic action in guinea pigs>

After bruising on the head, guinea pigs were dehematized by sectioning carotid arteries and their heart was enucleated. Right and left atriums were taken out. These atriums were suspended in Krebs-Henseleit solution wherein 95% O$_2$-5% CO$_2$ was bubbled. The tension was measured by a strain gauge and recorded via an amplifier. Pulsation at the right atrium was counted via a tachometer to determine the heart rate. Electric stimulation, twice a magnitude of the ceiling value at 1 Hz, 5 msec, was given to the left atrium. The test compound was administered at an interval of 5 minutes.

The results, shown in Table 2, indicate the rate of contraction increase of the light atrium at a dose of 10$^{-5}$M of the test compound.

TABLE 2

| Test compound | Rate contraction increase (%) |
| --- | --- |
| Example 1 (9) | 13 |
| Example 2 (8) | 23 |
| Example 7 (6)(b) | 27 |
| Example 14 | 20 |
| Example 19 | 28 |
| Example 25 (9) | 46 |
| Example 30 (8)HCl | 28 |
| Example 55 (B isomer) | 24 |

Test Example 3

<Action on hind-leg blood flow in anesthetized dogs>

Hybrid adult dogs were anesthetized by intravenous injection of 30 mg/kg of sodium pentobarbital. After administration of heparin, an extracorporeal circulation circuit was formed in femoral artery. The blood flows at hind-legs were measured by fixing an electromagnetic blood flow meter probe in the circuit. The test compound at a dose of 100 μg was administered into femoral artery via a tube provided in the circuit. The results in Table 3 show the rate of blood flow increase.

TABLE 3

| Test compound | Rate of blood flow increase (%) |
| --- | --- |
| Example 1 (a) | 192 |
| Example 3 (5) (Former component) | 128 |
| Example 13 (3) | 55 |
| Example 16 | 90 |
| Example 18 | 145 |
| Example 20 | 96 |
| Example 22 | 121 |
| Example 23 | 81 |
| Example 26 (6) | 216 |
| Example 55 (B isomer) | 55 |

The compound (1) of the present invention exhibits a positive inotropic action on cardiac muscle, an anti-arrhythmic action, and a vasodilation action without increasing the heart rate. The heart affection therapeutic agent comprising this compound as an effective component is extremely effective for treating heart failures and arrhythmia.

Obviously, numerous modifications and variations of the present invention are possible in light of the above teachings. It is therefore to be understood that within the scope of the appended claims, the invention may be practiced otherwise than as specifically described herein.

What is claimed is:

1. An indole derivative represented by the following formula (1),

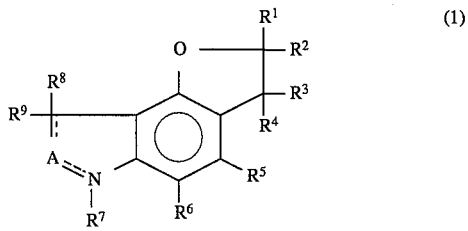

wherein at least one of $R^1$, $R^2$, $R^3$, or $R^4$ is a lower alkyl or alkenyl group which may have substituents selected from halogen atoms, hydroxy group, alkylsulfonyloxy groups, alkylsilyloxy groups, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or a lower alkyl group; $R^5$ and $R^6$ individually represent a hydrogen atom, a halogen atom, a lower alkyl or acyl group, or a lower alkyl group which may have substituents selected from hydroxy group, halogens, cyano group, alkoxycarbonyl groups, and carboxy groups; $R^7$ may either represent a hydrogen atom or a benzyl group, or form a double bond with A; and $R^8$ and $R^9$ individually represent a hydrogen atom, a halogen atom, a hydroxy group, or a lower alkyl group which may have substituents selected from hydroxy group, halogens, cyano group, alkoxycarbonyl groups, and carboxy groups, or $R^8$ and $R^9$ may together represent an oxygen atom, an alkenyl group, or either one of $R^8$ and $R^9$ may form a double bond with A; and A represents a group

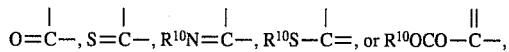

wherein $R^{10}$ is a hydrogen atom or a group; and the dotted line indicates that the bond may be a double bond; or a pharmaceutically acceptable salt thereof.

2. The compound of claim 1, wherein at least one of $R^1$, $R^2$, $R^3$, or $R^4$ is an alkyl or alkenyl group having 1–8 carbon atoms which may have substituents selected from halogen atoms, hydroxy group, alkylsulfonyloxy groups having 1–8 carbon atoms, alkylsilyloxy groups having 1–8 carbon atoms, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group having 1–8 carbon atoms; $R^5$ and $R^6$ individually represent a hydrogen atom, a halogen atom, an alkyl group having 1–8 carbon atoms, or an alkanoyl group having 1–6 carbon atoms; $R^7$ is a hydrogen atom or a benzyl group; $R^8$ and $R^9$ are a hydrogen atom, a halogen atom, a hydroxy group, or an alkyl group having 1–8 carbon atoms; and A is a group

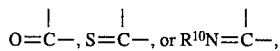

wherein $R^{10}$ is a hydrogen atom or an alkyl group having 1–8 carbon atoms.

3. The compound of claim 1, wherein at least one of $R^1$, $R^2$, $R^3$, or $R^4$ is an alkyl group having 1–8 carbon atoms which may have substituents selected from halogen atoms, hydroxy group, alkylsulfonyloxy groups having 1–8 carbon atoms, alkylsilyloxy groups having 1–8 carbon atoms, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group having 1–8 carbon atoms; $R^5$ and $R^6$ individually represent a hydrogen atom, a halogen atom, an alkyl group having 1–8 carbon atoms, or an alkanoyl group having 1–6 carbon atoms; $R^n$ is a hydrogen atom or a benzyl group; $R^8$ and $R^9$ are a hydrogen atom, a halogen atom, a hydroxy group, or an alkyl group having 1–8 carbon atoms; and A is a group

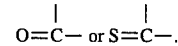

4. A pharmaceutical composition, comprising:
(i) an effective amount of the indole derivative of formula (1)

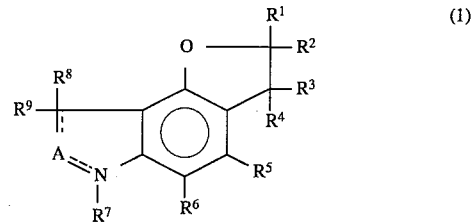

wherein at least one of $R^1$, $R^2$, $R^3$, or $R^4$ is a lower alkyl or alkenyl group which may have substituents selected from halogen atoms, hydroxy group, alkylsulfonyloxy groups, alkylsilyloxy groups, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group; $R^5$ and $R^6$ individually represent a hydrogen atom, a halogen atom, a lower alkyl or acyl group, or a lower alkyl group which may have substituents selected from hydroxy group, halogens, cyano group, alkoxycarbonyl groups, and carboxy groups; $R^7$ may either represent a hydrogen atom or a benzyl group, or form a double bond with A; and $R^8$ and $R^9$ individually represent a hydrogen atom, a halogen atom, a hydroxy group, or a lower alkyl group which may have substituents selected from hydroxy group, halogens, cyano group, alkoxycarbonyl groups, and carboxy groups, or $R^8$ and $R^9$ may together represent an oxygen atom, an alkenyl group, or either one of $R^8$ and $R^9$ may form a double bond with A; and A represents a group

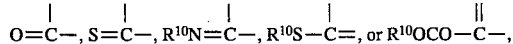

wherein $R^{10}$ is a hydrogen atom or a lower alkyl group; and the dotted line indicates that the bond may be a double bond; or a pharmaceutically acceptable salt thereof; and (ii) a pharmaceutically acceptable carrier.

5. The composition of claim 4, wherein at least one of $R^1$, $R^2$, $R^3$, or $R^4$ is an alkyl or alkenyl group having 1–8 carbon atoms which may have substituents selected from halogen atoms, hydroxy group, alkylsulfonyloxy groups having 1–8 carbon atoms, alkylsilyloxy groups having 1–8 carbon atoms, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group having 1–8 carbon atoms; $R^5$ and $R^6$ individually represent a hydrogen atom, a halogen atom, an alkyl group having 1–8 carbon atoms, or an alkanoyl group having 1–6 carbon atoms; $R^7$ is a hydrogen atom or a benzyl group; $R^8$ and $R^9$ are a hydrogen atom, a halogen atom, a hydroxy group, or an alkyl group having 1–8 carbon atoms; and A is a group

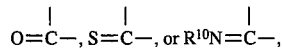

wherein $R^{10}$ is a hydrogen atom or an alkyl group having 1–8 carbon atoms.

6. The composition of claim 4, wherein at least one of $R^1$, $R^2$, $R^3$, or $R^4$ is an alkyl group having 1–8 carbon atoms which may have substituents selected from halogen atoms, hydroxy group, alkylsulfonyloxy groups having 1–8 carbon atoms, alkylsilyloxy groups having 1–8 carbon atoms, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substitutents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group having 1–8 carbon atoms; $R^5$ and $R^6$ individually represent a hydrogen atom, a halogen atom, an alkyl group having 1–8 carbon atoms, or an alkanoyl group having 1–6 carbon atoms; $R^7$ is a hydrogen atom or a benzyl group; $R^8$ and $R^9$ are a hydrogen atom, a halogen atom, a hydroxy group, or an alkyl group having 1–8 carbon atoms; and and A is a group

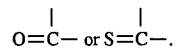

7. A method of treating a patient suffering from congestive heart failure, which comprises administering an effective amount of an indole derivative of formula (1) to said patient

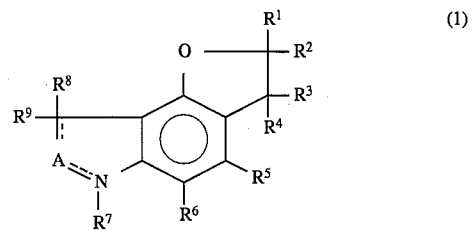

wherein at least one of $R^1$, $R^2$, $R^3$, or $R^4$ is a lower alkyl or alkenyl group which may have substituents selected from halogen atoms, hydroxy group, alkylsulfonyloxy groups, alkylsilyloxy groups, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or a lower alkyl group; $R^5$ and $R^6$ individually represent a hydrogen atom, a halogen atom, a lower alkyl or acyl group, or a lower alkyl group which may have substituents selected from hydroxy group, halogen, cyano group, alkoxycarbonyl groups, and carboxy groups; $R^7$ may either represent a hydrogen atom or a benzyl group, or form a double bond with A; and $R^8$ and $R^9$ individually represent a hydrogen atom, a halogen atom, a hydroxy group, or a lower alkyl group which may have substituents selected from hydroxy group, halogens, cyano group, alkoxycarbonyl groups, and carboxy groups, or $R^8$ and $R^9$ may together represent an oxygen atom, an alkenyl group, or either one of $R^8$ and $R^9$ may form a double bond with A; and A represents a group

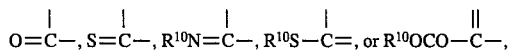

wherein $R^{10}$ is a hydrogen atom or a lower alkyl group; and the dotted line indicates that the bond may be a double bond; or a pharmaceutically acceptable salt thereof.

8. The method of claim 7, wherein at least one of $R^1$, $R^2$, $R^3$, or $R^4$ is an alkyl or alkenyl group having 1–8 carbon atoms which may have substituents selected from halogen atoms, hydroxy group, alkylsulfonyloxy groups having 1–8 carbon atoms, alkylsilyloxy groups having 1–8 carbon atoms, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group having 1–8 carbon atoms; $R^5$ and $R^6$ individually represent a hydrogen atom, a halogen atom, an alkyl group having 1–8 carbon atoms, or an alkanoyl group having 1–6 carbon atoms; $R^7$ is a hydrogen atom or a benzyl group; $R^8$ and $R^9$ are a hydrogen atom, a halogen atom, a hydroxy group, or an alkyl group having 1–8 carbon atoms; and A is a group

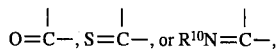

wherein $R^{10}$ is a hydrogen atom or an alkyl group having 1–8 carbon atoms.

9. The method of claim 7, wherein at least one of $R^1$, $R^2$, $R^3$, or $R^4$ is an alkyl group having 1–8 carbon atoms which may have substituents selected from halogen atoms, hydroxy group, alkylsulfonyloxy groups having 1–8 carbon atoms, alkylsilyloxy groups having 1–8 carbon atoms, azido group, cyano group, amino group, alkylamino groups having 1–8 carbon atoms, dialkylamino groups having 2–16 carbon atoms, phenyl alkylamino groups having 7–12 carbon atoms, alkanoylamino groups having 1–6 carbon atoms, alkoxycarbonylamino groups having 2–10 carbon atoms, pyrrole, pyrrolidine, imidazole, imidazoline, oxazole, oxazoline, thiazole, thiazoline, piperidine, piperazine, and morpholine (wherein these cyclic amino groups may further contain substituents selected from alkyl or alkenyl groups having 1–8 carbon atoms, phenyl alkyl groups having 7–15 carbon atoms, alkanoyl groups having 1–6 carbon atoms, benzoyl group, alkoxybenzoyl groups having 1–8 carbon atoms, and di($C_{1-8}$)alkoxybenzoyl groups), and others represent a hydrogen atom or an alkyl group having 1–8 carbon atoms; $R^5$ and $R^6$ individually represent a hydrogen atom, a halogen atom, an alkyl group having 1–8 carbon atoms, or an alkanoyl group having 1–6 carbon atoms; $R^7$ is a hydrogen atom or a benzyl group; $R^8$ and $R^9$ are a hydrogen atom, a halogen atom, a hydroxy group, or an alkyl group having 1–8 carbon atoms; and A is a group

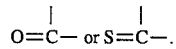

* * * * *

UNITED STATES PATENT AND TRADEMARK OFFICE
CERTIFICATE OF CORRECTION

PATENT NO. : 5,510,366
DATED : April 23, 1996
INVENTOR(S) : Yoshinori KYOTANI, et al.

It is certified that error appears in the above-indentified patent and that said Letters Patent is hereby corrected as shown below:

On the title page, in Item [75], the first inventor, Yoshinori Kyotani's place of residence should be:

--Higashiyamato, Japan--

Signed and Sealed this

Sixth Day of August, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,510,366

DATED : April 23, 1996

INVENTOR(S): Yoshinori KYOTANI et al

It is certified that an error appears in the above-identified patent and that said Letters Patent is hereby corrected as shown below:

Column 77, line 31, after "hydrogen atom or a", insert --lower alkyl--.

Signed and Sealed this

Fourth Day of January, 2000

Attest:

Attesting Officer

Acting Commissioner of Patents and Trademarks